US007613518B2

(12) United States Patent
Qin et al.

(10) Patent No.: US 7,613,518 B2
(45) Date of Patent: Nov. 3, 2009

(54) INTERFERENTIAL AND NEUROMUSCULAR ELECTRICAL STIMULATION SYSTEM AND APPARATUS

(75) Inventors: Li Qin, Mankato, MN (US); Gary L. Moore, New Brighton, MN (US)

(73) Assignee: Encore Medical Asset Corporation, Henderson, NV (US)

(*) Notice: Subject to any disclaimer, the term of this patent is extended or adjusted under 35 U.S.C. 154(b) by 398 days.

(21) Appl. No.: 11/153,225

(22) Filed: Jun. 15, 2005

(65) Prior Publication Data

US 2005/0278001 A1 Dec. 15, 2005

Related U.S. Application Data

(60) Provisional application No. 60/579,738, filed on Jun. 15, 2004.

(51) Int. Cl.
*A61N 1/00* (2006.01)
(52) U.S. Cl. ........................................................ 607/48
(58) Field of Classification Search .................. 607/2, 607/116–118, 48; 600/554, 557
See application file for complete search history.

(56) References Cited

U.S. PATENT DOCUMENTS

| 3,895,639 | A |   | 7/1975  | Rodler |
|-----------|---|---|---------|--------|
| 4,165,750 | A |   | 8/1979  | Aleev et al. |
| 4,324,253 | A |   | 4/1982  | Greene et al. |
| 4,408,609 | A |   | 10/1983 | Axelgaard |
| 4,503,863 | A | * | 3/1985  | Katims .................. 600/554 |
| 4,535,777 | A |   | 8/1985  | Castel |
| 4,640,286 | A |   | 2/1987  | Thomson |
| 4,803,988 | A |   | 2/1989  | Thomson |
| 4,848,347 | A |   | 7/1989  | Hall |
| 4,887,603 | A |   | 12/1989 | Morawetz et al. |
| 5,067,495 | A |   | 11/1991 | Brehm |
| 5,117,826 | A |   | 6/1992  | Bartelt et al. |

(Continued)

FOREIGN PATENT DOCUMENTS

WO       WO 99/41682 A2    8/1999

(Continued)

OTHER PUBLICATIONS

Web site print-out: *Cyclotec Pain Control Products*, Cyclotec AMT, 3 pages; http://www.cyclotecamt.com/pages2/products.htm.

(Continued)

*Primary Examiner*—George Manuel
(74) *Attorney, Agent, or Firm*—Ropes & Gray LLP

(57) ABSTRACT

A multi-mode electrical therapeutic stimulation system. The system includes circuitry for providing interferential stimulation, muscle stimulation, and pulsed DC stimulation with an automatic switchover of electrode configurations between types of interferential and muscle stimulation without the need to manually alter the positioning of the stimulation electrodes. In one embodiment, the system includes a simplified five-button user interface with pre-programmed user display screens and an operator interface through which a medical professional can alter settings, programs, and user configurations. In another embodiment, the system can also include a recharging/docking station having a built-in charging device and data port, providing for an automatic/periodic upload of compliance data from the device when the stimulator is placed in a modem cradle. A method for managing patient care associated with a patient-administered external medical device is also disclosed.

50 Claims, 56 Drawing Sheets

U.S. PATENT DOCUMENTS

| | | | |
|---|---|---|---|
| 5,161,530 A | 11/1992 | Gamble | |
| 5,300,096 A | 4/1994 | Hall et al. | |
| 5,350,414 A | 9/1994 | Kolen | |
| 5,397,338 A | 3/1995 | Grey et al. | |
| 5,512,057 A | 4/1996 | Reiss et al. | |
| 5,514,165 A | 5/1996 | Malaugh et al. | |
| 5,540,235 A * | 7/1996 | Wilson | 600/554 |
| 5,540,735 A | 7/1996 | Wingrove | |
| 5,562,718 A | 10/1996 | Palermo | |
| 5,732,401 A | 3/1998 | Conway | |
| 5,776,173 A | 7/1998 | Madsen, Jr. et al. | |
| 5,800,458 A | 9/1998 | Wingrove | |
| 5,817,138 A | 10/1998 | Suzuki | |
| 5,967,975 A | 10/1999 | Ridgeway | |
| 6,029,090 A | 2/2000 | Herbst | |
| 6,064,911 A | 5/2000 | Wingrove | |
| 6,113,552 A * | 9/2000 | Shimazu et al. | 600/557 |
| 6,324,432 B1 | 11/2001 | Rigaux et al. | |
| 6,393,328 B1 | 5/2002 | McGraw et al. | |
| 6,560,487 B1 | 5/2003 | McGraw et al. | |
| 6,564,103 B2 | 5/2003 | Fischer et al. | |
| 6,584,358 B2 | 6/2003 | Carter et al. | |
| 6,609,031 B1 | 8/2003 | Law et al. | |
| 6,612,984 B1 | 9/2003 | Kerr, II | |
| 6,662,051 B1 | 12/2003 | Eraker et al. | |
| 6,675,048 B2 | 1/2004 | McGraw et al. | |
| 6,684,106 B2 | 1/2004 | Herbst | |
| 6,701,189 B2 | 3/2004 | Fang et al. | |
| 6,727,814 B2 | 4/2004 | Saltzstein et al. | |
| 6,826,429 B2 | 11/2004 | Johnson et al. | |
| 6,988,005 B2 | 1/2006 | McGraw et al. | |
| 2001/0051787 A1 | 12/2001 | Haller et al. | |
| 2003/0036683 A1 | 2/2003 | Kehr et al. | |
| 2003/0074037 A1 | 4/2003 | Moore et al. | |

FOREIGN PATENT DOCUMENTS

| | | |
|---|---|---|
| WO | WO 99/41682 A3 | 10/1999 |
| WO | WO 00/36900 A2 | 6/2000 |
| WO | WO 00/36900 A3 | 10/2000 |
| WO | WO 03/008038 A1 | 1/2003 |
| WO | WO 2004/011087 A1 | 2/2004 |
| WO | WO 2004/012807 A2 | 2/2004 |
| WO | WO 2004/064915 A2 | 8/2004 |

OTHER PUBLICATIONS

Web site print-out: *Muscle Stimulator and TENS: Very different modalities*, RS Medical; 1 page; Copyright 2003.

Web site print-out: *RS-4i Sequential Stimulator*, RS Medical; 6 pages; Copyright 2003.

*Netwave*, Blue Sky Labs; 6 pages; Copyright 2003.

*501(k) Summary for netwave Interferential Stimulator*, Ryan Telmedicine, LLC; Copyright Jun. 12, 2003.

\* cited by examiner

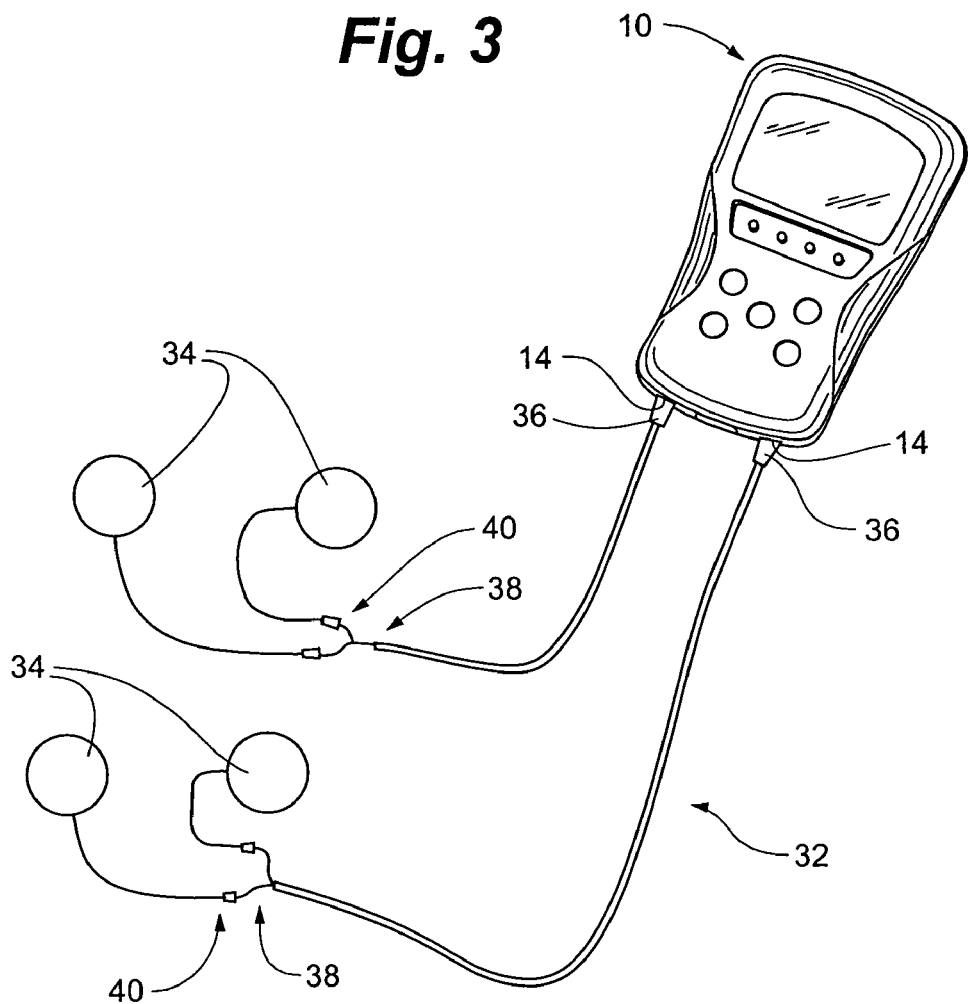

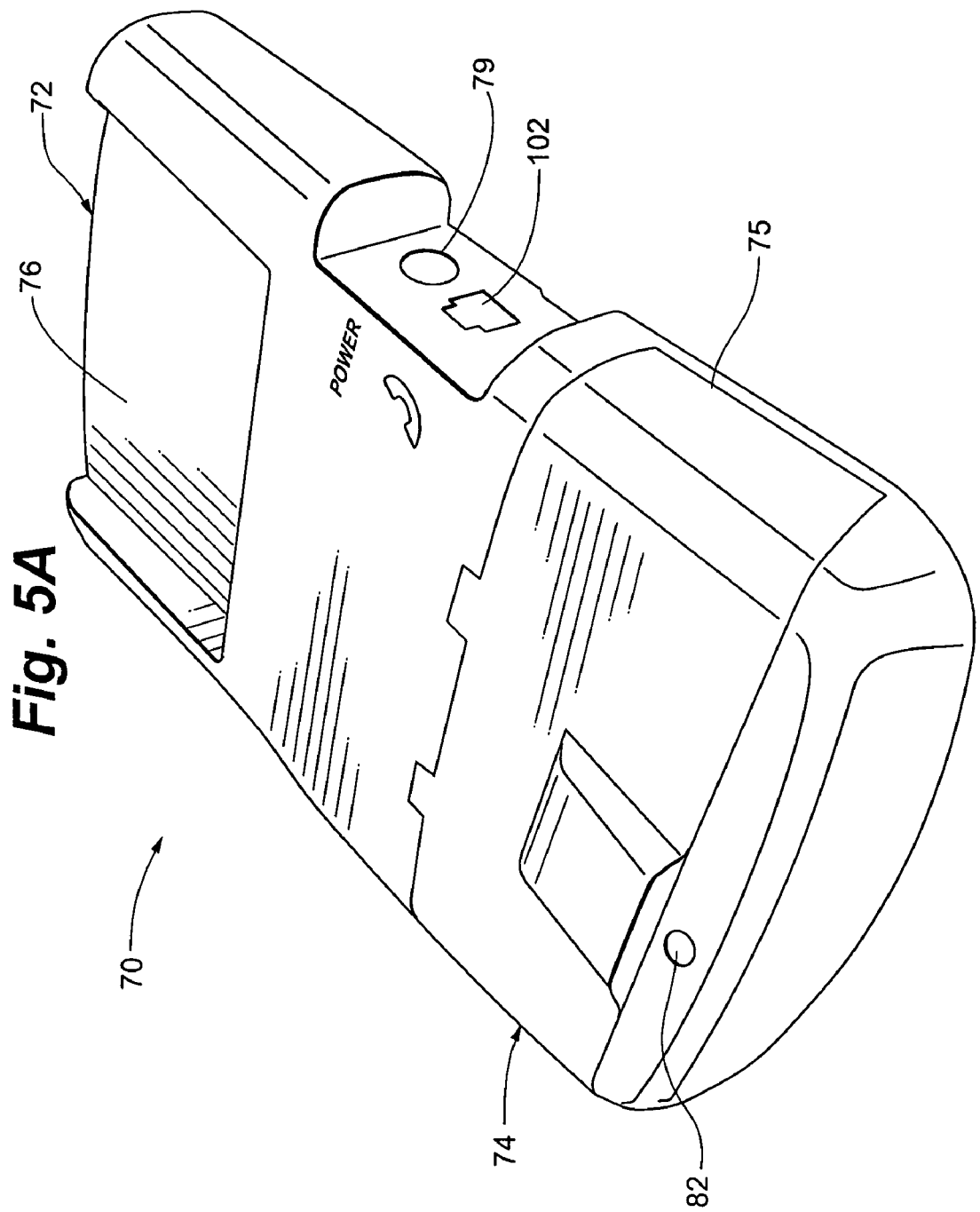

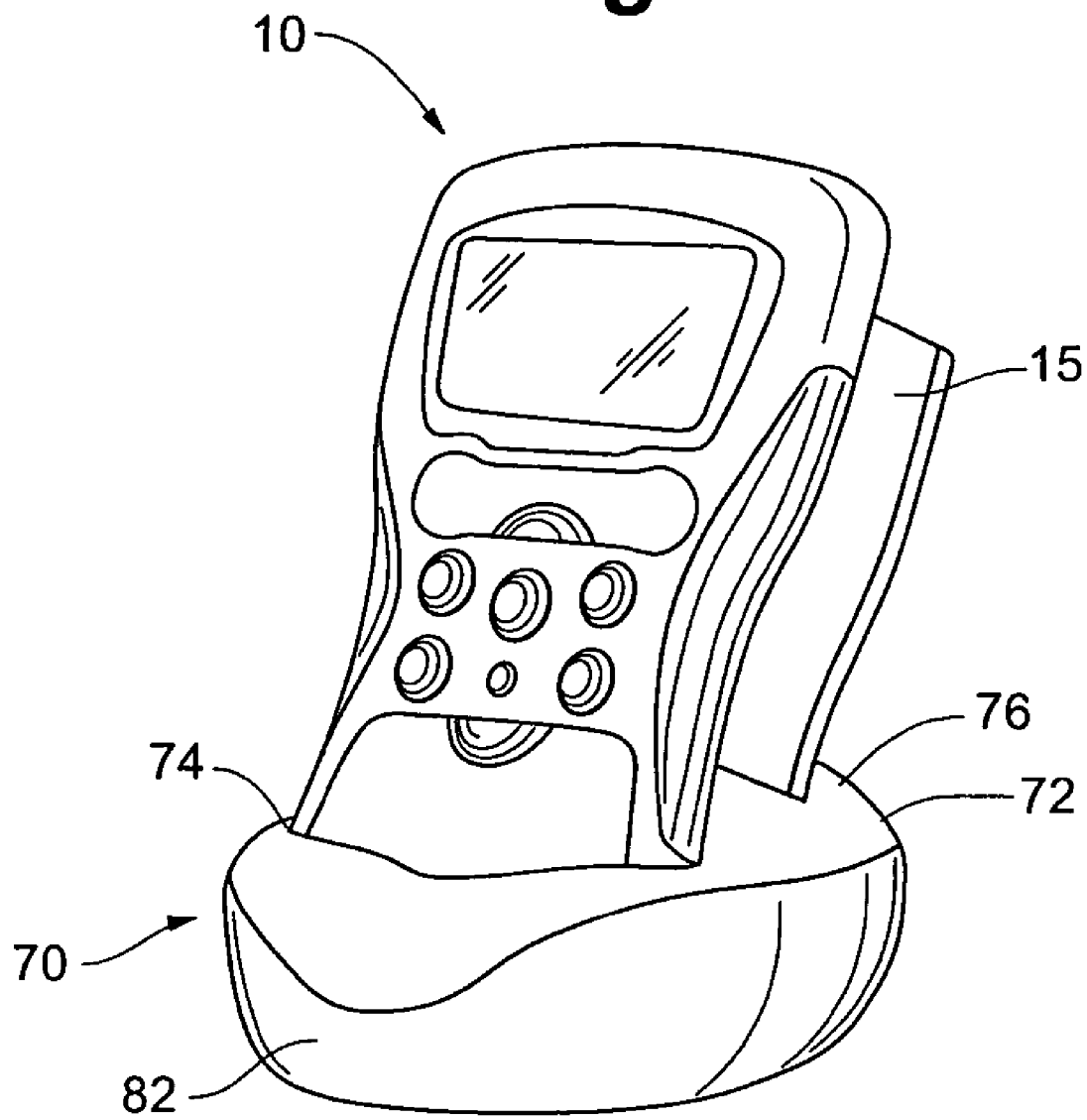

*Fig. 11*

| *Fig. 11A* | *Fig. 11B* | *Fig. 11C* | *Fig. 11D* |
|---|---|---|---|
| *Fig. 11E* | *Fig. 11F* | *Fig. 11G* | |

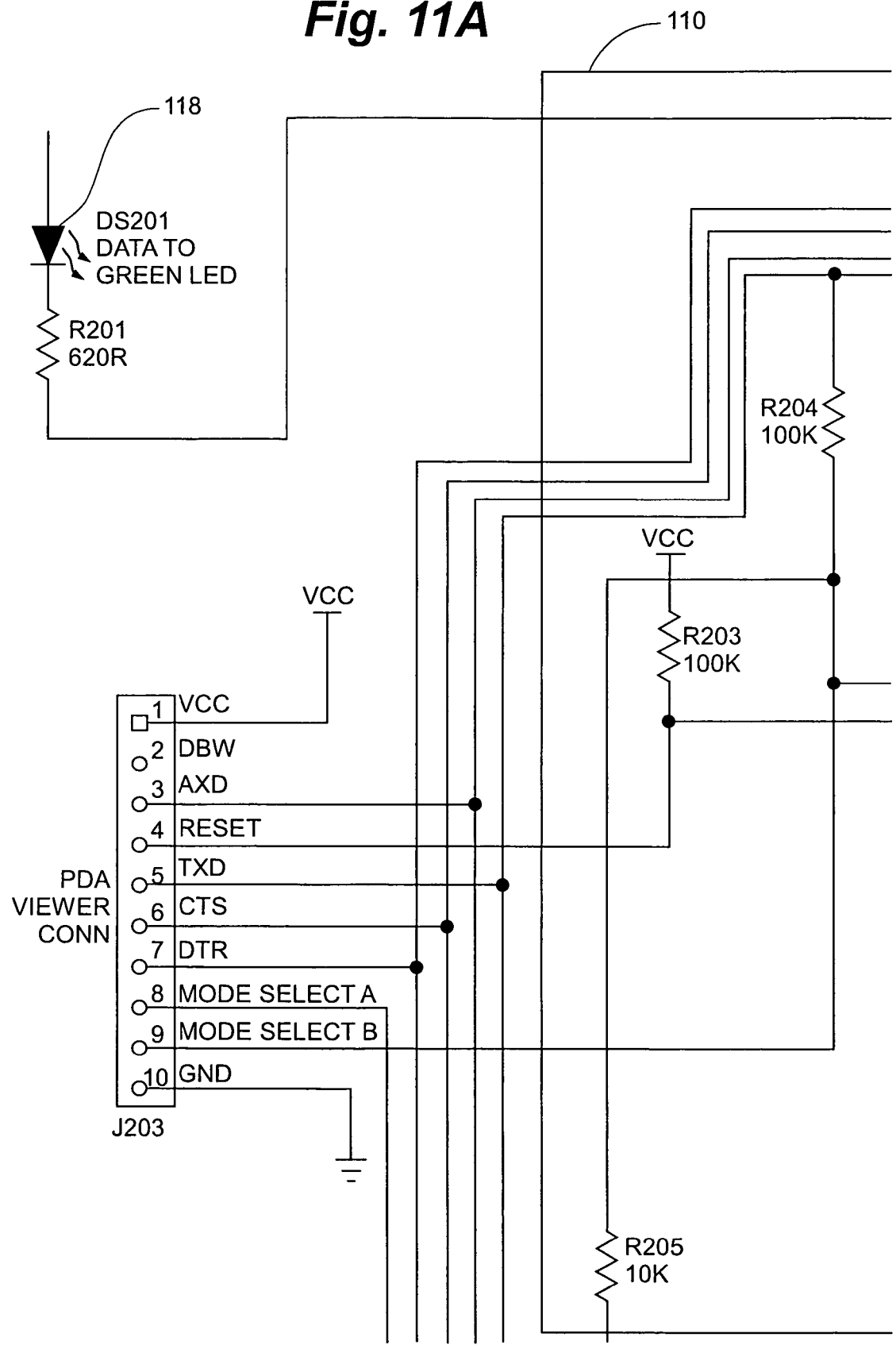

*Fig. 27*

| Fig. 27A |
|---|
| Fig. 27B |

*Fig. 28*

| Fig. 28A | Fig. 28B | Fig. 28C | Fig. 28D | Fig. 28E |
|---|---|---|---|---|
| Fig. 28F | Fig. 28G | Fig. 28H | Fig. 28J | Fig. 28K |

INTERFACE PATIENT SCREENS

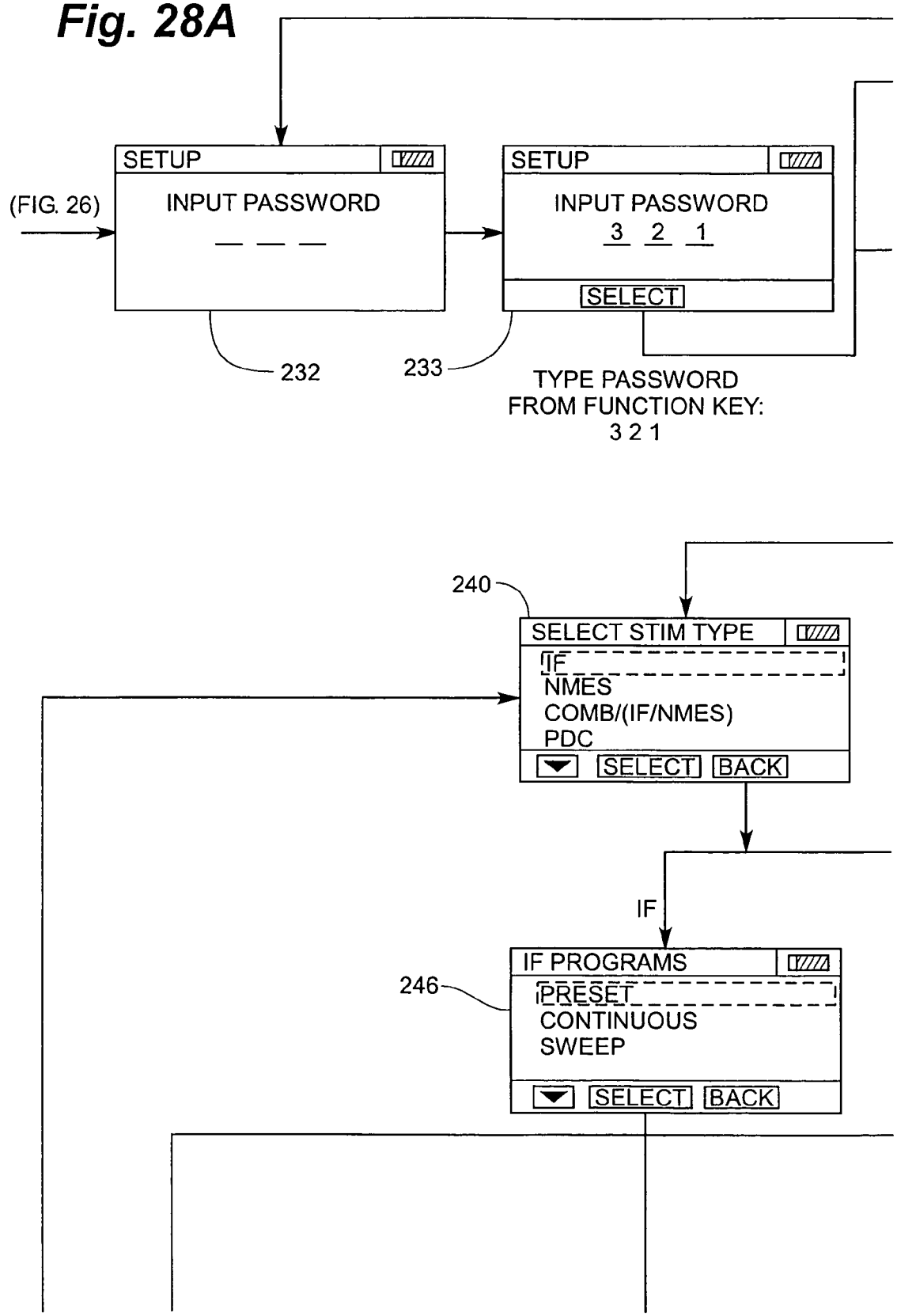

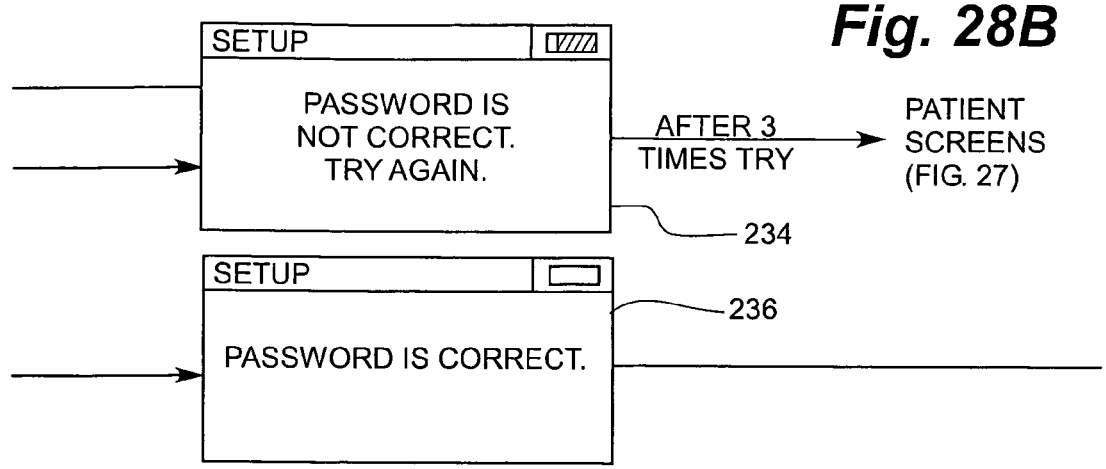
*Fig. 28B*
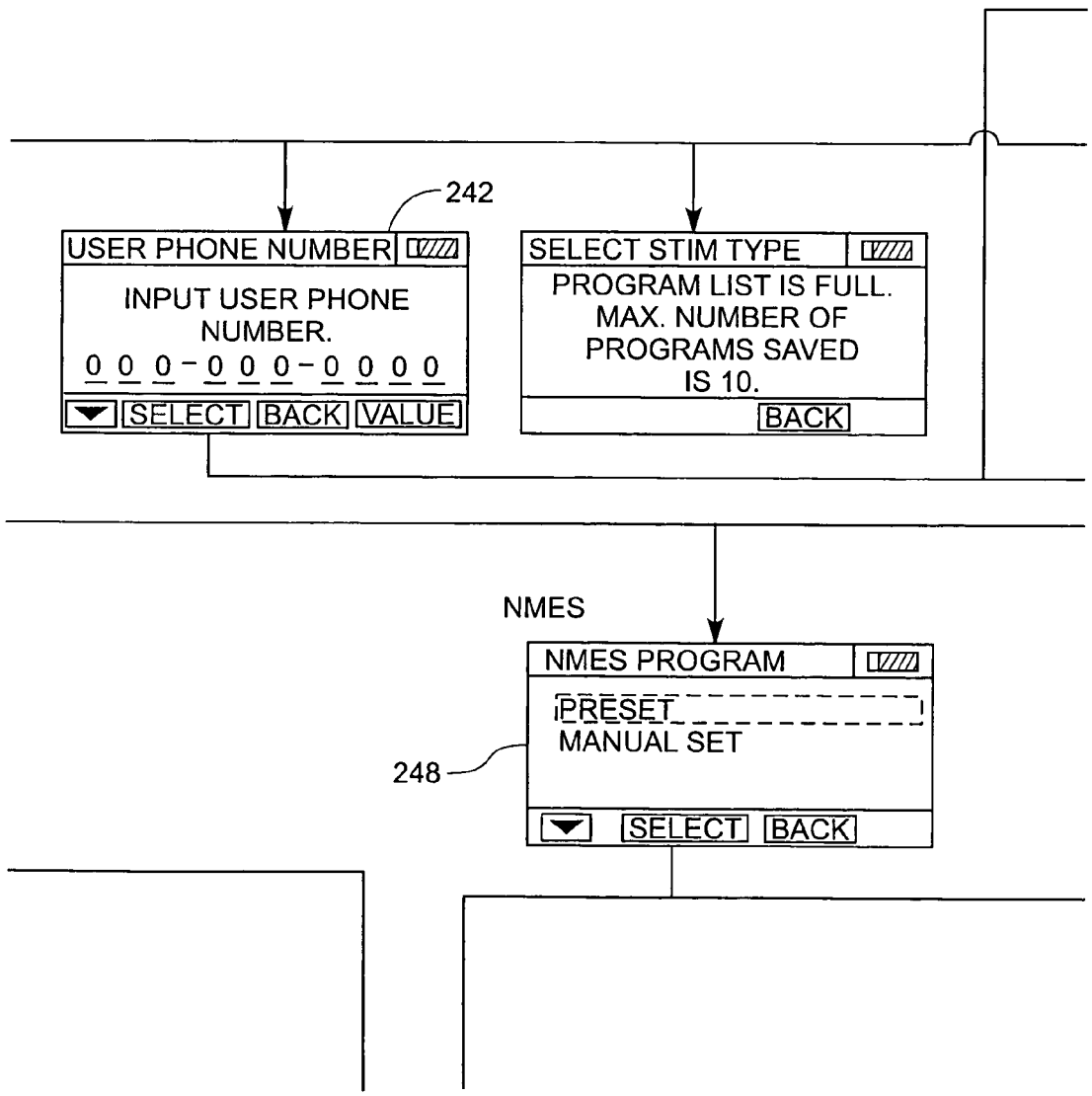

BACK TO SELECT STIM. TYPES SCREEN

Fig. 29

| Fig. 29A |
|---|
| Fig. 29B |
| Fig. 29C |

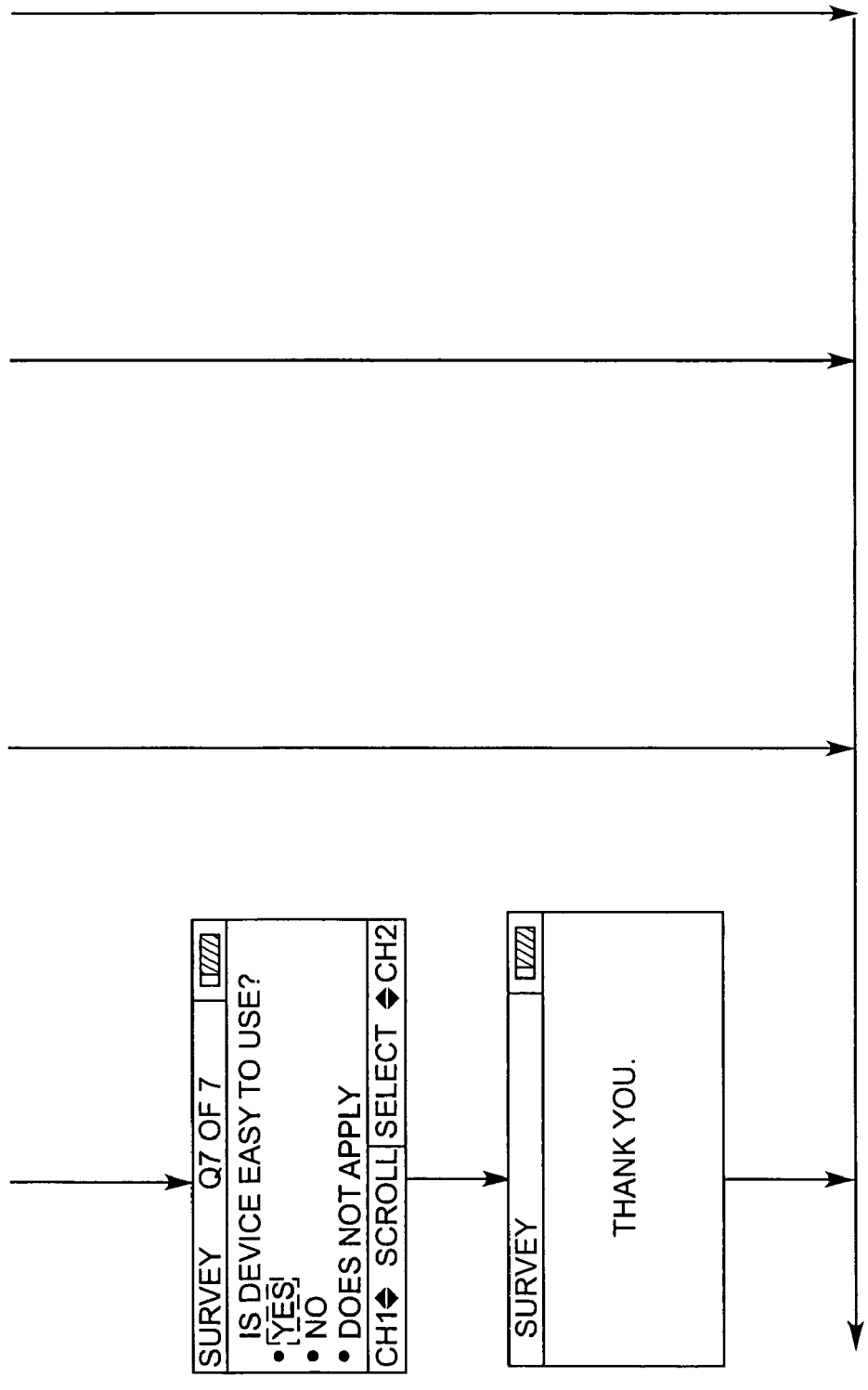

Fig. 31

Rehabilicare

Interferential Stimulator Patient Usage Report
IF 3Wave
Confidential Patient Information

Patient Information
Patient Name GARDIN, BART
Social Security 999-99-9999
Birth Date 19900101
Gender

Physician Information
Physician Name NORA CANTU
ICD9 Code
Prescription Date 19980101
Device Serial Number IF312345

Report Period
First Treatment Day 20040501
Last Treatment Day 20040504

Account Rep BROSNAHAN, SEAN
Total Treatment Days 3

Treatment Usage Information
Total Number of Treatments 30084
Total Treatment Minutes 20005

Average Treatment Session 0
Total Treatment minutes - Before noon AM 10002
Total Treatment Minutes - After Noon PM 10003

| Treatment Program | Total Use | Avg. Amp Ch1 | Peak Amp Ch1 | Avg Amp Ch2 | Peak Amp Ch2 | AM Time (Min) | PM Time (Min) |
|---|---|---|---|---|---|---|---|
| IF SWEEP | 10027 | 101 | 103 | 102 | 104 | 10009 | 10010 |
| IF PRESET-LOW BACK | 10028 | 111 | 113 | 112 | 114 | 10019 | 10020 |
| IF PRESET-NECK | 10029 | 121 | 123 | 122 | 124 | 10029 | 10030 |

Patient Survey Response
Ranking Scale Q1 Q2
1=Little Pain  10=Unbearable Pain
Q1-Ranked pain level at beginning of treatment period? AA
Q2-Ranked pain level at end of treatment period? BB Scale 1 = Yes 2 = No 99 = NA
Q3-Quality of sleep improved? DD
Q4-Use of device decreased medication use? CC
Q5-Less pain during daily activities? EE
Q6-Recommend device to reduce pain? FF
Q7-Device easy to use? GG

Patient Information
Patient Name  GARDIN, BART
Social Security    999-99-9999

Physician Information
Physician Name NORA CANTU
ICD9 Code

Total Daily Treatment Times by Treatment Type

| Day | P1 | P2 | P3 | P4 | P5 | P6 | P7 | P8 | P9 | P10 | Total |
|---|---|---|---|---|---|---|---|---|---|---|---|
| 20040405 | 1001 | 1002 | 1003 | 1004 | 1005 | 1006 | 1007 | 1008 | 1009 | 1010 | 10055 |
| 20040406 | 1011 | 1012 | 1013 | 1014 | 1015 | 1016 | 1017 | 1018 | 1019 | 1020 | 10155 |
| 20040407 | 1021 | 1022 | 1023 | 1024 | 1025 | 1026 | 1027 | 1028 | 1029 | 1030 | 10255 |
| 20040408 | 1031 | 1032 | 1033 | 1034 | 1035 | 1036 | 1037 | 1038 | 1039 | 1040 | 10355 |
| 20040409 | 1041 | 1042 | 1043 | 1044 | 1045 | 1046 | 1047 | 1048 | 1049 | 1050 | 10455 |
| 20040410 | 1051 | 1052 | 1053 | 1054 | 1055 | 1056 | 1057 | 1058 | 1059 | 1060 | 10555 |
| 20040411 | 1061 | 1062 | 1063 | 1064 | 1065 | 1066 | 1067 | 1068 | 1069 | 1070 | 10655 |
| 20040412 | 1071 | 1072 | 1073 | 1074 | 1075 | 1076 | 1077 | 1078 | 1079 | 1080 | 10755 |
| 20040413 | 1081 | 1082 | 1083 | 1084 | 1085 | 1086 | 1087 | 1088 | 1089 | 1090 | 10855 |
| 20040414 | 1091 | 1092 | 1093 | 1094 | 1095 | 1096 | 1097 | 1098 | 1099 | 1100 | 10955 |
| 20040415 | 1101 | 1102 | 1103 | 1104 | 1105 | 1106 | 1107 | 1108 | 1109 | 1110 | 11055 |
| 20040416 | 1111 | 1112 | 1113 | 1114 | 1115 | 1116 | 1117 | 1118 | 1119 | 1120 | 11155 |
| 20040417 | 1121 | 1122 | 1123 | 1124 | 1125 | 1126 | 1127 | 1128 | 1129 | 1130 | 11255 |
| 20040418 | 1131 | 1132 | 1133 | 1134 | 1135 | 1136 | 1137 | 1138 | 1139 | 1140 | 11355 |
| 20040419 | 1141 | 1142 | 1143 | 1144 | 1145 | 1146 | 1147 | 1148 | 1149 | 1150 | 11455 |
| 20040420 | 1151 | 1152 | 1153 | 1154 | 1155 | 1156 | 1157 | 1158 | 1159 | 1160 | 11555 |
| 20040421 | 1161 | 1162 | 1163 | 1164 | 1165 | 1166 | 1167 | 1168 | 1169 | 1170 | 11655 |
| 20040422 | 1171 | 1172 | 1173 | 1174 | 1175 | 1176 | 1177 | 1178 | 1179 | 1180 | 11755 |
| 20040423 | 1181 | 1182 | 1183 | 1184 | 1185 | 1186 | 1187 | 1188 | 1189 | 1190 | 11855 |
| 20040424 | 1191 | 1192 | 1193 | 1194 | 1195 | 1196 | 1197 | 1198 | 1199 | 1200 | 11955 |
| 20040425 | 1201 | 1202 | 1203 | 1204 | 1205 | 1206 | 1207 | 1208 | 1209 | 1210 | 12055 |
| 20040426 | 1211 | 1212 | 1213 | 1214 | 1215 | 1216 | 1217 | 1218 | 1219 | 1220 | 12155 |
| 20040427 | 1221 | 1222 | 1223 | 1224 | 1225 | 1226 | 1227 | 1228 | 1229 | 1230 | 12255 |
| 20040428 | 1231 | 1232 | 1233 | 1234 | 1235 | 1236 | 1237 | 1238 | 1239 | 1240 | 12355 |
| 20040429 | 1241 | 1242 | 1243 | 1244 | 1245 | 1246 | 1247 | 1248 | 1249 | 1250 | 12455 |
| 20040430 | 1251 | 1252 | 1253 | 1254 | 1255 | 1256 | 1257 | 1258 | 1259 | 1260 | 12555 |
| 20040501 | 1261 | 1262 | 1263 | 1264 | 1265 | 1266 | 1267 | 1268 | 1269 | 1270 | 12655 |
| 20040502 | 1271 | 1272 | 1273 | 1274 | 1275 | 1276 | 1277 | 1278 | 1279 | 1280 | 12755 |
| 20040503 | 1281 | 1282 | 1283 | 1284 | 1285 | 1286 | 1287 | 1288 | 1289 | 1290 | 12855 |
| 20040504 | 1291 | 1292 | 1293 | 1294 | 1295 | 1296 | 1297 | 1298 | 1299 | 1300 | 13955 |
| 20040505 | 1301 | 1302 | 1303 | 1304 | 1305 | 1306 | 1307 | 1308 | 1309 | 1310 | 13055 |
| 20040506 | 1311 | 1312 | 1313 | 1314 | 1315 | 1316 | 1317 | 1318 | 1319 | 1320 | 13155 |
| 20040507 | 1321 | 1322 | 1323 | 1324 | 1325 | 1326 | 1327 | 1328 | 1329 | 1330 | 13255 |
| 20040508 | 1331 | 1332 | 1333 | 1334 | 1335 | 1336 | 1337 | 1338 | 1339 | 1340 | 13355 |
| 20040509 | 1341 | 1342 | 1343 | 1344 | 1345 | 1346 | 1347 | 1348 | 1349 | 1350 | 13455 |
| 20040510 | 1351 | 1352 | 1353 | 1354 | 1355 | 1356 | 1357 | 1358 | 1359 | 1360 | 13555 |
| 20040511 | 1361 | 1362 | 1363 | 1364 | 1365 | 1366 | 1367 | 1368 | 1369 | 1370 | 13655 |
| 20040512 | 1371 | 1372 | 1373 | 1374 | 1375 | 1376 | 1377 | 1378 | 1379 | 1380 | 13755 |
| 20040513 | 1381 | 1382 | 1383 | 1384 | 1385 | 1386 | 1387 | 1388 | 1389 | 1390 | 13855 |
| 20040514 | 1391 | 1392 | 1393 | 1394 | 1395 | 1396 | 1397 | 1398 | 1399 | 1400 | 13955 |

Rehabilicare

| Field | Serial Number | Blank | Telephone | File Version | Type | Download Date | Nbr prgm recs | 1st Use Date |
|---|---|---|---|---|---|---|---|---|
| POS | 1-8 | 9-9 | 10-19 | 20-21 | 22-22 | 23-30 | 31-32 | 33-40 |
| Length | 8 | 1 | 10 | 2 | 1 | 8 | 2 | 8 |
| Format | sssssss | | xxxxxxxxxx | vs | f | yyyymmdd | xx | yyyymmdd |
| Sample | IF312345 | | 8135551212 | 10 | A | 20040811 | 03 | 20040701 |

Format B-Survey Response

| Field | Serial Number | Blank | Telephone | File Version | Type | Download Date | Survey Responses | Type |
|---|---|---|---|---|---|---|---|---|
| Pos | 1-8 | 9-9 | 10-19 | 20-21 | 22-22 | 23-30 | 31-44 | 45-45 |
| Length | 8 | 1 | 10 | 2 | 1 | 8 | 14 | 1 |
| Format | sssssss | | xxxxxxxxxx | vs | f | yyyymmdd | aabbccddeeffgg | f |
| Sample | IF312345 | | 8135551212 | 10 | B | 20040811 | 10 05050101010101 | B |

Format C-Program Average Settings

| Field | Serial Number | Blank | telephone | File Version | Type | Download Date | Program Slot | Program |
|---|---|---|---|---|---|---|---|---|
| POS | 1-8 | 9-9 | 10-19 | 20-21 | 22-22 | 23-30 | 31-32 | 33-34 |
| Length | 8 | 1 | 1 | 2 | 1 | 8 | 2 | 2 |
| Format | sssssss | | xxxxxxxxxx | vs | f | yyyymmdd | nn | pp |
| Sample | IF312345 | | 8135551212 | 10 | C | 20040811 | 01 01 | 00010 |

Format D-Daily Info

| Field | Serial Number | Blank | telephone | File Version | Type | Download Date | Capture Date | TT P1 |
|---|---|---|---|---|---|---|---|---|
| POS | 1-8 | 9-9 | 10-19 | 20-21 | 22-22 | 23-30 | 31-38 | 39-42 |
| Length | 8 | 1 | 1 | 2 | 1 | 8 | 8 | 4 |
| Format | sssssss | | xxxxxxxxxx | vs | f | yyyymmdd | yyyymmdd | tttt |
| Sample | IF312345 | | 8135551212 | 10 | D | 20040811 | 20040701 0000 | 0100 |

Fig. 33B

| Last Use Date | Period Start Date | TOT Treat | TT AM | TT PM | Type |
|---|---|---|---|---|---|
| 41-48 | 49-56 | 57-61 | 62-66 | 67-71 | 72-72 |
| 8 | 8 | 5 | 5 | 5 | 1 |
| yyyymmdd | yyyymmdd | ttttt | ttttt | ttttt | f |
| 20040805 | 20040701 | 00050 | 01200 | 01250 | A |

| Numb Treat | C1A AMP1 | C2A AMP1 | C1P AMP1 | C2P AMP1 | C1A AMP2 | C2A AMP2 | C1P AMP2 | C2P AMP2 | TT AM | T P |
|---|---|---|---|---|---|---|---|---|---|---|
| 35-39 | 40-42 | 43-45 | 46-48 | 49-51 | 52-54 | 55-57 | 58-60 | 61-63 | 64-68 | 69 |
| 5 | 3 | 3 | 3 | 3 | 3 | 3 | 3 | 3 | 5 | 5 |
| nnnnn | ttt | ttt | ttt | ttt | ttt | ttt | ttt | ttt | ttttt | tt |
| 00010 | 100 | 101 | 111 | 102 | 000 | 000 | 000 | 000 | 00300 | 004 |

| TT P2 | TT P3 | TT P4 | TT P5 | TT P6 | TT P7 | TT P8 | TT P9 | TT P10 | Type |
|---|---|---|---|---|---|---|---|---|---|
| 43-46 | 47-50 | 51-54 | 55-58 | 59-62 | 63-66 | 67-70 | 71-74 | 74-78 | 79-79 |
| 4 | 4 | 4 | 4 | 4 | 4 | 4 | 4 | 4 | 1 |
| tttt | tttt | tttt | tttt | tttt | tttt | tttt | tttt | tttt | f |
| 0000 | 0000 | 0000 | 0000 | 0000 | 0000 | 0000 | 0000 | 0000 | D |

Fig. 34

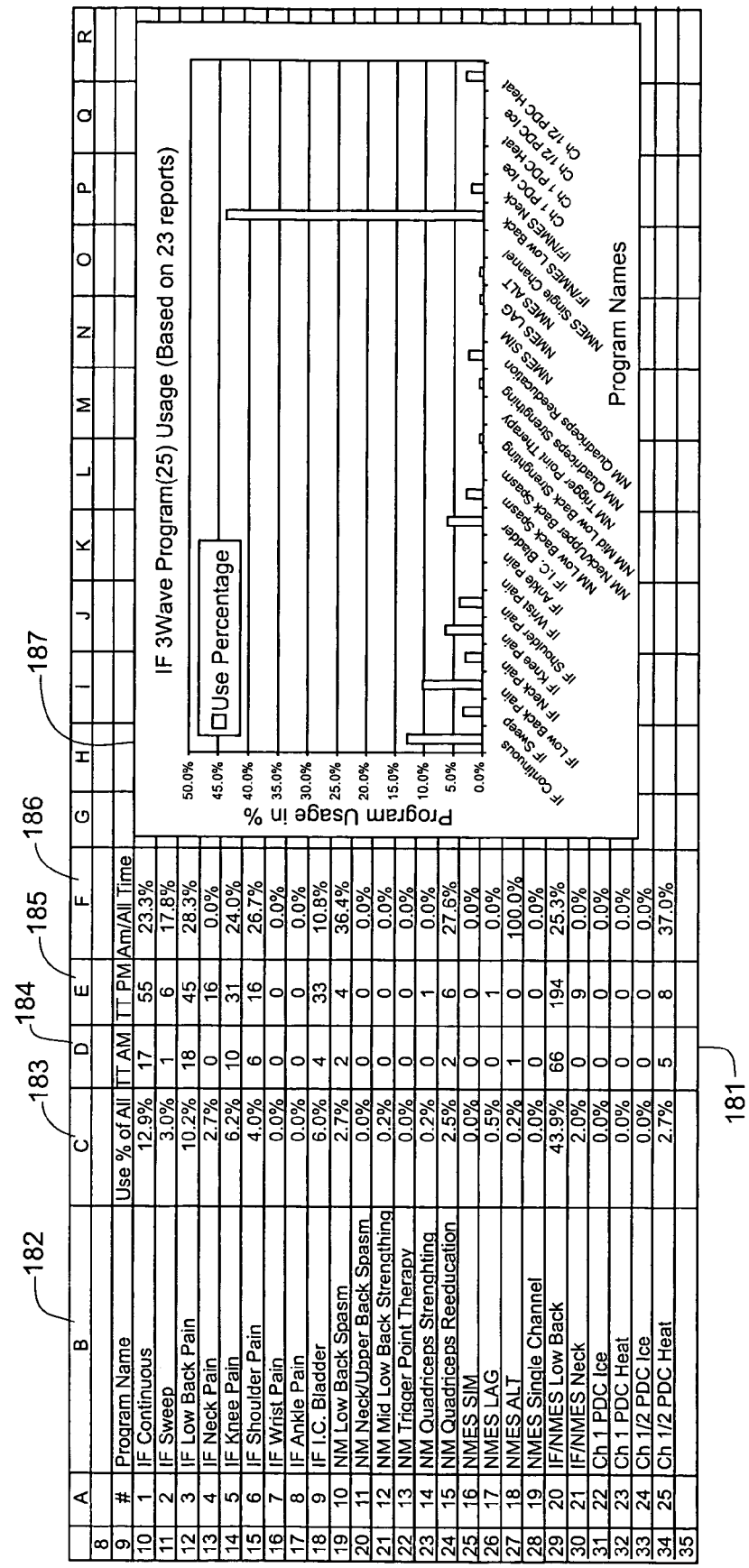

| | A | B | C | D | E | F |
|---|---|---|---|---|---|---|
| 8 | | | | | | |
| 9 | # | Program Name | Use % of All | TT AM | TT PM | Am/All Time |
| 10 | 1 | IF Continuous | 12.9% | 17 | 55 | 23.3% |
| 11 | 2 | IF Sweep | 3.0% | 1 | 6 | 17.8% |
| 12 | 3 | IF Low Back Pain | 10.2% | 18 | 45 | 28.3% |
| 13 | 4 | IF Neck Pain | 2.7% | 0 | 16 | 0.0% |
| 14 | 5 | IF Knee Pain | 6.2% | 10 | 31 | 24.0% |
| 15 | 6 | IF Shoulder Pain | 4.0% | 6 | 16 | 26.7% |
| 16 | 7 | IF Wrist Pain | 0.0% | 0 | 0 | 0.0% |
| 17 | 8 | IF Ankle Pain | 0.0% | 0 | 0 | 0.0% |
| 18 | 9 | IF I.C. Bladder | 6.0% | 4 | 33 | 10.8% |
| 19 | 10 | NM Low Back Spasm | 2.7% | 2 | 4 | 36.4% |
| 20 | 11 | NM Neck/Upper Back Spasm | 0.0% | 0 | 0 | 0.0% |
| 21 | 12 | NM Mid Low Back Strengthing | 0.2% | 0 | 0 | 0.0% |
| 22 | 13 | NM Trigger Point Therapy | 0.0% | 0 | 0 | 0.0% |
| 23 | 14 | NM Quadriceps Strenghting | 0.2% | 0 | 1 | 0.0% |
| 24 | 15 | NM Quadriceps Reeducation | 2.5% | 2 | 6 | 27.6% |
| 25 | 16 | NMES SIM | 0.0% | 0 | 0 | 0.0% |
| 26 | 17 | NMES LAG | 0.5% | 0 | 1 | 0.0% |
| 27 | 18 | NMES ALT | 0.2% | 1 | 0 | 100.0% |
| 28 | 19 | NMES Single Channel | 0.0% | 0 | 0 | 0.0% |
| 29 | 20 | IF/NMES Low Back | 43.9% | 66 | 194 | 25.3% |
| 30 | 21 | IF/NMES Neck | 2.0% | 0 | 9 | 0.0% |
| 31 | 22 | Ch 1 PDC Ice | 0.0% | 0 | 0 | 0.0% |
| 32 | 23 | Ch 1 PDC Heat | 0.0% | 0 | 0 | 0.0% |
| 33 | 24 | Ch 1/2 PDC Ice | 0.0% | 0 | 0 | 0.0% |
| 34 | 25 | Ch 1/2 PDC Heat | 2.7% | 5 | 8 | 37.0% |

Fig. 35

| ANALYSIS DATE: 5/18/05 2:11 PM | 132 MIN | NUMBER OF RECORDS | 25 |
|---|---|---|---|
| AVG AM USE/DEVICE | 132 MIN | | |
| AVG PM USE/DEVICE | 426 MIN | | |
| AVG NUM OF PROG/RECORD | 3.3 SETS | | |
| CH 1 AVG IF SET | 38 % | CH1 MAX IF SET | 100 % |
| CH 2 AVG IF SET | 38 % | CH2 MAX IF SET | 100 % |
| CH1 AVG NMES SET | 13 % | CH1 MAX NMES SET | 35 % |
| CH2 AVG NMES SET | 9 % | CH2 MAX NMES SET | 20 % |
| CH1 AVG COMBO SET | 45 % | CH1 MAX COMBO SET | 88 % |
| CH2 AVG COMBO SET | 45 % | CH2 MAX COMBO SET | 87 % |
| CH1 AVG PDC SET | 22 % | CH1 MAX PDC SET | 35 % |
| CH2 AVG PDC SET | % | CH2 MAX PDC SET | % |
| AVG PAIN REDUCE | 0.9 LEVEL | | |
| YES FOR EASY TO USE | 100 % | AVG USE TIMES ALL PROGRAMS | 16 TIMES |
| YES FOR SLEEP IMPROVED | 58 % | | |
| YES FOR REDUCE MEDICATION | 50 % | | |
| YES FOR PAIN DURING ACTIVITIES | 63 % | | |
| YES FOR REDUCE PAIN | 88 % | | |
| % OF PATIENT IMPROVED | 42 % | | |

INTERFERENTIAL AND NEUROMUSCULAR ELECTRICAL STIMULATION SYSTEM AND APPARATUS

RELATED APPLICATION

This application claims priority to U.S. Provisional Patent Application Ser. No. 60/579,738, filed Jun. 15, 2004, which is incorporated herein by reference in its entirety.

FIELD OF THE INVENTION

The present invention relates generally to electrical stimulation systems for treatment of pain and rehabilitation of muscles. More particularly, the present inventions relates to a handheld electrical therapeutic stimulator that is simpler and easier to use while providing expanded functionality.

BACKGROUND OF THE INVENTION

Electrical therapeutic stimulators are well known. For the treatment of pain, there are devices such as a transdermal electrical nerve stimulator (TENS) unit or interferential stimulators that use an interferential stimulation set up by the beating of pulses applied at two different frequencies. For muscle stimulation for rehabilitation or training, there are devices that use biphasic square wave pulses, a pulsed direct current stimulation or galvanic current stimulation. These devices can also be used for pain management and edema reduction. Originally, electrical therapeutic stimulators were tabletop sized devices. More recently, smaller handheld devices have been developed. Today, some devices are small enough to be applied like a bandage to a desired area of the body to be stimulated. Devices have also been designed to deliver treatment modalities with different waveforms packaged into a single device.

It is common practice for therapists, physicians, athletes, and other individuals to utilize various treatment modalities and electrical therapy devices to promote muscle training, conditioning, and rehabilitation. With muscle stimulation and nerve stimulation, a device is programmed to output various levels of electrical pulses. The waveforms, frequency, duration, pulse width, intensity, and output modalities of the output signal control the directed treatment goals.

With regard to muscle stimulation, there are a myriad of uses for these electro-stimulation devices. Treatment categories can generally be divided between muscle fitness, muscle aesthetic, sport training, muscle rehabilitation, and vascular therapy. Each category is directed to a different stimulation goal. With muscle fitness, the goal is generally to restore, improve, or maintain a good physical condition by building muscle, muscle tone, volume, trophism, metabolism, and the like. With muscle aesthetic goals, a stimulator is often utilized on muscles in order to shape, firm, refine, increase elasticity, and increase caloric expenditure. Sports-minded individuals may use a device to increase muscular endurance and strength, increase blood flow to promote active recovery, and the like. When focus is on muscle rehabilitation, muscular stimulation is needed to restore or otherwise redevelop a convalescent muscle. Under the vascular category of treatment programs, the goal is to improve blood circulation in the stimulated area to promote healing and minimize circulatory problems, fatigue, lack of oxygenation, swelling, and other related problems.

Regardless of the unique goal-dependent outputs of the device, electro-stimulation for muscle stimulation works under a principle of voluntary muscle contraction. When individuals contract a muscle, the brain sends the information to the muscle via the motor nerve. With electro-stimulation, a suitable electric current acts directly on the nerve by means of electrical impulses that reproduce the natural physiological phenomenon. These electrical impulses are applied to the user through attached electrodes. The electrodes are typically adhesively attached to the person or person's clothing. With electro-stimulation a patient or user can achieve intensive muscular work without mental or cardiac fatigue, thus reducing joint and tendon constraints. U.S. Pat. No. 6,324,432, commonly assigned with the present application to Compex SA, discloses an electrical neuromuscular stimulator for measuring muscle responses to electrical stimulation pulses, and U.S. patent application Publication No. 2003/0074037 discloses an electrical nerve stimulation device. U.S. Pat. No. 6,324,432 and U.S. patent application Publication No. 2003/0074037 are incorporated herein by reference in their entireties.

However, conventional electro-stimulation devices, while useful in achieving intensive muscular work for a target or generalized muscle set, are not capable of self-adjusting for various muscle groups. Conventional devices are also not capable of automatically adjusting for various users; even though two patients may be seeking the same general therapeutic or training effects, each may be at a different fitness or recovery stage. Further, conventional electro-stimulation devices are not generally able to self-adjust for detected physiological traits of a particular user.

In pain management applications, electro-stimulation devices are used primarily to alleviate pain and discomfort, including chronic intractable pain, post surgical pain, and post traumatic pain, and to increase blood flow. Increasing blood flow, for example, fosters healing. TENS, microcurrent, and interferential electrotherapy stimulation techniques have been used successfully for the symptomatic relief and management of chronic intractable pain for many years. In general, TENS or micro current electrical nerve stimulation controls pain of peripheral origin by providing a counter stimulation that interferes with the painful sensations.

In one application according to gate control theory, small electrical impulses are sent through the skin into a painful area. These electrical impulses are harmless but reach the nerves and cause a mild tingling sensation. Gate control theory states that as pain impulses travel through a nerve to the spinal cord and brain, the pain impulses can be altered or modified at certain points along the route. Pain signals are carried to the brain via small diameter, slow conducting nerve fibers. This transmission can be blocked by stimulating larger diameter, fast conducting nerve fibers. The signals along the fast conducting nerve fibers normally reach the brain before those traveling along the slow conducting nerve fibers. If the larger fibers are stimulated without much activity of the smaller pain fibers, the "gate" is closed and pain is lessened and/or blocked.

Interferential (IF) stimulation is used for symptomatic relief and management of chronic intractable pain and for increasing blood flow. IF stimulation is also used as an adjunctive treatment in management of post surgical and post traumatic pain. In this therapeutic treatment, two or more electrical signals having varying frequencies and/or phases are induced in a patient's tissue, where the signals combine, or interfere, to form a modulated signal that is effective for pain treatment and management.

Conventional stimulation devices, however, frequently require application and supervision by a trained medical professional to prevent muscle over-stimulation, fatigue, or, in extreme situations, injury. As these electronic devices have improved and been reduced in size, there has been a trend toward providing ever-increasing flexibility and greater programming options for such devices. U.S. Pat. No. 6,674,048 is one example of such a handheld electro-medical device. The handheld device features a single LCD touch-sensitive screen on which a wide variety of programming control and directions are provided to both the clinician and the user.

The need remains, however, for an electrical muscle stimulation device and corresponding electrode system that substantially addresses the innate drawbacks of conventional devices and systems. For example, while the enhanced functionality and features of handheld electrical therapeutic stimulators offer more treatment options, the complexity of these devices can offset the effectiveness of this enhanced functionality, particularly in older patient populations. Accordingly, it would be desirable to provide for a handheld electrical therapeutic stimulator that is simpler and easier to use while providing expanded functionality.

SUMMARY OF THE INVENTION

The present invention is a handheld electrical therapeutic stimulation system that is easier to use while providing expanded functionality. Preferably, the stimulation system includes circuitry for providing both muscular stimulation and interferential stimulation for pain management with an automatic switchover of electrode configurations between the two types of stimulation without the need to manually alter the positioning of the stimulation electrodes. In one embodiment, a simplified five-button user interface with pre-programmed user display screens is provided with a protective cover over additional buttons that a medical professional operator may use to alter settings and the user display screen flow. An access code can be programmed and required in order to access these and other advanced control features. In another embodiment, the stimulator is provided with a recharging/docking station that includes a built-in data port. This embodiment provides for an automatic/periodic upload of compliance data from the device when the stimulator is placed in a modem cradle.

In one embodiment, a handheld electrical therapeutic stimulation system operates as a dual mode stimulation system and includes a user interface system. The user interface system has a first access level for a user who is a patient and a second access level for an operator. The operator may be a doctor, nurse, therapist, or other medical professional. The user interface system comprises an input portion and an output portion adapted to accept a first set of data and information from a user and a second set of data and information from an operator and to provide first and second levels of treatment data to users and operators, respectively.

The invention is also directed to a method for managing patient care associated with a patient-administered external medical device. An external medical device can be provided to a patient for patient self-administration of a prescribed treatment regimen and tracked by at least one characteristic associated with the patient and at least one characteristic associated with the medical device. The external medical device can then transmit electronic data, which is received by a database. In one embodiment, the data transmission comprises quantitative medical device usage data, qualitative patient treatment data, or both, and is matched to a patient file by the characteristic associated with the patient and the characteristic associated with the medical device. One or more reports can then be generated, comprising at least a portion of the electronic data transmission, and incorporated into the patient file.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is a view of the stimulator of FIG. 1 with electrodes.

FIG. 5A is a view of a docking station according to one embodiment of the invention.

FIG. 6 is a view of a stimulator and docking station according to one embodiment of the invention.

FIG. 31 is a report according to one embodiment of the invention.

FIG. 32 is a report according to one embodiment of the invention.

FIG. 34 is a report including a graph according to one embodiment of the invention.

FIG. 35 is a report according to one embodiment of the invention.

Figure 1:
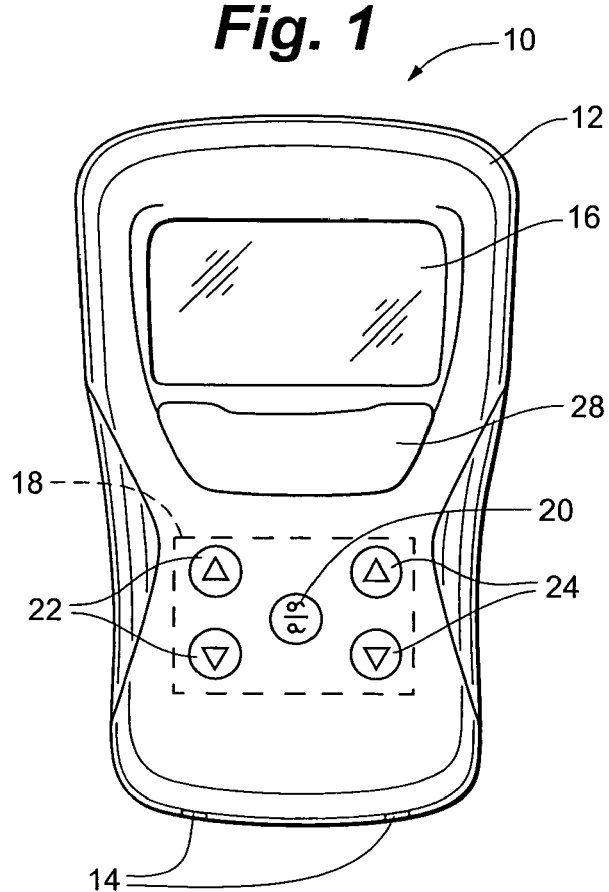
FIG. 1 is a view of a stimulator according to one embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The interferential, pulsed DC, and neuromuscular electrical stimulation system and apparatus of the invention provide electrical stimulation therapy and treatment via a convenient and user-friendly device and dual mode interface. The stimulation system can be of use treating, for example, acute and chronic pain, edema, tight musculature, muscle spasms, muscular weakness due to disuse atrophy, and other muscle symptoms and disorders known to those skilled in the art. The invention can be more readily understood by reference to FIGS. 1-37 and the following description. While the invention is not necessarily limited to a combined interferential, pulsed DC, and neuromuscular electrical stimulation application, the invention will be better appreciated using a discussion of exemplary embodiments in specific contexts.

Herein throughout, the term "user" will be used to refer generally to patients or persons receiving electro-therapy and electrostimulation treatments. The term "operator" will be used to refer generally to doctors, nurses, therapists, clinicians, and other medical and healthcare professionals, as well supervisory personnel and those having specialized or particular training relating to the use of electro-therapy devices. A dual mode muscle stimulation system, therefore, can include a first user mode interface and a second operator mode interface in one preferred embodiment. In all cases, however, reference should be made to the particular context surrounding the use of the term in order to ascertain the intended meaning. Terms used in the appended claims are to be given their ordinary meaning.

The interferential and neuromuscular electrical stimulation system generally comprises a stimulator; at least one lead wire assembly; at least one electrode; and a power source. In one embodiment, the power source comprises at least one battery, and preferably a rechargeable battery, wherein the electrical stimulation system further comprises a battery charger and modem cradle device. The system components can be packaged together in a convenient carrying case that may also include accessories, a user manual, and other relevant information.

Referring to FIGS. 1-4, one embodiment of a stimulator 10 includes a case 12 housing an electrostimulation device. Case 12 is preferably an injection-molded plastic or similar material, ergonomically designed and sized so as to be comfortably held by a user. In one embodiment, case 12 is adapted to be removably held by a belt clip, holster, or other in-use mounting apparatus. Case 12 can also be adapted to removably mate with a battery charger and modem cradle device (refer to FIGS. 5-7A and 7B and the description below) and includes at least one output channel interface 14 operable to electrically couple a cable, electrode, or other treatment applicator to stimulator 10. In one embodiment, case 12 includes two output channel interfaces 14, each interface 14 associated with a set of electrodes or other treatment applicators.

User interface features of stimulator 10 include an output portion 16 and an input portion 18. Output portion 16 can be a display screen and is preferably a liquid crystal display (LCD) of sufficient size and orientation for a user to easily view alphanumeric and ASCII characters, graphics, and symbols used to set up and select various treatment options and otherwise convey information to a user as part of a set of pre-programmed user display screens. Preferably, output portion 16 is not a touch-sensitive screen and is not used for input, although it can be in other embodiments of the invention. Input portion 16 can comprise several individual keys, a keypad, push buttons, switches, or other similar input means by which a user can easily set up, scroll through, and select from various options on display screen (output portion) 16. Preferably, input portion 18 is separate from display screen 16. As depicted in FIG. 1, input portion 18 comprises a five-button user interface that includes a power button 20 and two sets of scroll buttons 22 and 24. In one embodiment, set 22 is associated with a first output channel and set 24 is associated with a second output channel, although the sets of buttons 22 and 24 can be used for entering and selecting non-channel specific information as appropriate to a program or feature of stimulator 10.

The options available to a particular user or operator, or to a group of users or operators, via input portion 18 and output portion 16 can vary in one embodiment of the invention. In particular, to enhance the ease of use of stimulator 10 by both users and operators, a user interface and an operator interface will separate functional features used by a health care professional operator from those used by a patient user to create a dual mode stimulation system. Functional features used by an operator to set up user treatment programs can require entering setup functions independent of a user interface and isolated by separate operation keys, a required password-type access code, and methods of entry in one embodiment.

Figure 2:
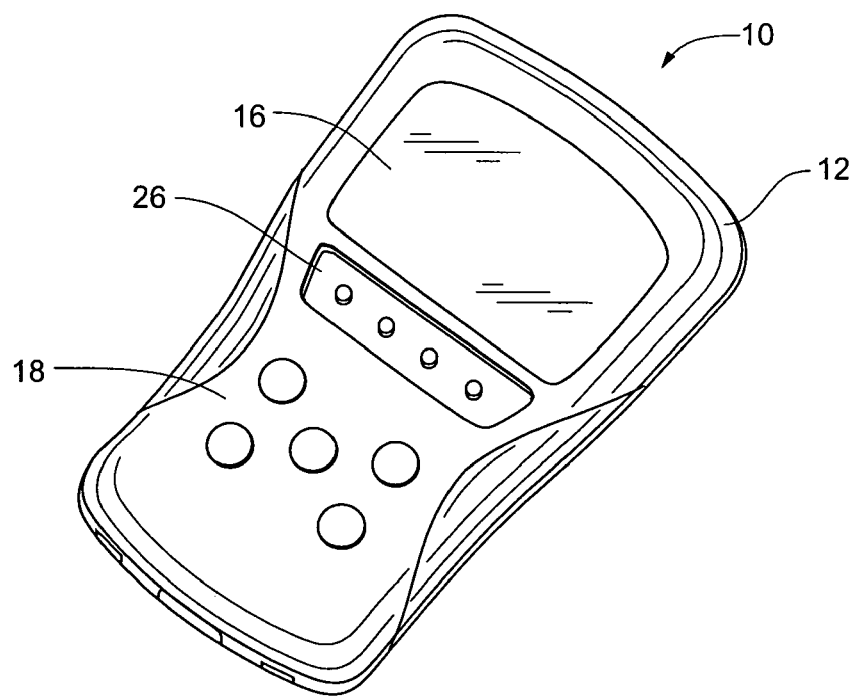
FIG. 2 is another view of the stimulator of FIG. 1.

As shown in FIG. 2, an operator interface 26 of operation keys, switches, or buttons can be made available to operators, including clinicians and other health care professionals, to set up user treatment programs. Operator interface 26 may make use of input portion 18 and user methods of accessing and inputting programs and other information; operator interface 26, however, is preferably independent of and isolated from a patient's input portion 18 in one embodiment. In a preferred embodiment as shown in FIG. 1, operator interface 26 of FIG. 2 is isolated from user access by a concealing means 28, for example a flip-up, securable, and/or removable cover, lid, case, screen, or the like, and requires entry of an access code to enable operator functions. Alternatively, operator interface 26 can be incorporated as part of a touch screen capability of output portion 16 that is isolated from the user portion of output portion 16, or operator interface 26 can be electrically or mechanically disabled by an operator prior to providing a user with stimulator 10.

In another embodiment, a particular set of options and other information can be made available only to operators via input portion 18 and output portion 16. For example, selections and other information can be displayed on output portion 16, associated with a particular key or button of input portion 18 in order to make a selection or enter information. The selections and information displayed on output portion 16 in this embodiment can be made available only to operators via passwords and access codes, entry methods, and/or operator screens described in more detail below. Some or all of these selections, options, or information can also be made available to a user or a group of users at an operator's discretion in one embodiment.

Stimulator case 12 includes an internal power source storage portion. In one embodiment, the power source comprises a rechargeable battery power source and is removably coupled to case 12 in a location that is secure yet accessible for maintenance and replacement, such as on a rear portion of case 12. In one embodiment, a battery power source is removably secured within a compartment by an externally accessible operator access panel. The battery power source preferably comprises a rechargeable Lithium ion polymer battery having a nominal voltage of about 3.7 volts and nominal capacity of about 3000 milliAmp-hours (mAh), although other power sources and battery types can also be used.

A lead wire assembly 32 shown in FIG. 3 removably couples the output of stimulator 10 to applicator electrodes 34 for each output channel. A proximate end of each lead wire assembly 32 electrically interfaces with stimulator 10 via output channel interfaces 14, preferably by a keyed friction force mechanically shielded connector 36 in one embodiment. Other interface connectors can also be used in other embodiments of the invention. The particular lead wire assembly and electrodes used with stimulator 10 should comply with applicable U.S. domestic, European, or other regional regulatory requirements. Electrodes 34 selected for use with stimulator 10 and lead wire assemblies 32 can be configured for an intended and specific clinical application or use. Generally, two active/passive sets of electrodes 34 will be used with stimulator 10 having two output channels, and each electrode set will comprise a connector assembly 38 compatible with distal lead wire assembly 40 in one embodiment. In an alternate embodiment, a radio frequency (RF) communication channel link or other wireless connection may be provided in addition to or in place of one or more connection paths to electrodes 34.

Figure 4A:
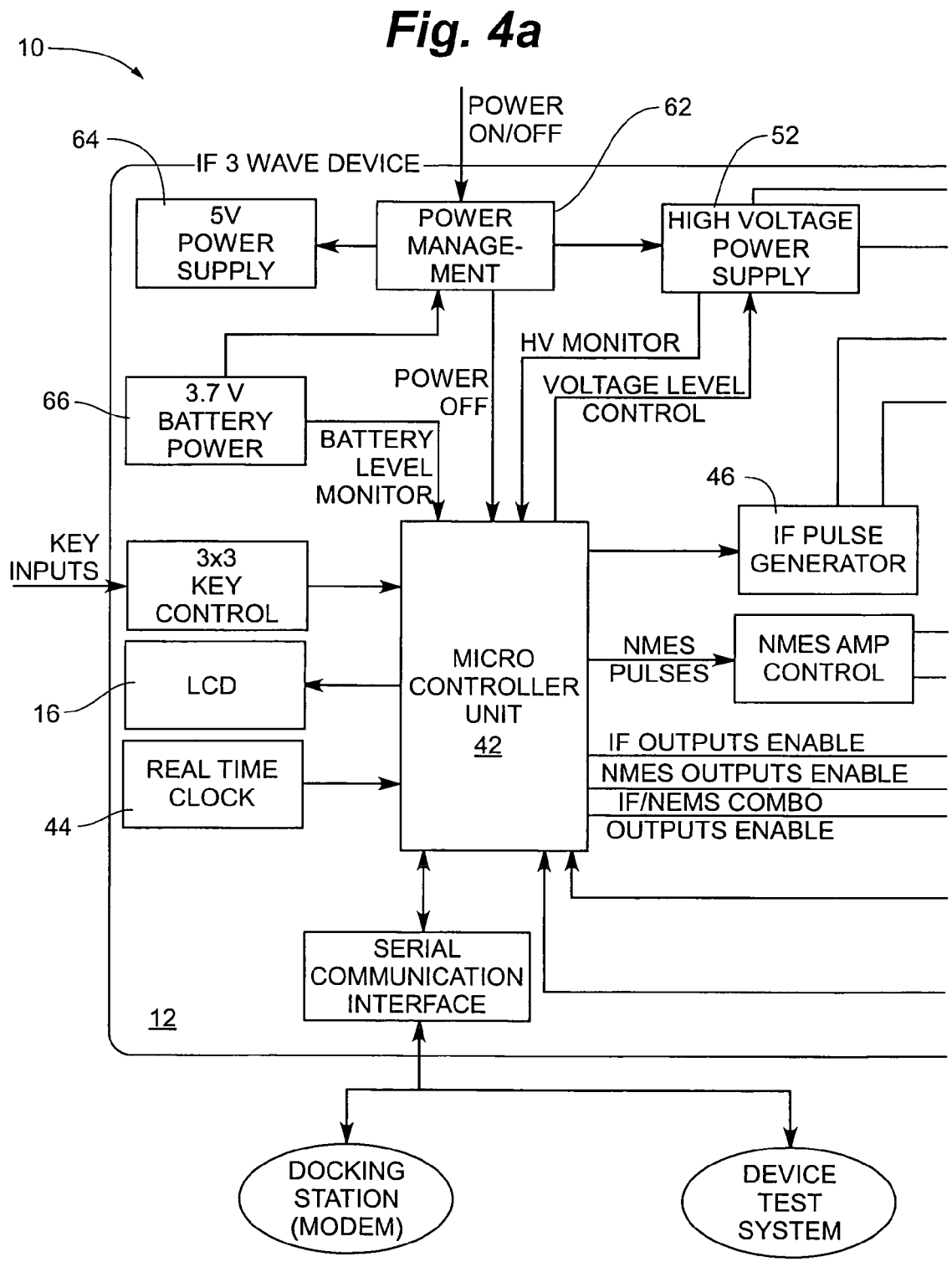
FIG. 4 is a block diagram of the stimulator of FIG. 1.
Figure 4B:
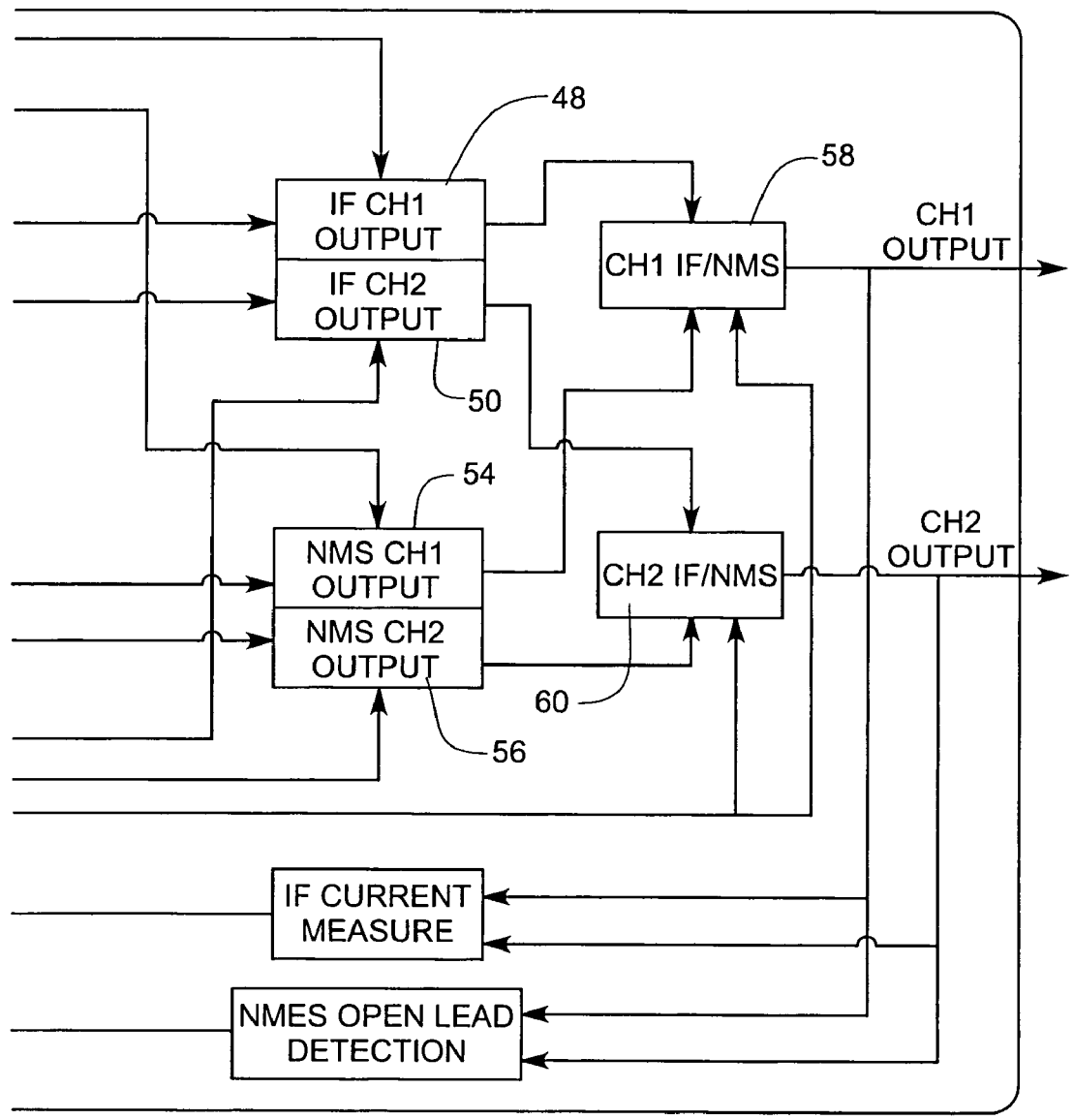

Referring to FIG. 4, stimulator 10 can be a microprocessor-controlled dual channel interferential electro-stimulator with neuromuscular and pulse direct current stimulation capabilities. In one embodiment, the microprocessor comprises a microcontroller unit (MCU) 42, for example an MC9S12E128 manufactured by Freescale. MCU 42 is electrically coupled to a real-time clock (RTC) 44 and is operable to control a pulse generator 46 to deliver an interferential (IF) mode treatment via a channel 1 IF output circuitry 48 and a channel 2 IF output circuitry 50, and to control a high voltage power supply portion 52 to deliver a neuromuscular electrical stimulation (NMES) mode treatment via a channel 1 NMES output circuitry 54 and channel 2 NMES output circuitry 56. Combination IF/NMES treatment modes are also available via channel 1 IF/NMES output circuitry 58 and channel 2 IF/NMES output circuitry 60. Power management circuitry 62 is electrically coupled to internal power source 64, for example a rechargeable battery as described above, a low voltage power supply 66, and high voltage power supply 52.

Representative embodiments of a battery charger and modem device 70 are depicted in FIGS. 5-11. A battery charger unit 72 and a data transfer and communication modem unit 74 are included in device 70. Several different battery charging approaches are known in the art and include 1) charging a battery within a device by plugging a charger or adapter into the device by a cable and coupling means, wherein the battery itself may be built-in or removable; 2) charging a battery within a device by placing the device in a charging cradle or another device; and 3) removing a battery from a device the battery powers, wherein the battery is placed into a charging unit or otherwise coupled to a charging source. In one embodiment, the battery is preferably removed from stimulator 10 for recharging in battery charger unit 72 that accompanies stimulator 10, although other charging processes and configurations can also be used. For example, in other embodiments stimulator 10 directly interfaces with battery charger unit 72 to charge the battery.

Figure 5B:
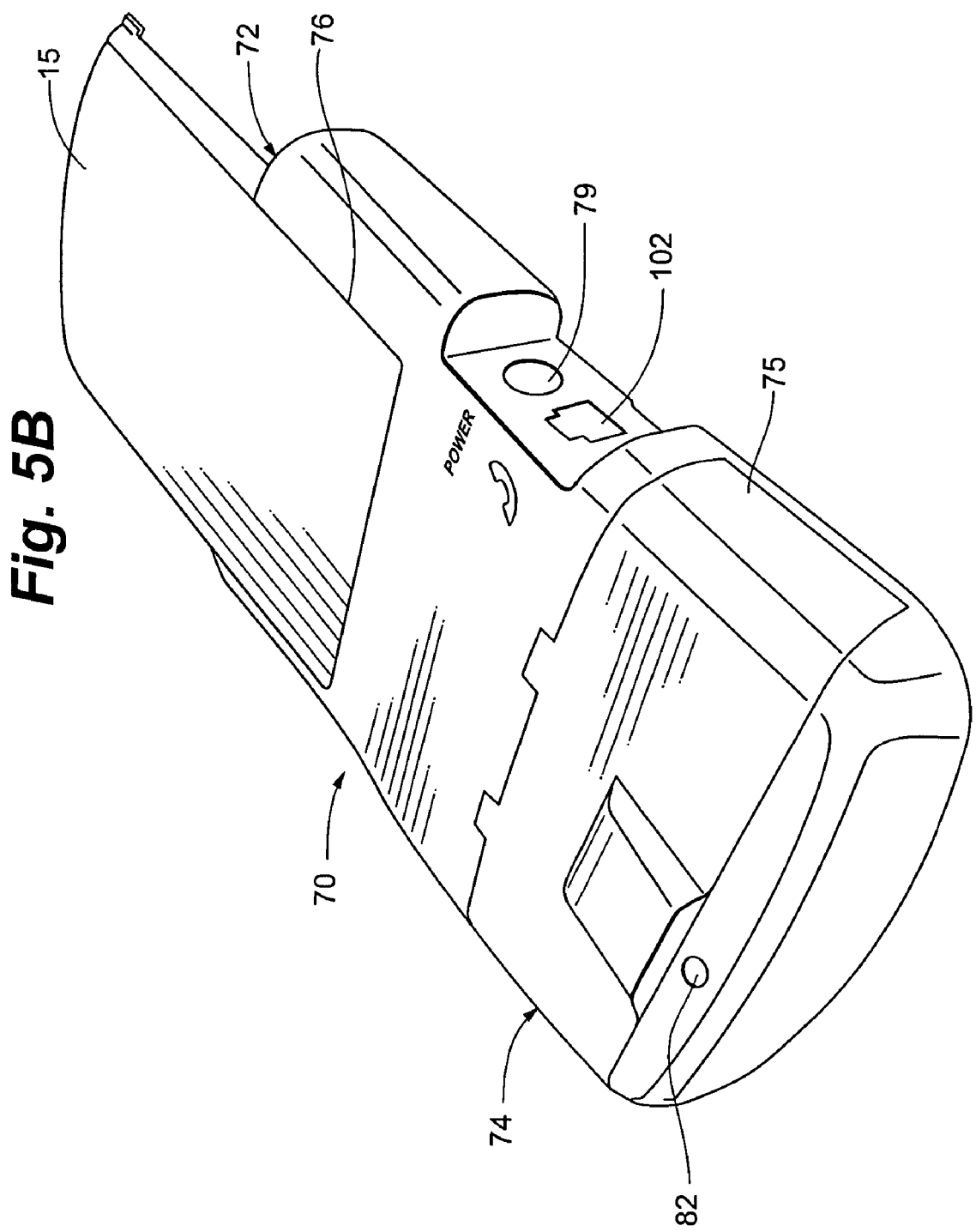
FIG. 5B is a view of a battery and the docking station of FIG. 5A.
Figure 5C:
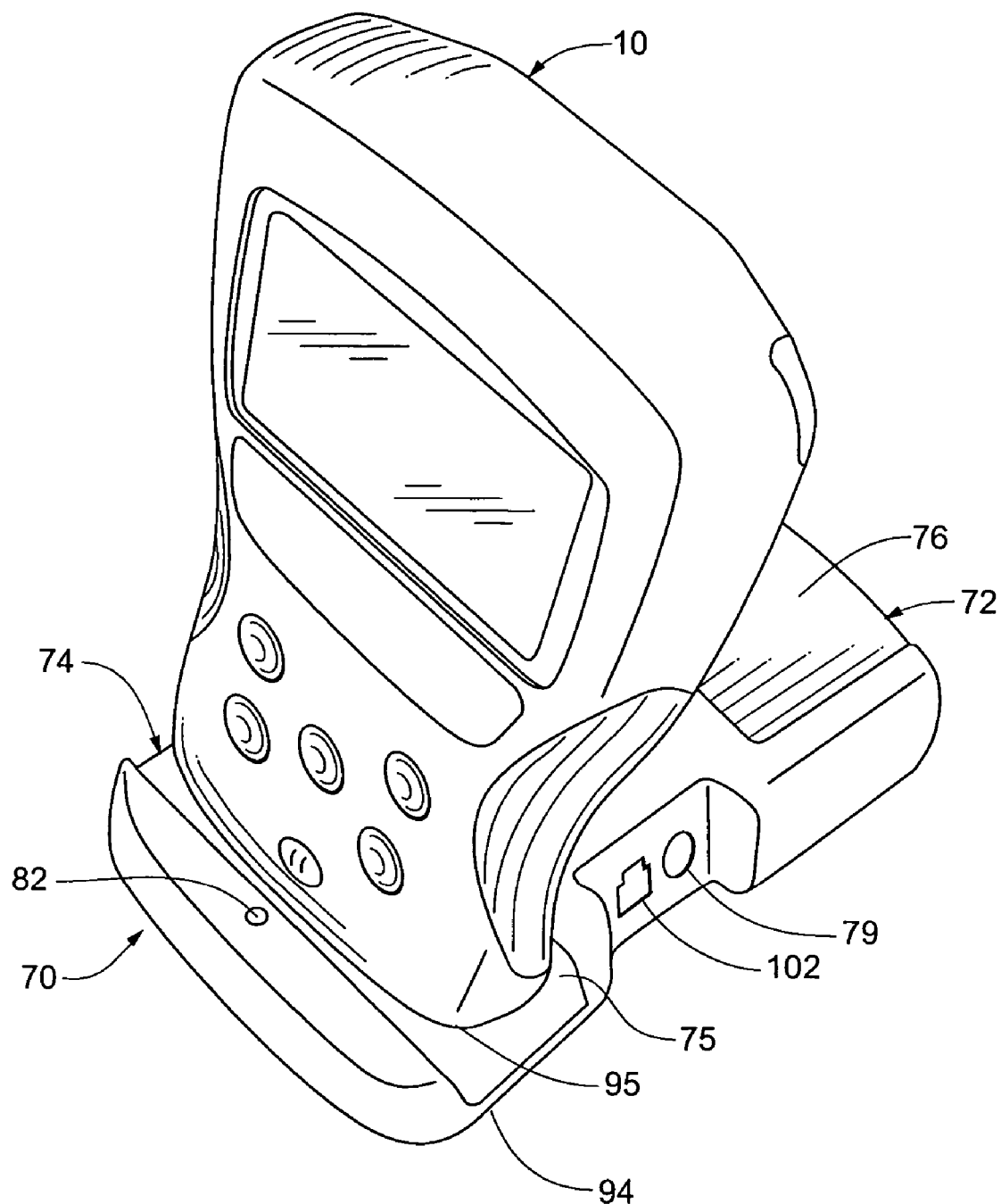
FIG. 5C is a view of a stimulator and the docking station of FIG. 5A.

FIGS. 5A, 5B, and 5C depict one embodiment of device 70 comprising a battery connector or cradle 76 having positive, negative, and thermal monitoring terminals for electrically coupling to the corresponding terminals of a battery 15 when the battery is inserted for charging. Internal battery charger circuitry 78 (refer to FIG. 9) couples cradle 76 to an external power source 80 (refer to FIG. 9) via cable connector 79. In one embodiment, unit 72 includes an AC/DC adapter to interface with connector 79 to power device 70. Device 70 can also include an external battery charging indicator 82. In one embodiment, indicator 82 is a light emitting diode (LED) that is illuminated when a battery is coupled to battery connector 76 and is being charged.

In one embodiment, modem unit 74 comprises a cradle connector 94 that includes an electrical and communication interface 95 to operably couple unit 74 with stimulator 10. Connector 94 and interface 95 are protected by a pivotable or removable cover 75. When open, cover 75 can also provide additional support to secure stimulator 10 in a generally upright position. Unit 74 also comprises a line interface 102, for example an external cable jack, in one embodiment to communicatively couple unit 74 to a telephone line, computer, or other communication medium FIG. 6 depicts another embodiment of device 70, wherein rechargeable battery 15 is removed from stimulator 10 and placed in a battery charger unit of device 70 for charging, while stimulator 10 is placed in unit 74 for data transfer or storage. Battery charger unit 72 includes battery connector or cradle 76.

Figure 7A:
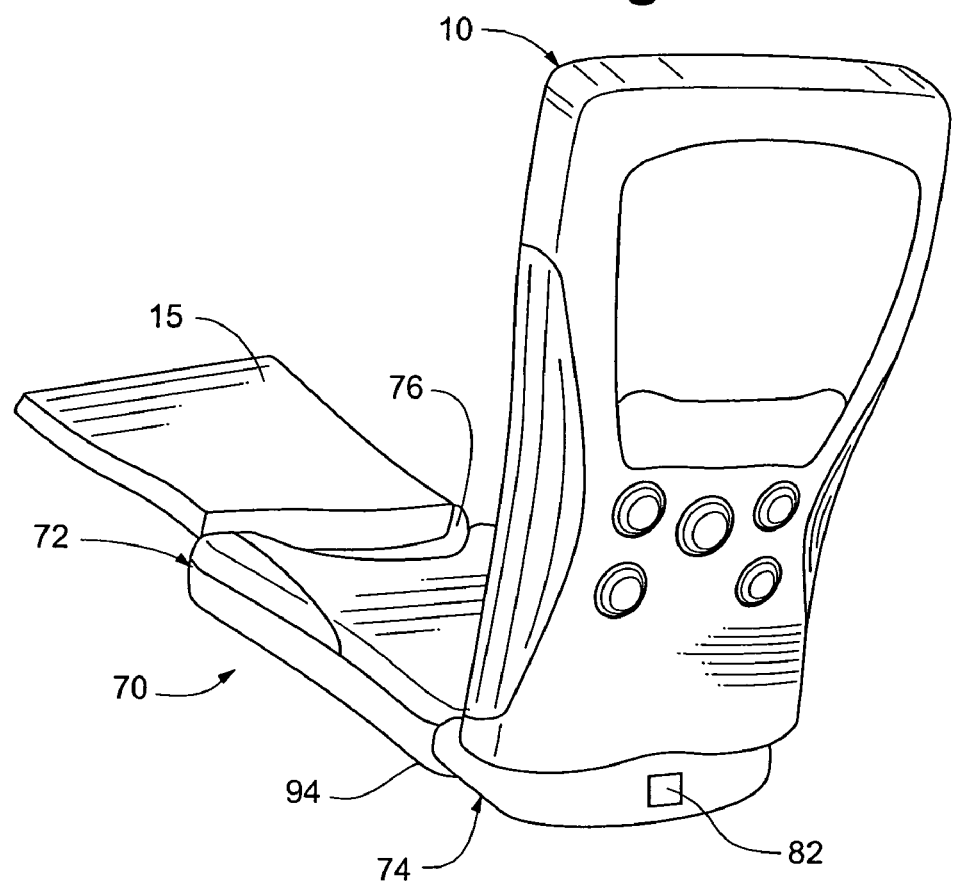
FIG. 7A is a view of a stimulator and docking station according to one embodiment of the invention.
Figure 7B:
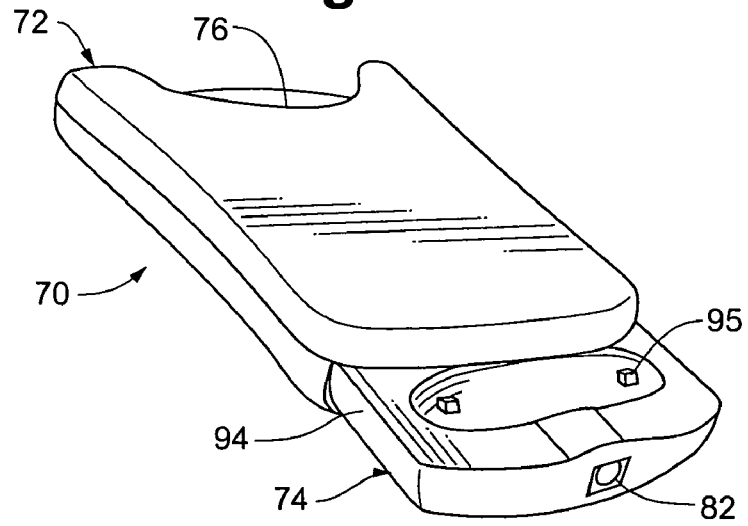
FIG. 7B is a view of the docking station of FIG. 7A.

FIGS. 7A and 7B depict another embodiment of device 70, in which unit 74 is connected to and stored within device 70 and slides out to expose a connector 94 and an interface 95 to operably and electrically couple stimulator 10 to device 70. Battery 15 slidably engages a charging bay that houses connector 76 of unit 74.

Figure 8A:
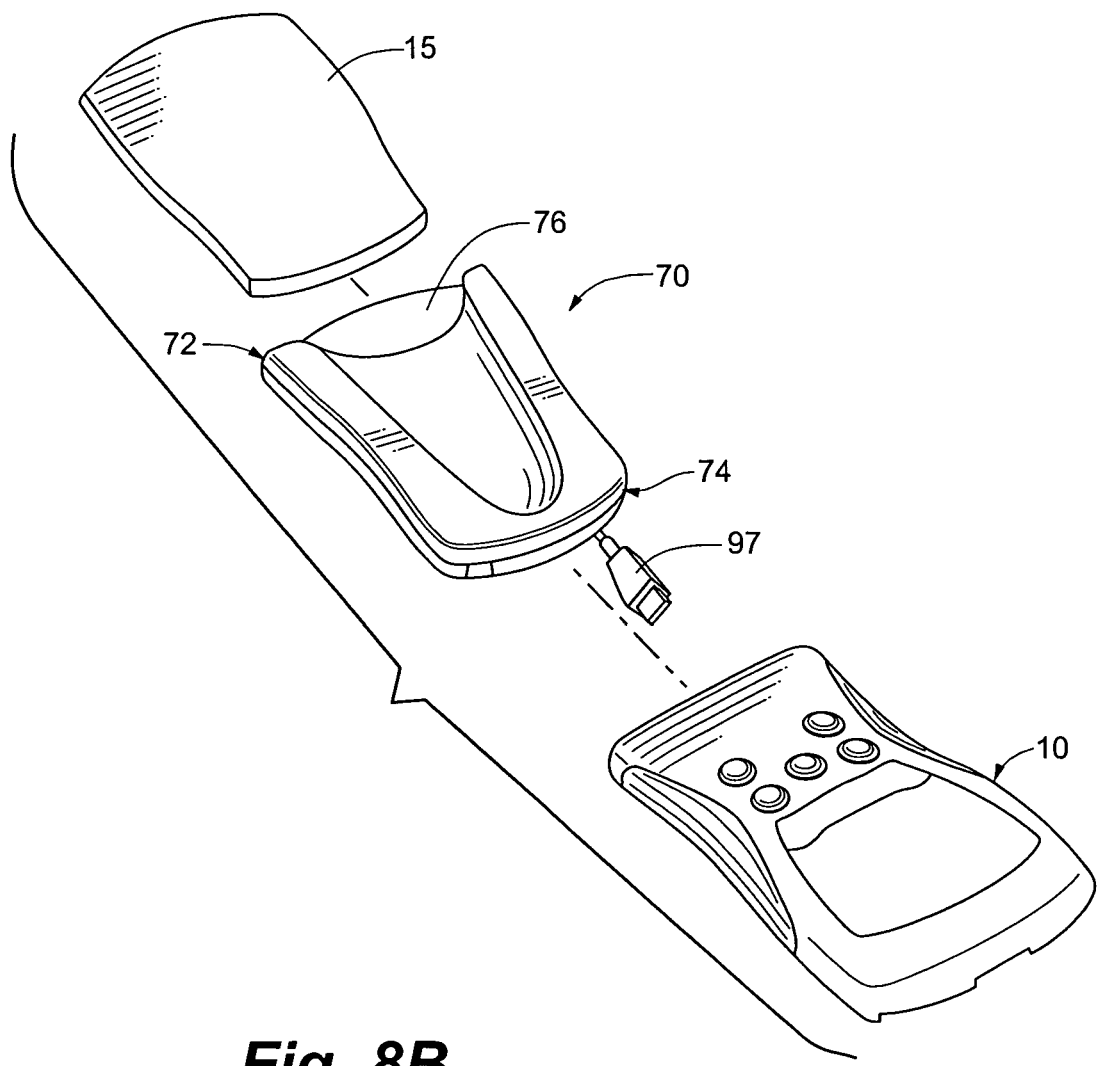
FIG. 8A is a view of a stimulator and docking station according to one embodiment of the invention.
Figure 8B:
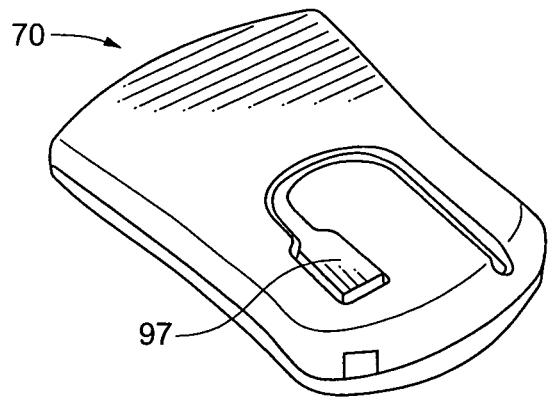
FIG. 8B is a view of the docking station of FIG. 8A.

FIGS. 8A and 8B depict yet another embodiment of device 70, wherein unit 74 comprises a cable interface 97 to electrically and communicatively couple stimulator 10 to device 70.

Cable interface 97 can be recessed or otherwise retracted into device 70 for storage when not in use. Similar to other embodiments, battery 15 slidably engages a charging bay that houses connector 76 of unit 74.

Figure 9:
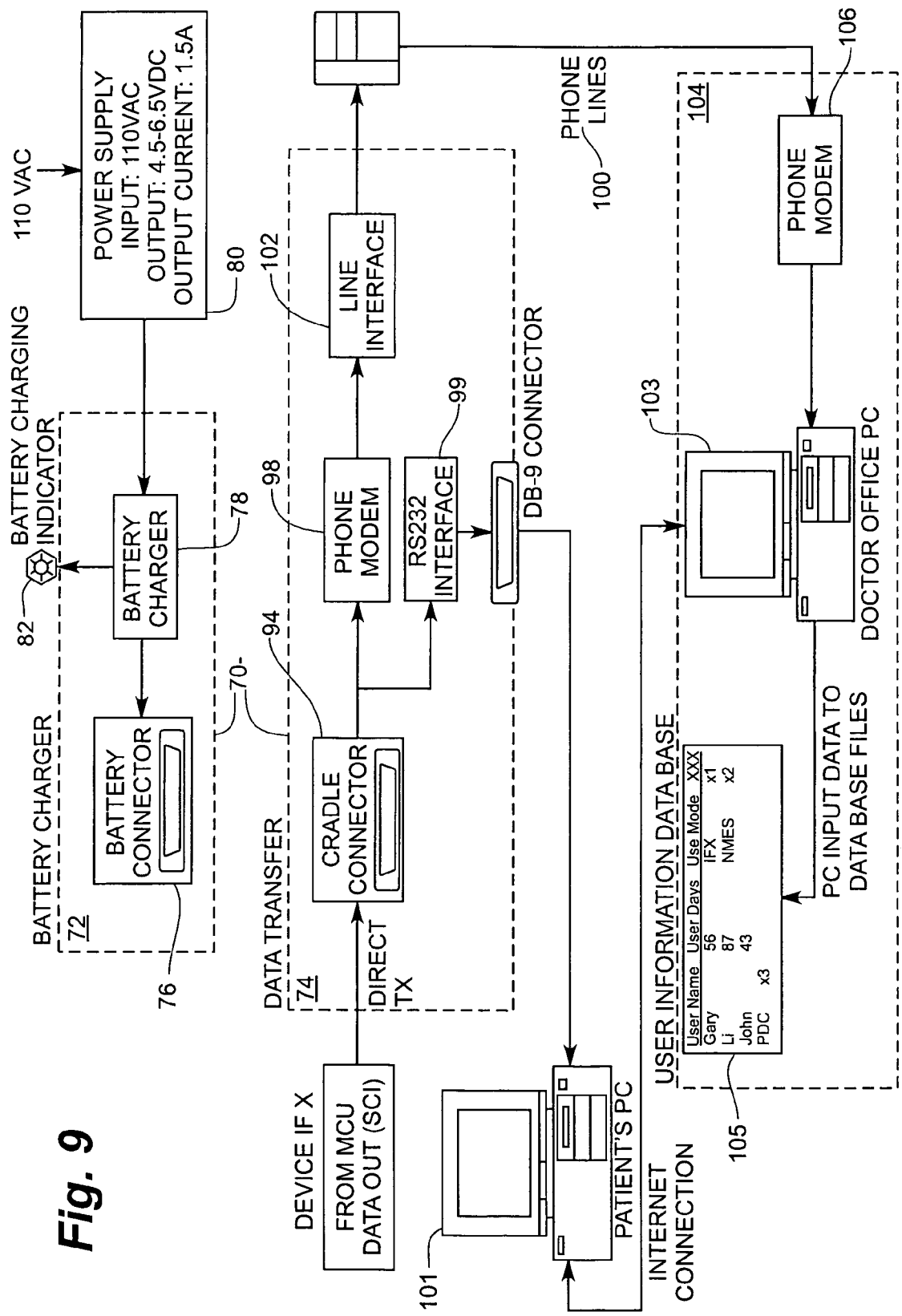
FIG. 9 is a block diagram according to one embodiment of the invention.

In FIG. 9, data transfer and communication modem unit 74 can include cradle connector 94 into which stimulator 10 is placed to carry out a data transfer procedure. Cradle connector 94 includes interface 95 (FIG. 7B, for example) adapted to electrically couple to a connector arranged externally on case 12 of stimulator 10. In other embodiments, a cable connection, infrared, radio frequency, and other wireless communication techniques can be used to couple communicatively couple stimulator 10 to unit 74. Cradle connector 94 is communicatively coupled to a telephone/telecommunications modem device 98 that is connected to a telephone/telecommunications line 100 via line interface 102. Telephone/telecommunications line 100 can be accessed via a standard wall jack, or through another device that includes an accessible telephone/telecommunications jack or other communication interface means, for example a telephone, Internet-connected computer, cable modem, wireless modem or service, satellite modem, mail service, or handheld personal data device. For example, an RS232 interface 99 can couple cradle connector 94 to a personal computer (PC) 101 connected to the Internet. A database station 104 having a modem 106 communicatively connected to telephone/telecommunications line 100 exchanges data and information with stimulator 10 via data transfer and communication modem unit 74 and/or via Internet-connected PC 101, and a database side PC or server 103 and database 105, when stimulator 10 is set in or otherwise coupled to cradle connector 94.

Figure 10:
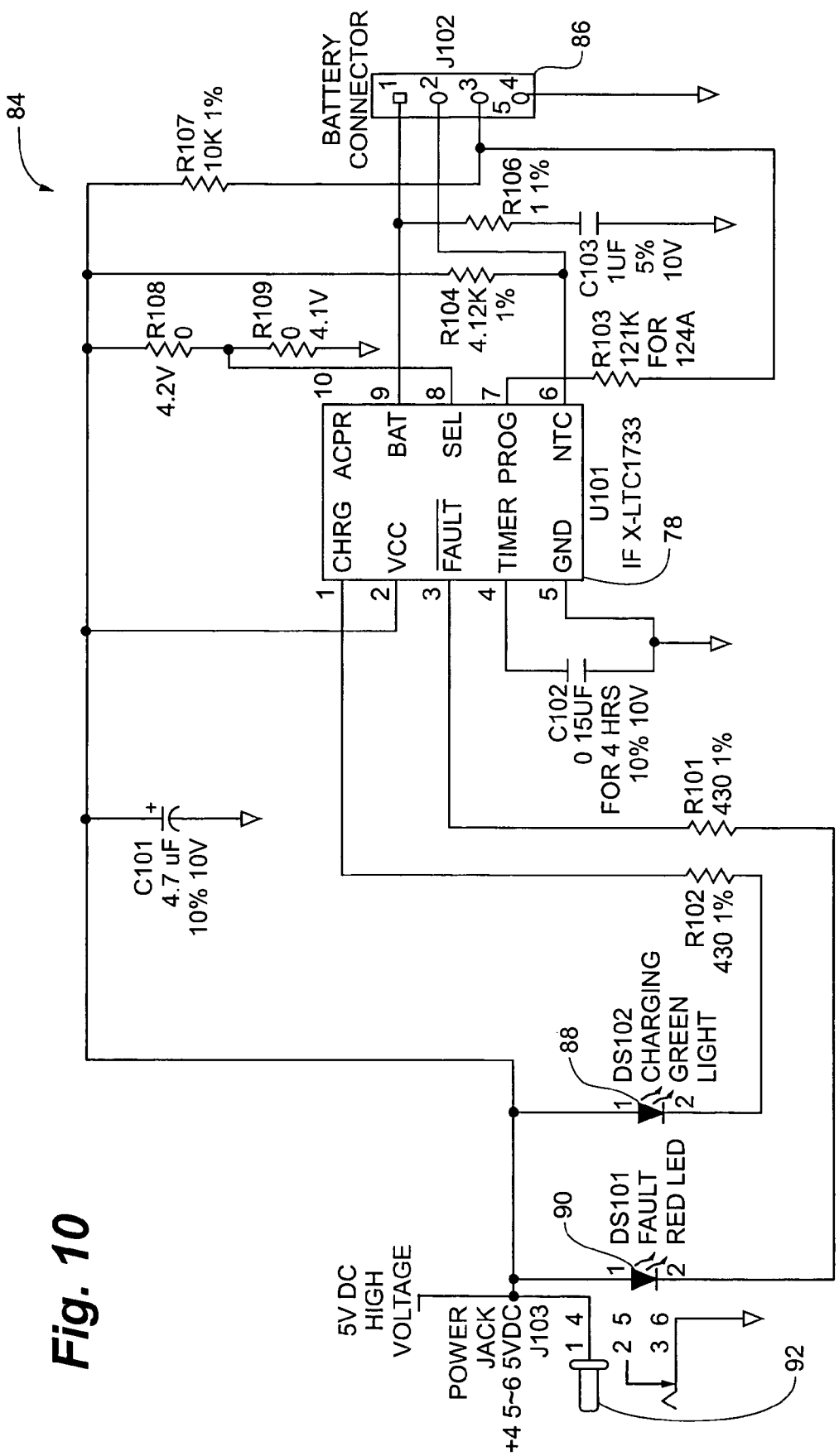
FIG. 10 is a circuit schematic of one embodiment of a battery charger device according to one embodiment of the invention.
Figure 11B:
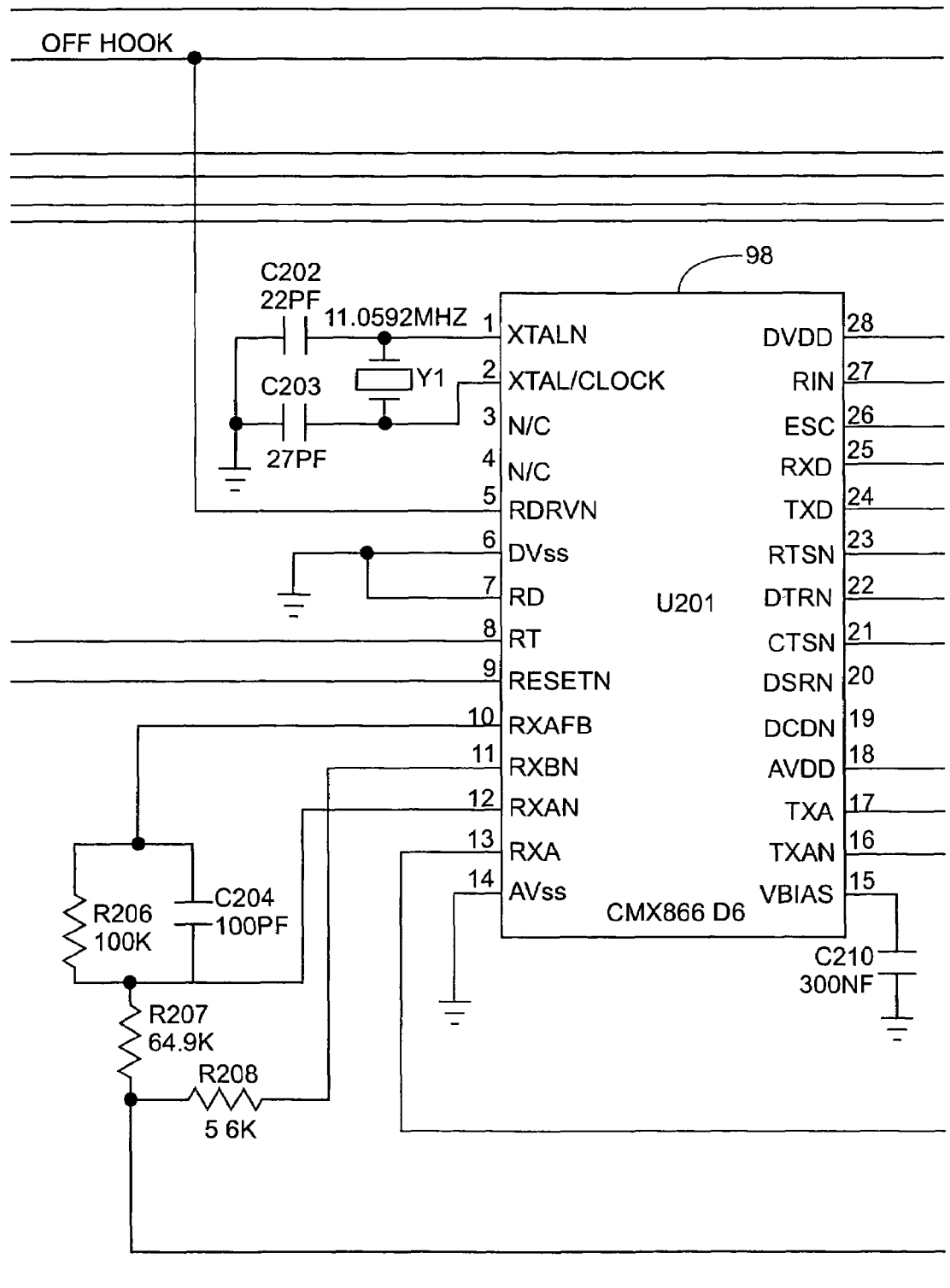
FIG. 11 is a circuit schematic of one embodiment of a modem device according to one embodiment of the invention.
Figure 11C:
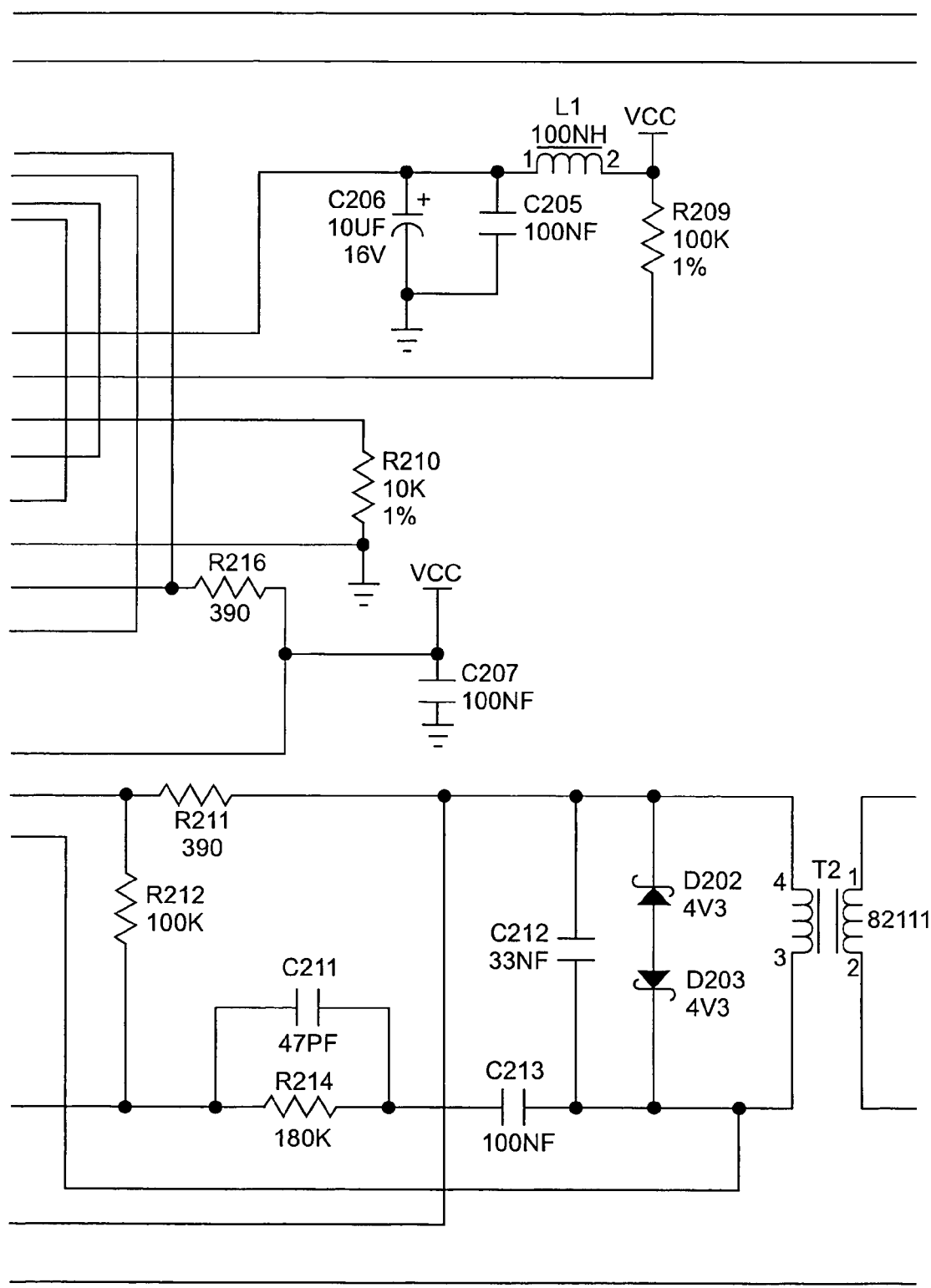
Figure 11D:
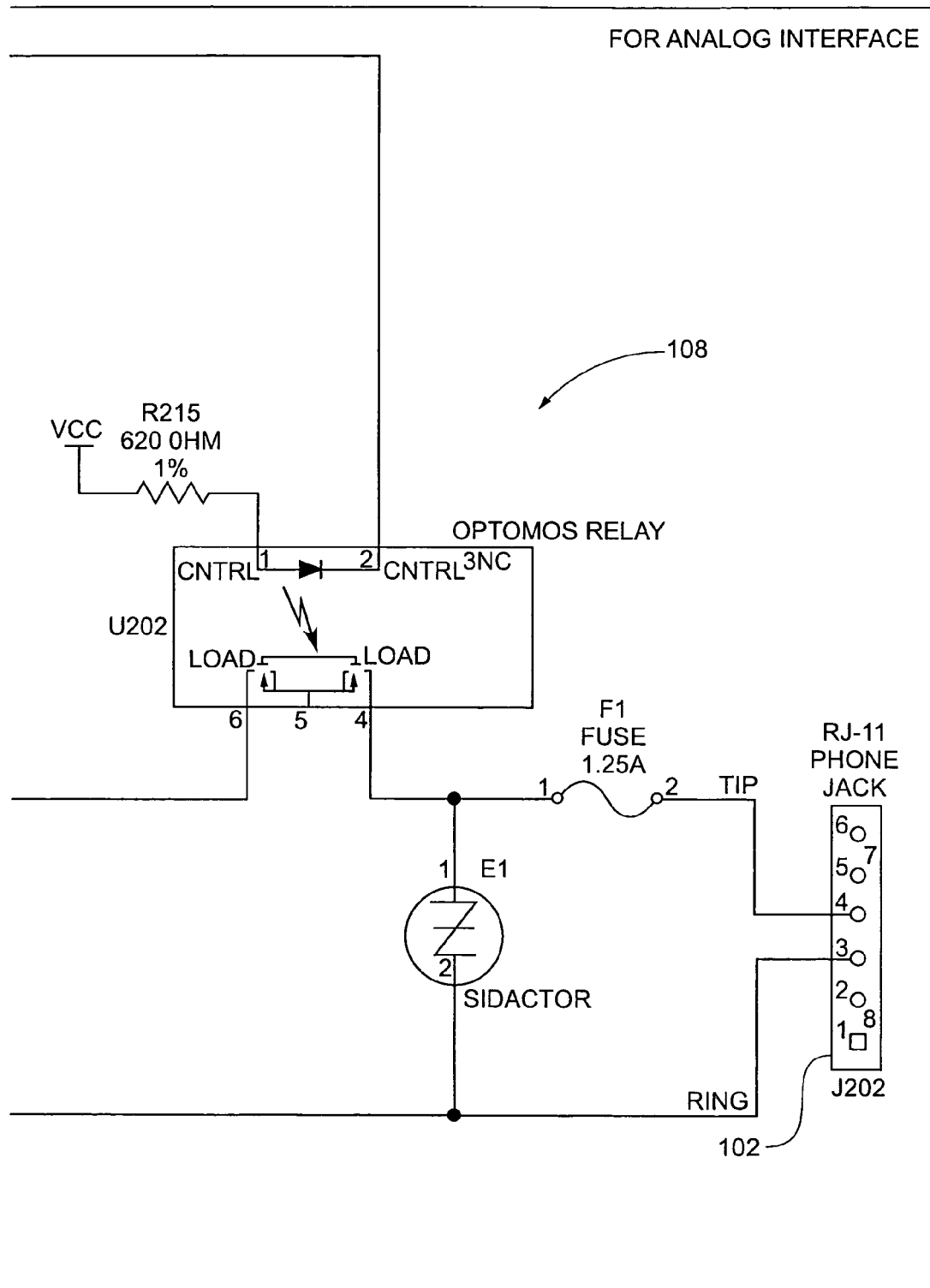
Figure 11E:
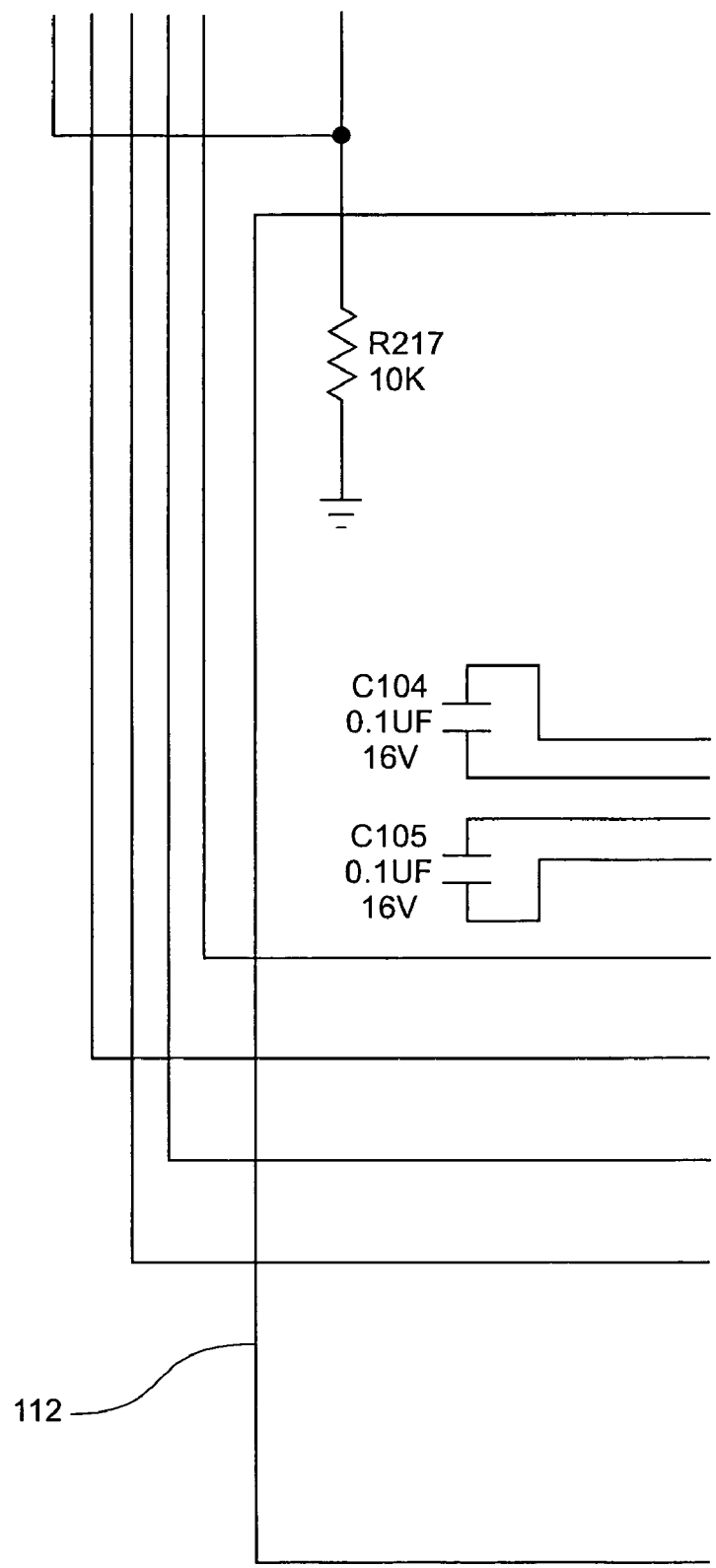
Figure 11F:
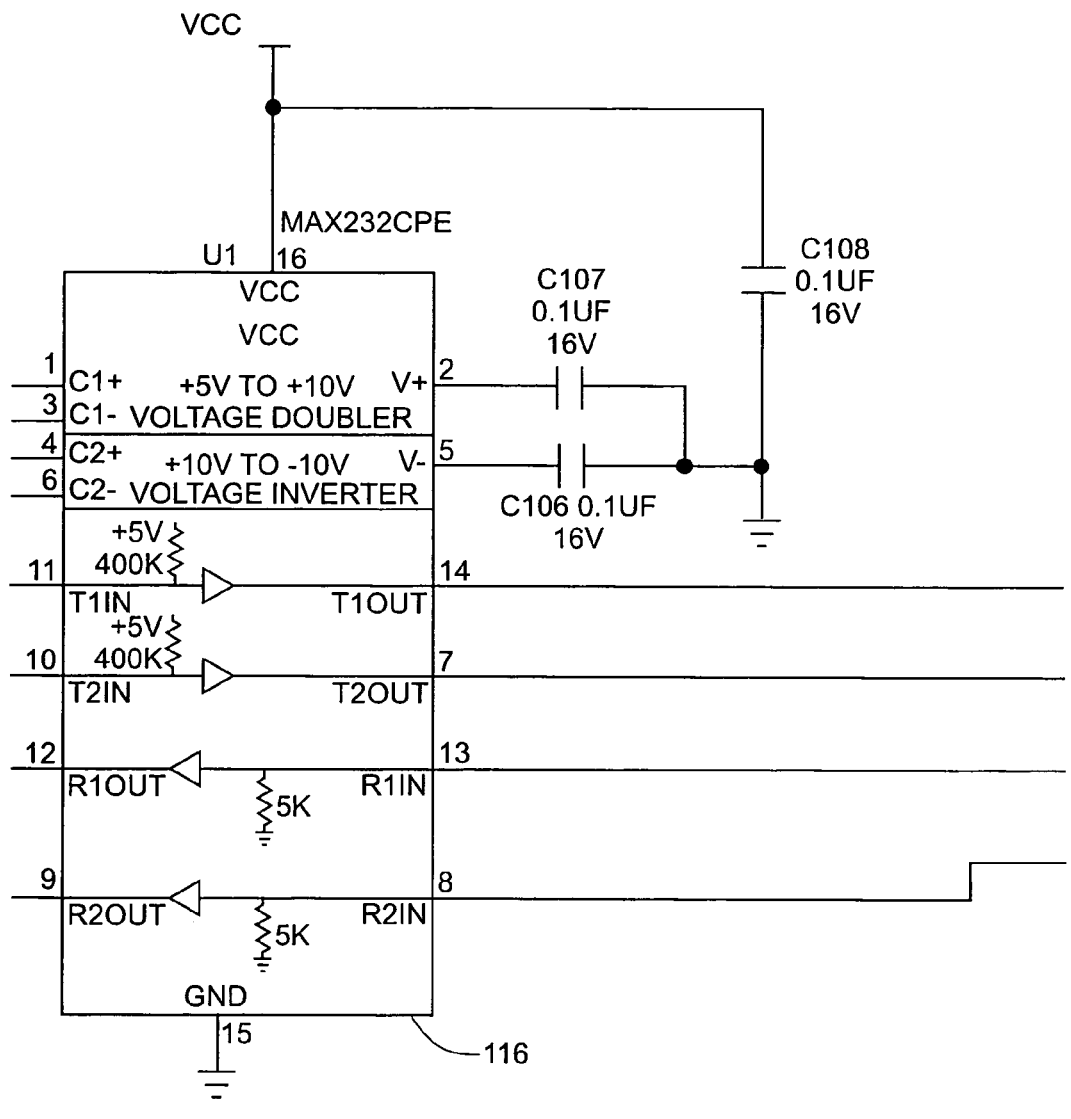
Figure 11G:
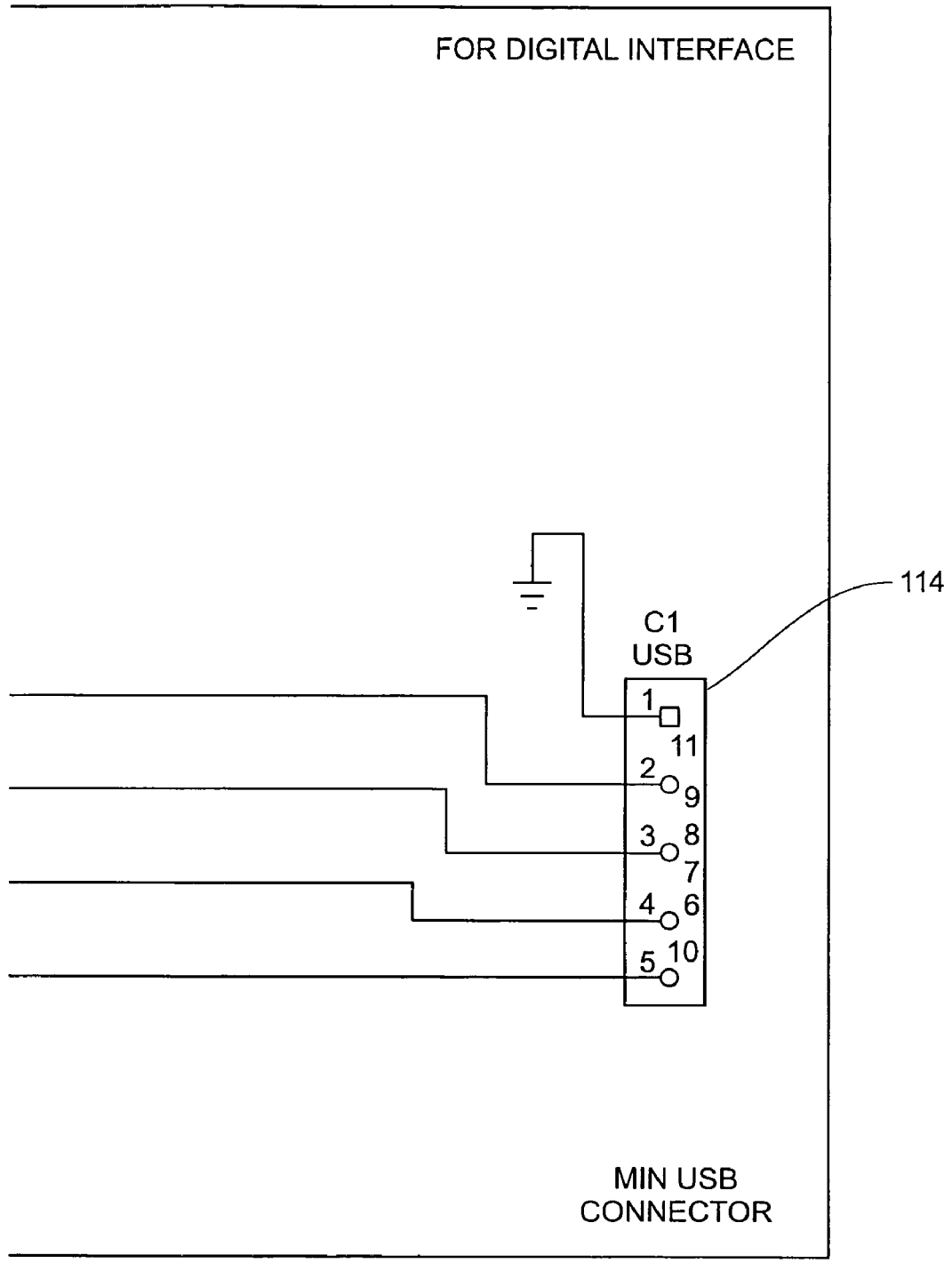

In FIG. 10, internal circuitry 84 of device 70 includes lithium-ion battery charger 78, for example an LTC1733 in one embodiment, and battery connector 86. In one embodiment, device 70 includes charging indicator 88 and a fault indicator 90, which can be combined into a single element, for example a single LED, or which can be separate elements, for example first and second LEDs of differing colors. External power interface 92 is also shown.

A circuit schematic diagram of one embodiment of circuitry 108 internal to unit 44 is depicted in FIG. 11. Circuitry 108 can include either or both analog interface circuitry 110 and digital interface circuitry 112. In one embodiment, modem device 98 comprises a CMX866 modem communicatively coupled to stimulator 10. Device 98 is communicatively coupled to telephone/telecommunications line 100 at line interface 102, which can be a standard RJ-11 jack. Unit 44 can also include an interface 114 via driver/receiver 116. In one embodiment, driver/receiver 116 is an RS-232 device, for example a MAX232CPE driver/receiver. Interface 114 can be an RS-232 direct interface to a PC common port in one embodiment. In another embodiment, driver/receiver 116 is a USB interface chip and interface 114 is a USB interface connector. Unit 44 can further comprise a data transmission indicator 118, for example an LED.

In use, stimulator 10 is capable of delivering at least three different electrotherapy modalities, including interferential (IF), neuromuscular electrical stimulation (NMES), and pulsed direct current (PDC) electrical stimulation. An interferential and neuromuscular electrical stimulation (IF/NMES) combination modality can also be delivered. Each of these modalities and the corresponding use and operation of the stimulator 10 will be described in more detail below.

To provide the various and distinct treatment modalities identified above, one embodiment of stimulator 10 of the invention includes circuitry that provides for an automatic changeover of electrode configurations between IF and NMES stimulation without the need to manually alter the positioning of the stimulation electrodes. This feature simplifies use and treatment. In an IF treatment mode, four electrodes operating on two stimulator channels are arranged in a cross-position orientation. In an NMES treatment mode, the four electrodes are positioned in parallel. Instead of requiring a user or operator to manually reposition the electrodes in a combination IF/NMES treatment mode, stimulator 10 includes circuitry that automatically switches the two internal channel output connections, providing continuous combination IF/NMES treatment without manual electrode repositioning.

Figure 12:
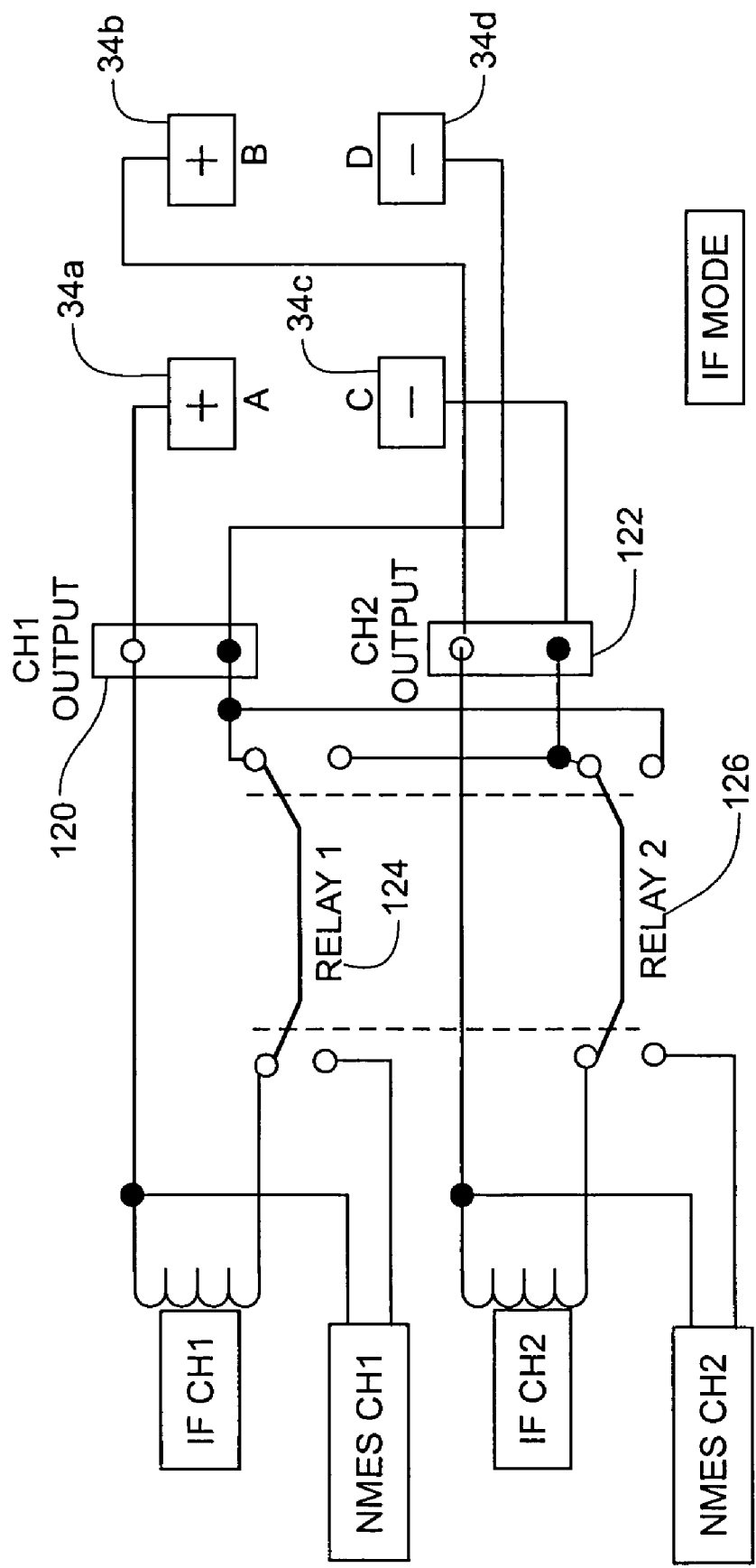
FIG. 12 is a first internal switching circuit diagram of a stimulator according to one embodiment of the invention.

FIG. 12 is a circuit diagram of one embodiment of the internal channel connections of stimulator 10. As depicted, electrodes 34a, 34b, 34c, and 34d are connected for operation in an IF treatment mode. In particular, Channel 1 output 120 is connected to electrodes 34a and 34d and Channel 2 output 122 is connected to electrodes 34b and 34c. Relay 1 (124) and relay 2 (126) are each in a first IF treatment position. In this position, relay 1 (124) completes an internal electrical connection that delivers internally generated IF treatment signals to Channel 1 output 120 and electrode 34d. In both an IF treatment mode and an NMES treatment mode, Channel 1 output 120 is electrically connected to electrode 34a. Similarly, relay 2 (122) completes an internal electrical connection that delivers internally generated IF treatment signals to Channel 2 output 122 and electrode 34c. While a preferred embodiment will be described in terms of automatic switching using relays, it will be recognized that other power electronic switches, such as a solid state switch or a high voltage analog switch, for example Part No. CPC 1943 Power Switch available from Clare Mfg. or HV23 high voltage analog switch available from Supertex Inc. could be used.

Figure 13:
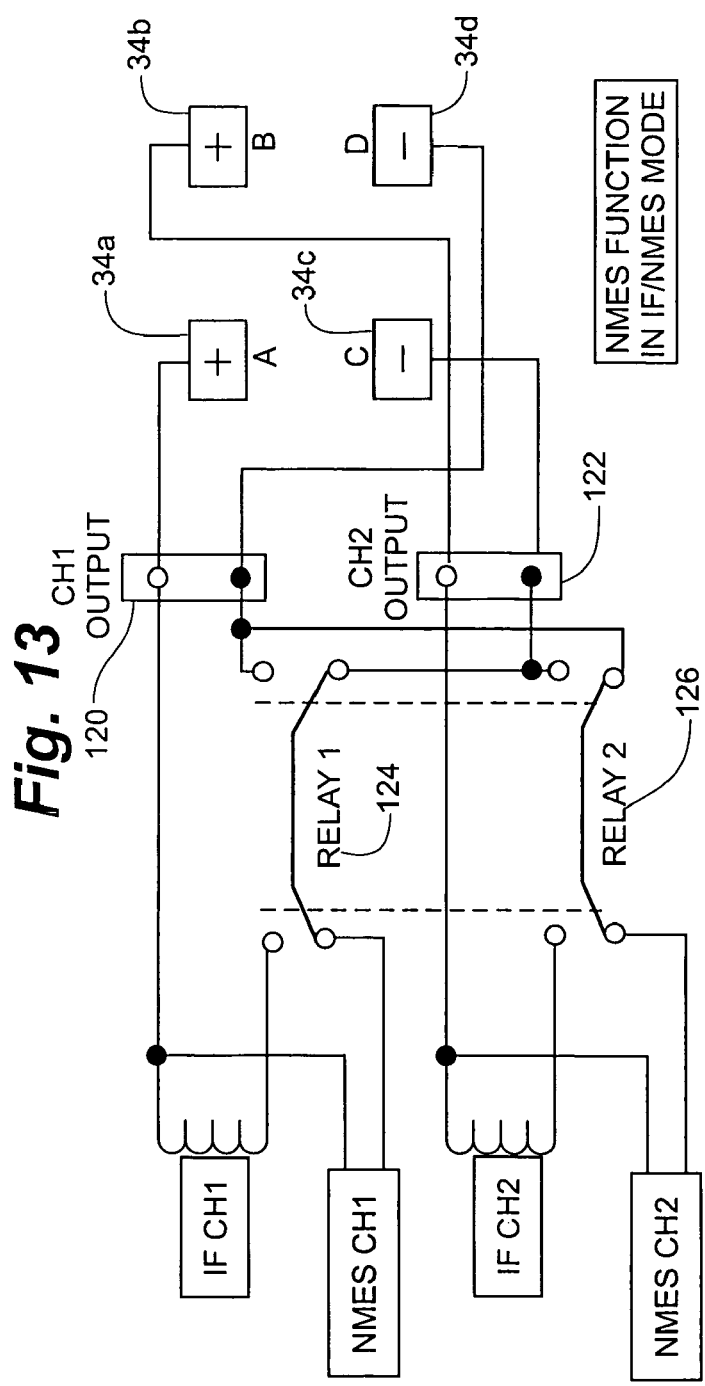
FIG. 13 is a second internal switching circuit diagram of a stimulator according to one embodiment of the invention.

In a combination IF/NMES treatment mode, stimulator 10 automatically switches internal relays 124 and 126 between the two external electrode placement configurations shown in FIG. 12 (IF) and FIG. 13 (NMES) and as previously described. For example, a combination IF/NMES treatment modality can be used to treat the lower back or lumbar area. A representative total treatment program can be about sixty minutes long, in which the first approximately twenty minutes delivers IF treatment, the middle approximately twenty minutes delivers NMES treatment, and the last approximately twenty minutes of the treatment program delivers IF treatment. These treatment and modality times can vary depending on a particular user's condition, an operator recommended or prescribed treatment, or other relevant factors and considerations. Internal relays 120 and 122 and the automatic relay switching control provided by stimulator 10 eliminate the need for a user to manually reconfigure the placement of the two sets of electrodes one or more times at the treatment area during a treatment session such as the exemplary treatment program described above.

In FIG. 13, relays 124 and 126 have been switched to deliver a NMES treatment program from the IF treatment program configuration shown in FIG. 12. When internal relays 124 and 126 are in these second positions, Channel 1 output 120 to electrode 34d is bypassed, electrically connecting Channel 1 output 120 to parallel electrodes 34a and 34c. Channel 2 output 122 is electrically connected to electrodes 34b and 34d. In use and operation, stimulator 10 automatically switches the internal channel connections in accordance with the requirements of the particular IF/NMES treatment program selected such that relays 124 and 126 alternately receive and electrically communicate IF and NMES treatment mode signals to external electrodes 34a, 34b, 34c, and 34d.

Various treatment programs can be preprogrammed in stimulator 10 and can also be created, customized, and disabled as desired by an operator to treat a particular patient, symptom, or condition. The IF, NMES, and PDC modalities, and IF/NMES combination modality, generally provide electro-stimulation treatment programs that vary in signal frequency, available energy range, treatment or cycle time, pulse width, and/or output; electrode configuration; or other electro-stimulation treatment signal characteristics known to those skilled in the art. Each of the aforementioned modalities is described in more detail below.

Figure 14:
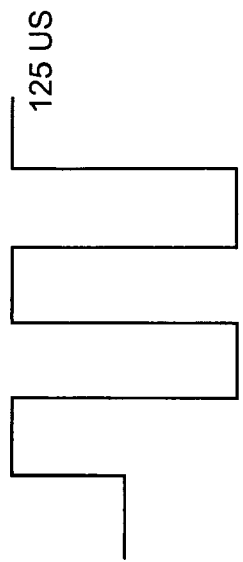
FIG. 14 is an interferential pulse waveform according to one embodiment of the invention.

An IF modality delivers a square wave biphasic pulse with zero net DC current in one embodiment. An exemplary IF pulse waveform of one embodiment is depicted in FIG. 14, having an approximate 125 microsecond pulse width. In this embodiment, channel 1 output 120 delivers a fundamental frequency fixed at about 4000 Hertz (Hz) and channel 2 output 122 delivers an adjustable frequency in the range of about 4001 Hz to about 4150 Hz, with an interference (beat) frequency of about 1 Hz to about 150 Hz in one exemplary embodiment of the invention. The output of stimulator 10 in an IF modality will be 0 mA to about 50 mA across a 500-Ohm load, constant voltage, adjustable in one percent increments. The output amplitude can be set simultaneously and equally for both channel 1 and channel 2 in all programs. The pulse width, frequencies, and outputs described above are representative of one embodiment and can be adjusted or varied in other embodiments of the invention. For example, can be about 1 Hz to about 150 Hz, as described above, adjustable in one hertz increments. Stimulator 10 can run continuously in this mode until a specified or set treatment time has completed, at which time stimulator 10 powers off, or until a user or operator manually powers off stimulator 10. In one embodiment, the treatment time is adjustable from about 10 minutes to about 60 minutes in ten-minute increments. Stimulator 10 can be programmed to default to an IF continuous mode with a frequency of 100 Hz.

IF sweep treatment programs are programs having an output wherein the interference frequency varies over a selected range. The range is from a minimum interference frequency to a maximum interference frequency and back to a minimum interference frequency, in a selected time. The time may be expressed as a sweep or a cycle and is defined as the ramp up time (minimum interference frequency to maximum interference frequency) and ramp down time (maximum interference frequency to minimum interference frequency) in each frequency sweep. The time will generally be expressed in units of seconds. The change in interference frequency within the range does not have to be, but generally is, linear per unit time. Exemplary IF sweep treatment programs of stimulator 10 are shown below in TABLE 1. The programs shown in the followings tables are exemplary combinations, for example for manual set programs, and custom programs can be created that includes unique combinations.

TABLE 1

| PROGRAM | SWEEP FREQUENCY RANGES | FREQUENCY CHANGE STEPS | CYCLE TIME (SELECTABLE) | TREATMENT TIME |
|---|---|---|---|---|
| IF Sweep | 1 to 150 Hz<br>1 to 10 Hz<br>30 to 70 Hz<br>80 to 150 Hz | 1 Hz | 6 sec. up/6 sec. down<br>12 sec. up/12 sec. down<br>24 sec. up/24 sec. down | 10 to 60 min. in 5 min. increments |
| IF Sweep Default | 1 to 150 Hz | 1 Hz | 6 sec. up/6 sec. down | 10 min. in 5 min. increments |

Figure 15:
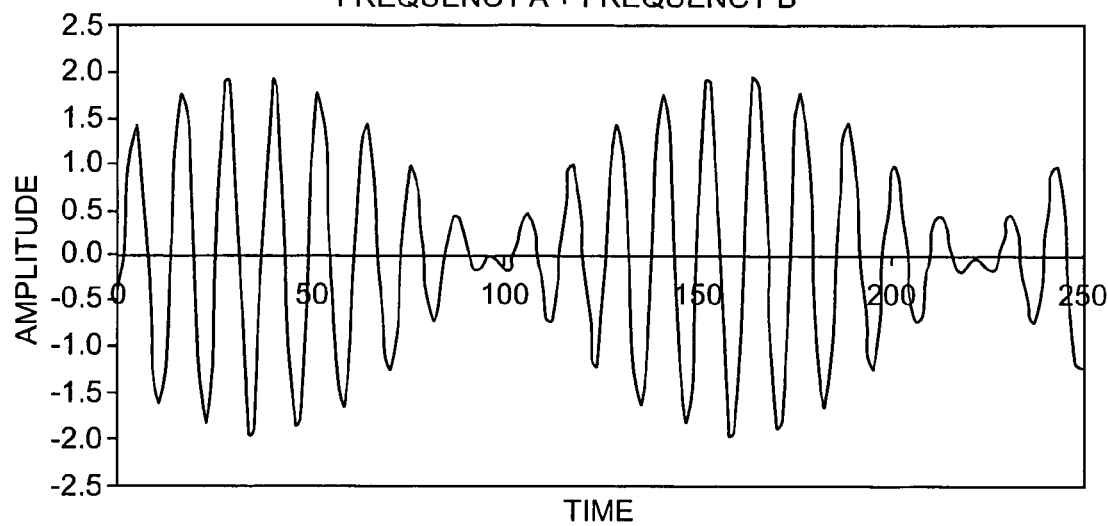
FIG. 15 is an analog interferential waveform according to one embodiment of the invention.
Figure 16:
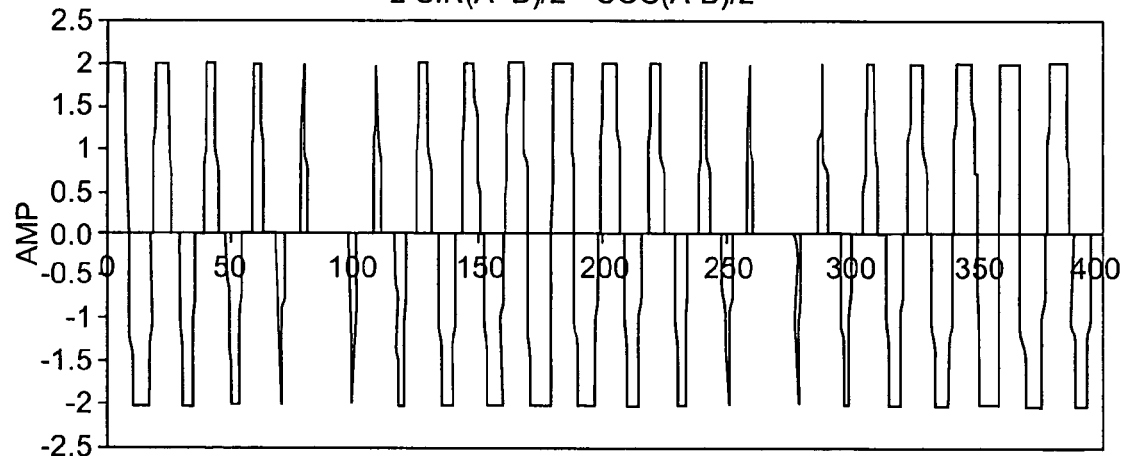
FIG. 16 is a digital interferential waveform according to one embodiment of the invention.

FIG. 15 depicts an exemplary analog interferential frequency and FIG. 16 shows a digital interferential frequency, each having a zero net DC current.

Several different IF treatment programs can be programmed and stored in stimulator 10. An IF continuous program has an IF continuous output at a set interference frequency with no frequency shift. The interference frequency Preset IF treatment programs can be programmed and saved in stimulator 10. The particular preset programs available to a user or group of users may be selected or disabled by an operator. The parameters of the preset programs are fixed and thus not generally adjustable or customizable by either an operator or a user. Exemplary preset IF treatment programs are shown in TABLE 2.

TABLE 2

| PRESET PROGRAM | TOTAL TREATMENT TIME | TREATMENT SEGMENT | SWEEP FREQUENCY RANGE 1 HZ INCREMENT | SWEEP TIME |
|---|---|---|---|---|
| Low Back Pain | 60 min. | 1st 30 min.<br>2nd 30 min. | 60 Hz to 150 Hz<br>5 Hz to 10 Hz | 24 sec up<br>24 sec. down |
| Neck Pain | 60 min. | 1st 30 min.<br>2nd 30 min. | 60 Hz to 150 Hz<br>1 Hz to 10 Hz | 12 sec up<br>12 sec. down |
| Knee Pain | 60 min. | 1st 30 min.<br>2nd 30 min. | 60 Hz to 150 Hz<br>1 Hz to 10 Hz | 24 sec up<br>24 sec. down |
| Shoulder Pain | 60 min. | 1st 30 min.<br>2nd 30 min. | 60 Hz to 150 Hz<br>1 Hz to 10 Hz | 24 sec up<br>24 sec. down |
| Wrist Pain | 60 min. | 1st 30 min.<br>2nd 30 min. | 80 Hz to 150 Hz<br>1 Hz to 10 Hz | 24 sec up<br>24 sec. down |
| Ankle Pain | 60 min. | 1st 30 min.<br>2nd 30 min. | 100 Hz to 150 Hz<br>1 Hz to 10 Hz | 24 sec up<br>24 sec. down |

TABLE 2-continued

| PRESET PROGRAM | TOTAL TREATMENT TIME | TREATMENT SEGMENT | SWEEP FREQUENCY RANGE 1 HZ INCREMENT | SWEEP TIME |
|---|---|---|---|---|
| IC Pain | 40 min. | 1st 10 min. | 100 Hz | N/A |
|  |  | 2nd 10 min. | 10 Hz |  |

Figure 17:
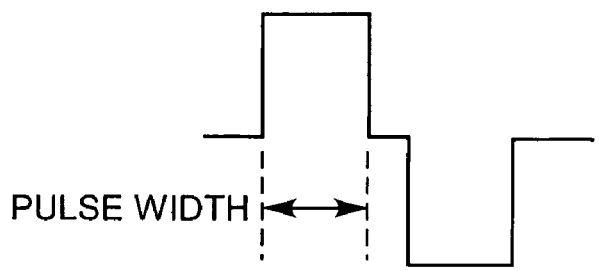
FIG. 17 is a symmetric square wave biphasic pulse of a neuromuscular electrostimulation treatment modality according to one embodiment of the invention.
Figure 18:
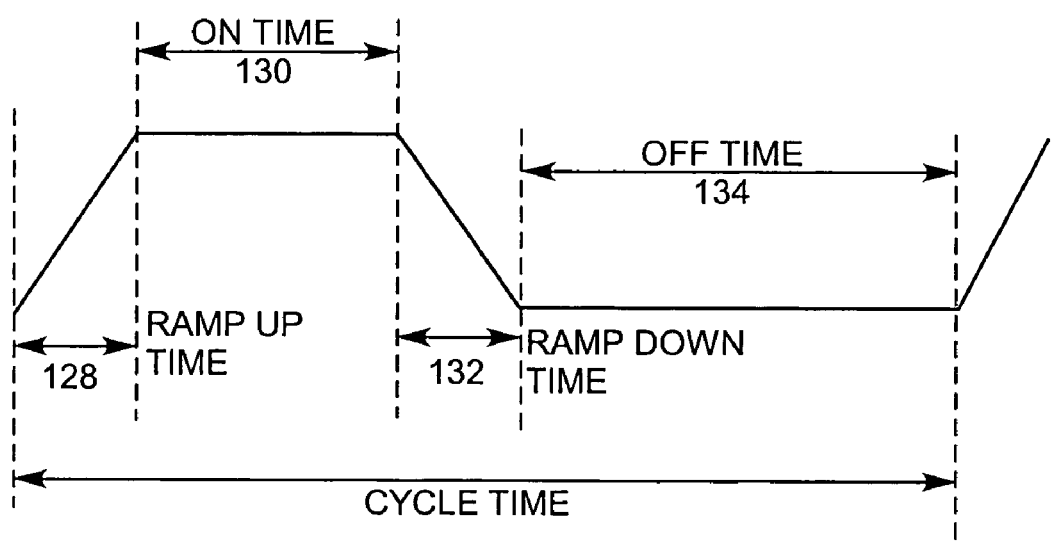
FIG. 18 is a graph of a neuromuscular electrostimulation treatment cycle according to one embodiment of the invention.

An NMES treatment modality delivers a symmetric square wave bi-phasic pulse with zero net DC current in one embodiment, as shown in FIG. 17. The pulse width can vary from about 70 microseconds to about 300 microseconds, selectable in 10 microsecond increments, in this embodiment. The increments depend on a choice of design and can vary in different increments and ranges. The output frequency can be adjustable from about 10 Hz to about 80 Hz in 5 Hz increments, and NMES output can be adjustable from about 0 mA to about 100 mA, constant current, in 1 mA increments across an approximately 1000-Ohm load. An NMES treatment cycle includes four timed phases for one channel. For two-channel applications, the treatment cycle is from the beginning of channel one to the end of channel two. These phases for each output channel are a up-ramp phase 128, an on phase 130, a down-ramp phase 132, and an off phase 134, as illustrated in FIG. 18.

Various NMES treatment programs can be preset and stored in stimulator 10. The particular preset programs available to a user or group of users may be selected or disabled by an operator. The parameters of the preset programs are fixed and thus not generally adjustable or customizable by either an operator or a user. Exemplary preset NMES treatment programs are shown in TABLE 3.

TABLE 3

| PRESET PROGRAM | TREATMENT TIME | FREQUENCY | PULSE WIDTH | RAMP UP TIME | ON TIME | RAMP DOWN TIME | OFF TIME |
|---|---|---|---|---|---|---|---|
| Low Back Spasm Reduction | 10 min. | 80 Hz. | 300 µs | 2 sec. | 8 sec. | 2 sec. | 2 sec. |
| Neck/Upper Back Spasm Reduction | 10 min. | 50 Hz | 150 µs | 3 sec. | 6 sec. | 3 sec. | 2 sec. |
| Mid/Low Back Strengthening | 15 min. | 35 Hz | 300 µs | 2 sec. | 10 sec. | 2 sec. | 10 sec. |
| Trigger Point Therapy | 30 min. | 50 Hz | 300 µs | 3 sec. | 10 sec. | 2 sec. | 10 sec. |
| Quadriceps Strengthening | 15 min. | 50 Hz | 300 µs | 3 sec. | 10 sec. | 2 sec. | 10 sec. |
| Quadriceps Re-education | 15 min. | 50 Hz | 300 µs | 3 sec. | 10 sec. | 2 sec. | 30 sec. |

Stimulator 10 can be configured to allow an operator or user to set up and store manual muscle stimulation programs, including manual NMES programs. In one embodiment, manual programs can have the following operator- or user-customizable features and parameters:

Pulse width setting: about 70 to about 300 µs, in 10 µs increments

Pulse rate setting: about 10 to about 80 Hz in 5 Hz increments

Ramp up time: about 0 to about 10 seconds, in one second increments

On time: about one to about 30 seconds, in one second increments

Ramp down time: about 1 to about 60 seconds, in 0.5 second increments

Off time: about 1 to about 60 seconds, in one second increments

LAG time: about 0 to about 15 seconds, one second increments

Treatment time: about 10 to about 60 minutes, in 5 minute increments

Manual programs can be set up using a single channel output or two channel outputs. In one embodiment, three manual two-channel treatment cycle programs are available. These include a simultaneous treatment cycle program, a lag treatment cycle program, and an alternate cycle treatment cycle program. In each of the two channel manual treatment cycle programs, the output pulse width and pulse rate will be the same for each channel. Defaults can be programmed in stimulator 10 for each of the features and parameters of the manual programs, wherein the defaults can be subsequently edited or accepted by an operator during set-up of a particular manual program for a user or group of users.

Figure 19:
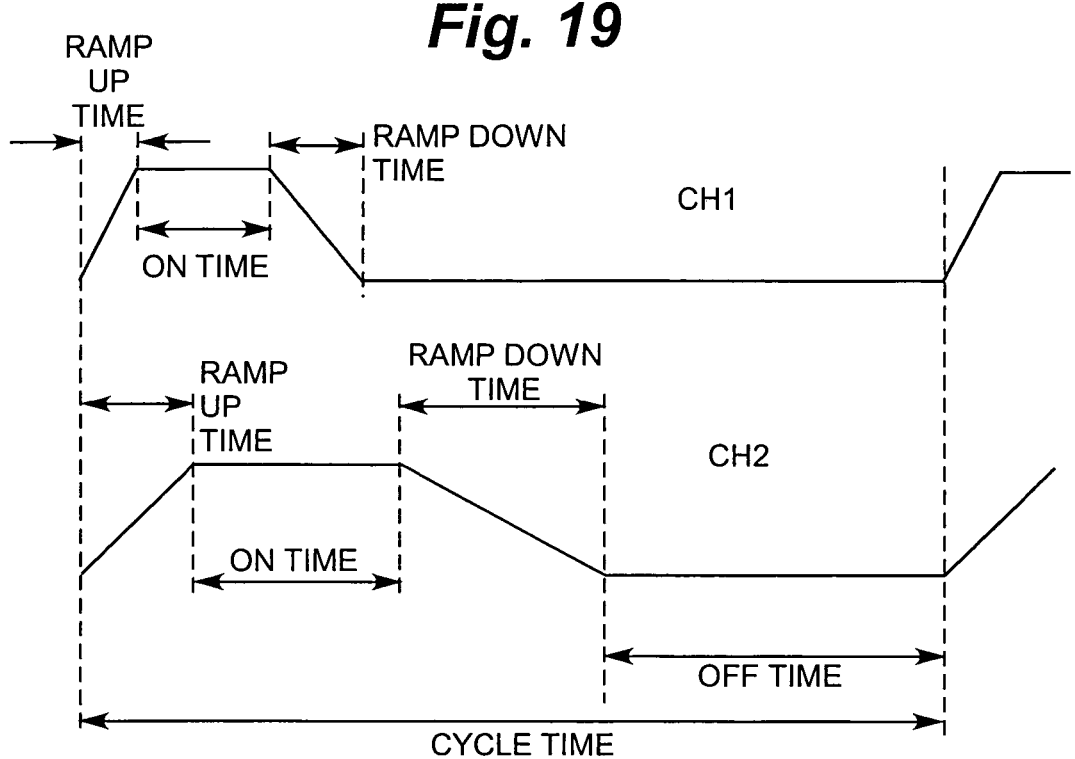
FIG. 19 is a two-channel simultaneous treatment cycle according to one embodiment of the invention.

In one embodiment of a simultaneous treatment cycle program, the outputs for each channel 1 and channel 2 begin at the same time. The off time is defined as the time between the longest channel treatment cycle and the start of the next output treatment cycle. FIG. 19 depicts one embodiment of a two-channel simultaneous treatment cycle.

Figure 20:
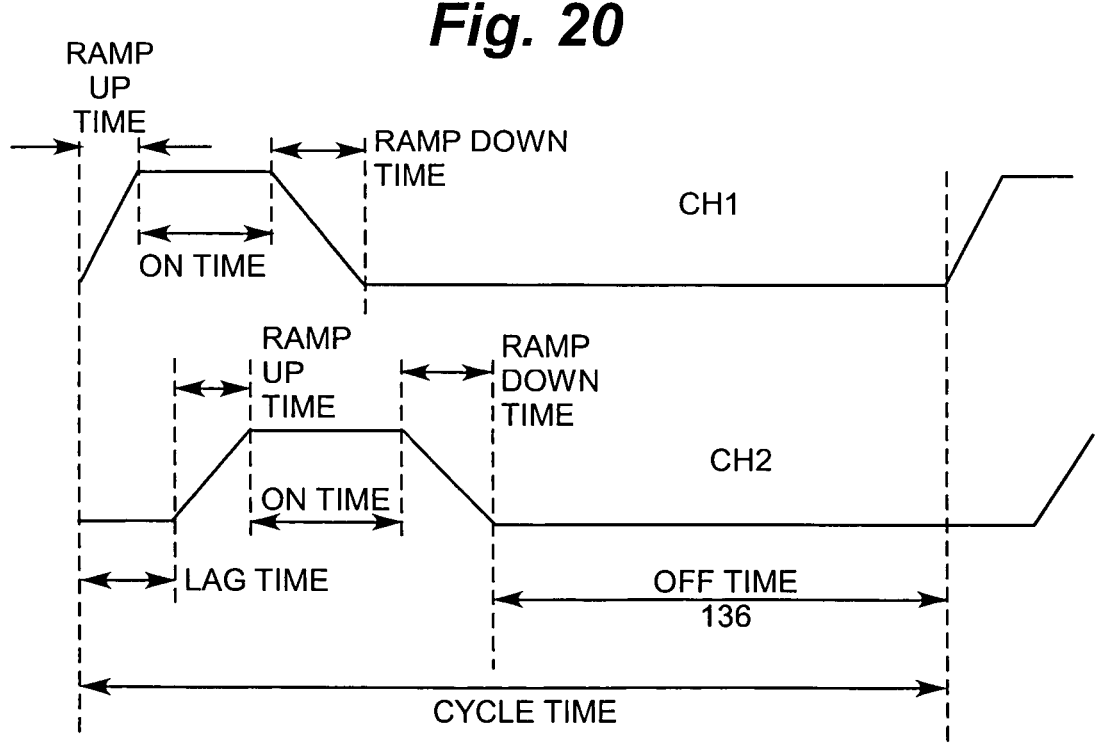
FIG. 20 is a two-channel graph of a lag treatment cycle program according to one embodiment of the invention.

The output for channel 2 begins after, or "lags," the output of channel 1 in a lag treatment cycle program, one embodiment of which is depicted in FIG. 20. An off time 136 in a lag treatment cycle program is defined as the time between the end of channel treatment cycle for channel 1/channel 2 and the beginning of the output of channel 1 for the next treatment cycle.

Figure 21:
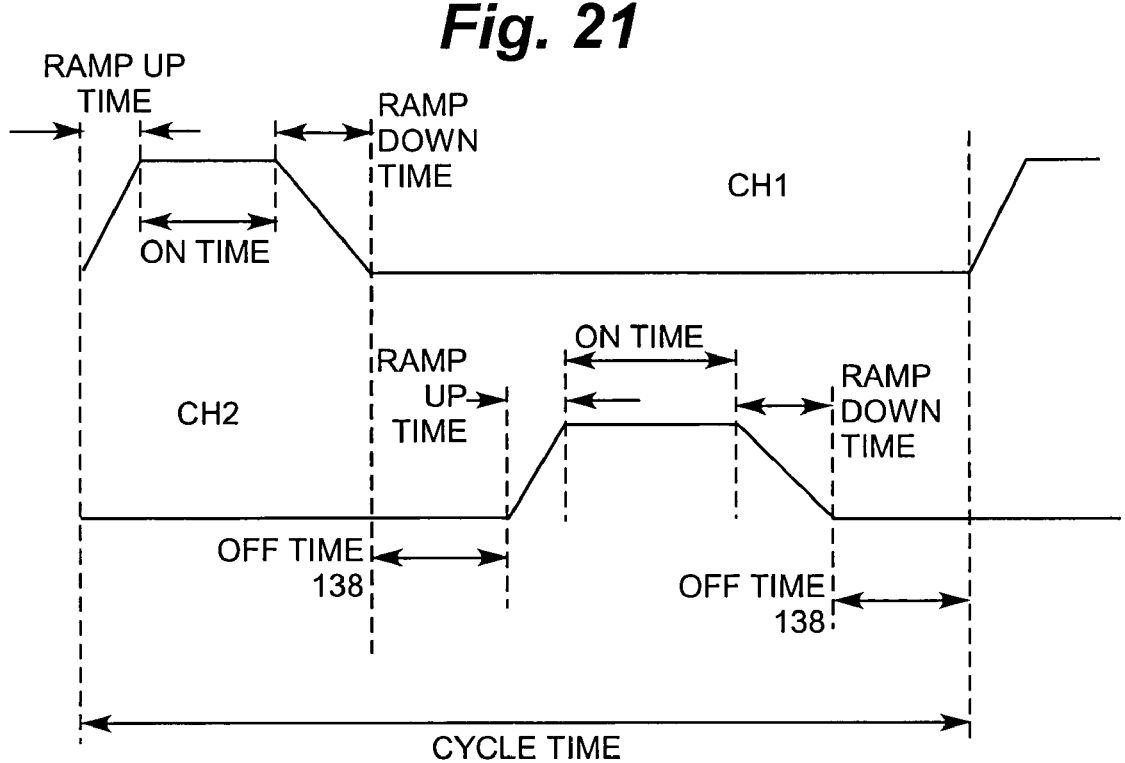
FIG. 21 is a two-channel graph of an alternating treatment cycle according to one embodiment of the invention.

In an alternating treatment cycle, the output for channel 2 starts after the output of channel 1 is completed, as depicted in FIG. 21. As shown, an off time 138 is the time between the end of a channel treatment cycle for channel 1/channel 2 and the beginning of the output of channel 1 for the next treatment cycle.

Figure 22:
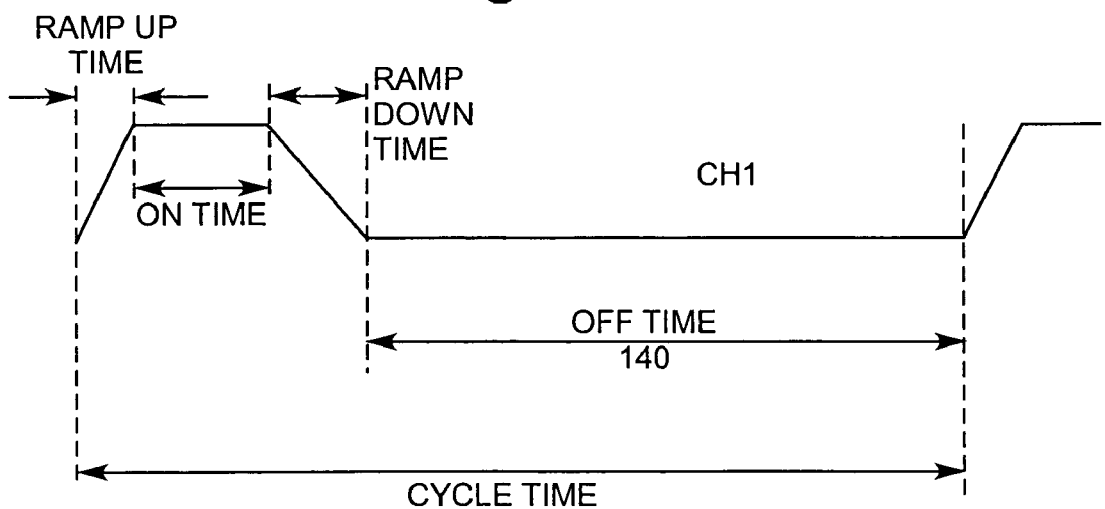
FIG. 22 is a graph of a single channel treatment program according to one embodiment of the invention.

Stimulator 10 can also deliver a single channel treatment program as depicted in FIG. 22. The single channel output will generally be delivered via channel 1, although channel 2 can be used in other embodiments. An off time 140 of a single channel treatment program is defined as the time between the end of a channel 1 treatment cycle and the beginning of the output of channel 1 for the next treatment cycle.

TENS and PDC treatments, including a biphasic output with a DC component, are discussed in U.S. Pat. Nos. 4,640,286; 4,803,988; and 5,117,826, which are incorporated herein by reference. U.S. Pat. No. 4,640,286 discloses an apparatus for achieving optimization of nerve fiber stimulation to thereby increase the overall activity of the nerve fibers then being stimulated. In U.S. Pat. No. 4,803,988, nerve fiber stimulation is provided using plural active electrodes having bi-phased pulses coupled thereto. In each U.S. Pat. Nos. 4,640,286 and 4,803,988, bi-phased pulse pairs have the pulses of each pair separated by a distance, in time, comparable to a refractory period for the particular kinds of nerve fibers being stimulated, with the frequency of repetition and pulse duration being selected to further enhance stimulation. In U.S. Pat. No. 5,117,826, an apparatus is disclosed by which both nerve fiber stimulation and body tissue stimulation can be effected. Nerve fiber stimulation can be effected by application of AC and is preferably effected through application of biphasic pulse pairs having the pulses spaced from one another in a pattern that enhances nerve fiber stimulation, while body treatment can be effected by application of DC, and is preferably effected by a net DC charge resulting from application of biphasic pulses having a greater number of pulses of one polarity.

Figure 23:
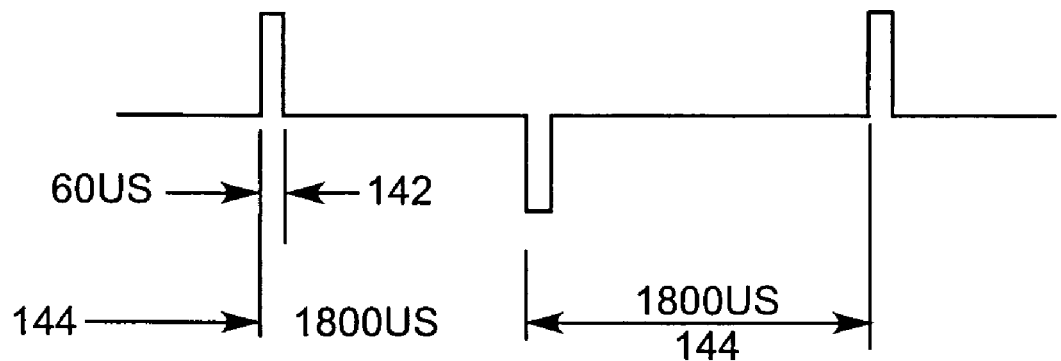
FIG. 23 is a symmetric biphasic square wave pulse of a pulsed direct current treatment modality according to one embodiment of the invention.
Figure 24:
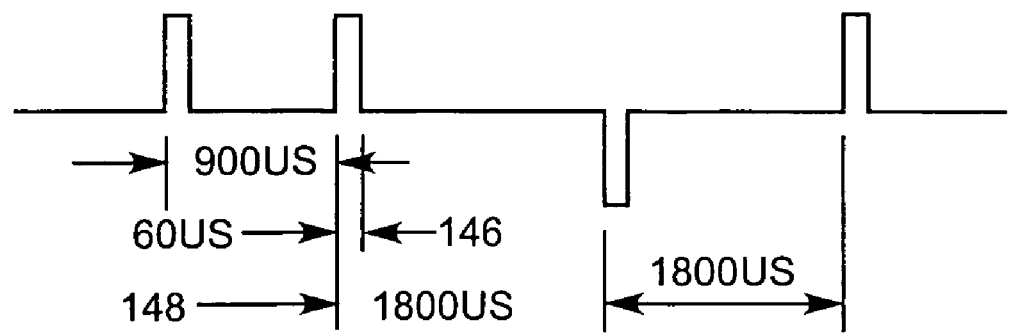
FIG. 24 is a triphasic output waveform of a triphasic pulse of a pulsed direct current treatment modality according to one embodiment of the invention.

Referring to FIG. 23, a PDC treatment modality of stimulator 10 delivers a symmetric biphasic square wave pulse with zero net DC current in one embodiment in which a pulse width 142 is about 60 µs, a positive pulse to negative pulse time 144 is about 1800 µs, and a pulse frequency is about 278 Hz. A PDC treatment modality can also deliver a tri-phasic output waveform of a triphasic pulse, as shown in FIG. 24. In one tri-phasic output embodiment, a pulse width 146 is fixed at about 60 µs, a positive pulse to positive pulse time is about 900 µs, a positive pulse to negative pulse duration 148 is about 1800 µs, and a pulse frequency will be about 222 Hz. A PDC modality output amplitude can be adjustable from about zero to about 100 mA in one mA increments across a 1000-Ohm load independently for each channel. PDC biphasic and triphasic pulses can be combined to give a time average DC microcurrent component of about 300 µA maximum at the set output amplitude for each channel. The DC microcurrent component will be less than about 300 µA at low output amplitudes with 100% triphasic wave being delivered. At these output amplitudes, the extra positive pulse is not large enough to equate to a time average DC microcurrent component of 300 µA. A net DC component can also be achieved in other embodiments by varying or adjusting a pulse width.

Timed PDC modality treatment programs can be programmed in stimulator 10. In one embodiment, a PDC time treatment program duration will be selectable from about 30 to about 60 minutes for all programs, in five minute increments. Stimulator 10 can be programmed to automatically power off at the end of the timed program. Timed PDC treatment programs can be used to treat, for example, acute pain and chronic pain. In an acute pain treatment program, stimulator 10 can show that the dispersive electrode will be attached to the negative lead wire. In a chronic pain treatment program, stimulator 10 can show that the dispersive electrode will be attached to the positive lead wire.

Figure 25:
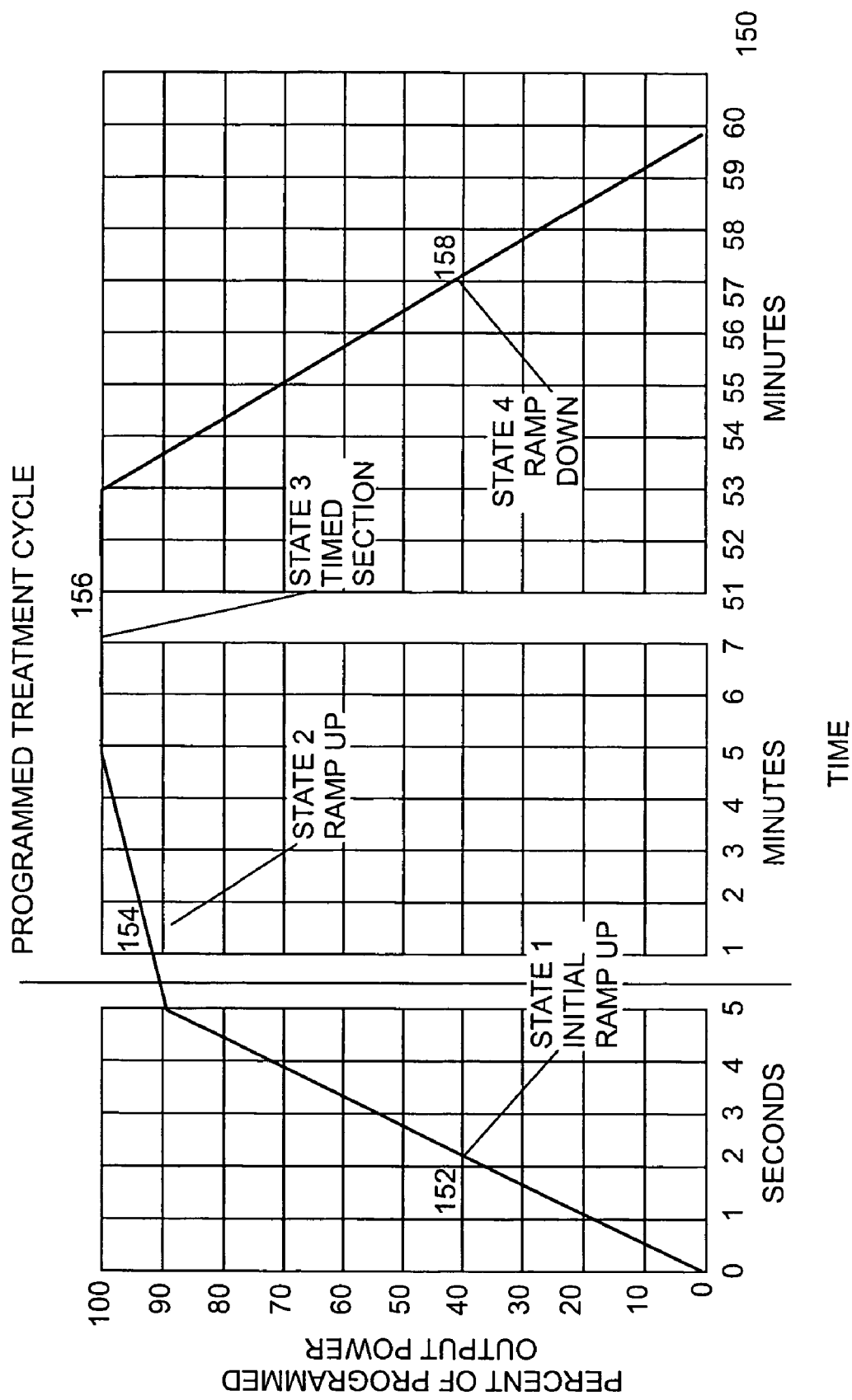
FIG. 25 is a graph of a PDC timed treatment program treatment cycle according to one embodiment of the invention.

FIG. 25 depicts one embodiment of a PDC timed treatment program treatment cycle having a selectable duration 150 as described above. The PDC timed treatment program can have the following output profile:

Ramp up from about zero to about 90% of the maximum set output amplitude in the first approximately five seconds (152)

Ramp up from about 90% to about 100% of the maximum set output amplitude in the next approximately five minutes (154) p1 Operate at about 100% of the set maximum output amplitude for the next approximately 18 to 48 minutes, varying according to a set treatment time (156)

Ramp down from about 100% of the maximum set amplitude to about zero for the last approximately seven minutes of the treatment time (158)

Stimulator 10 powers off

As mentioned above, stimulator 10 can also deliver combination treatment programs comprising the IF modality and the NMES simultaneous modality. In these combination programs, stimulator 10 can internally and automatically switch the electrode connections to transition between IF mode and NMES (SIM) mode without requiring physical repositioning of the electrodes by an operator or user.

At the beginning of one embodiment of a combination program, the output amplitude will default to about zero. To begin a combination program, an operator or user will adjust the IF amplitude to a desired setting. The combination stimulation program will then begin after some brief period of time has passed, for example about two seconds. After the first approximately 10 minutes of the program in an IF mode, the output of stimulator 10 will go to zero. In one embodiment, the user or operator will then be required to adjust the output of both channels to start the NMES (SIM) mode. At the end of the NMES mode, the IF mode will start; the output amplitude will ramp from zero to the set level established or selected for the first IF treatment period in approximately ten seconds.

Particular preset combination programs can be stored in stimulator 10 and made available to a user or group of users and selected or disabled by an operator. The parameters of the preset programs are fixed and thus not generally adjustable or customizable by either an operator or a user in one embodiment. Exemplary preset combination IF/NMES treatment programs are shown below in TABLE 4.

TABLE 4

| TREATMENT | TOTAL TREATMENT TIME | FIRST 20 MINUTES | SECOND 20 MINUTES | LAST 20 MINUTES |
|---|---|---|---|---|
| Low Back Pain | 60 min. | IF Mode<br><br>Sweep:<br>60 to<br>120 Hz<br>Ramp:<br>6 sec. up<br>6 sec. down | NMES SIM Mode<br>80 Hz<br>300 µs<br>pulse width<br>Ramp:<br>Up 2 sec.<br>On 8 sec.<br>Down 2 sec.<br>Off 2 sec. | IF Mode<br><br>Sweep:<br>5 to 10 Hz<br><br>Ramp:<br>12 sec. up<br>12 sec. down |

TABLE 4-continued

| TREAT-MENT | TOTAL TREAT-MENT TIME | FIRST 20 MINUTES | SECOND 20 MINUTES | LAST 20 MINUTES |
|---|---|---|---|---|
| Neck | 60 min. | Sweep: 60 to 120 Hz. Ramp: 6 sec. up 6 sec. down | 80 Hz 300 μs pulse width Ramp: Up 3 sec. On 6 sec. Down 3 sec. Off 2 sec. | Sweep: 1 to 10 Hz Ramp: 12 sec. up 12 sec. down |

To create, program, save, and access various programs as described herein above, stimulator 10 operates as a multi-mode electrical therapeutic stimulator, providing a first user operational interface with a first level of access and a second operator operational interface providing a second level of access. In a user mode, a user can select from the various treatment programs previously created and/or made available by an operator via user interface screens displayed by stimulator 10. Certain program characteristics or output features of stimulator 10 may be customizable by a user in this mode, with additional access selectively provided by an operator, if necessary or desired.

Figure 26:
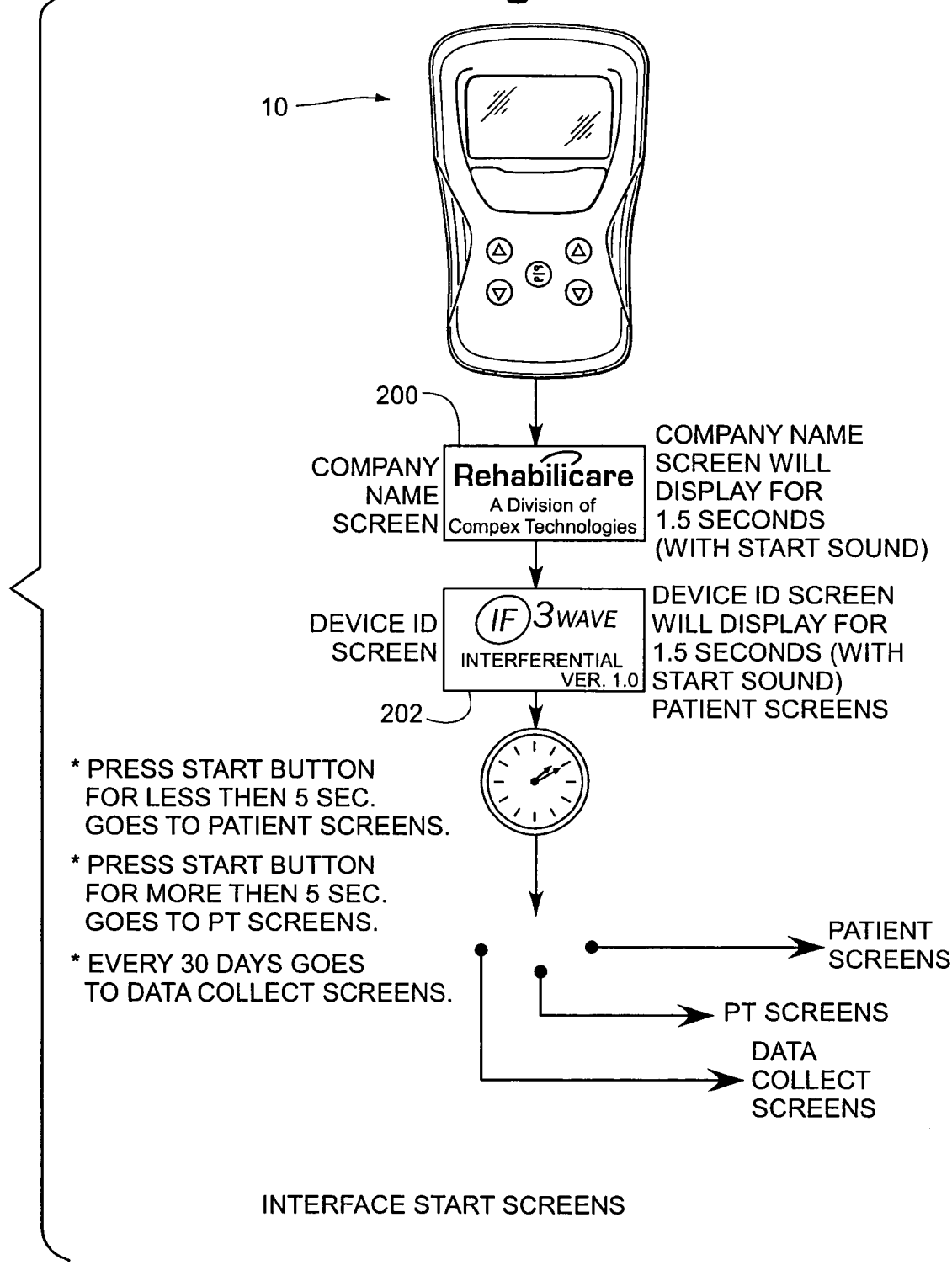
FIG. 26 is a flowchart interface start screens according to one embodiment of the invention.

FIG. 26 is a flowchart of one embodiment of stimulator 10's user interface start screens. When stimulator 10 is initially powered on in normal operation of one embodiment, identification screens are displayed. In one embodiment, a first screen 200 displays corporate or other identification information and a second screen 202 displays device identification information.

In one embodiment, stimulator 10 automatically performs a power-on self-test each time stimulator 10 is powered on. This self-test can include the following individual tests: initiation of power-up sequence by engaging DC power supply; power on check; microcontroller mode operation initialization; read only memory (ROM)/software checksums verification; software initialization; microcontroller register initialization; random access memory (RAM) initialization; internal time base initialization; device check; watch-dog enabled check; boot code version and checksums verification; electrically erasable programmable ROM (EEPROM) write error check; and hardware-software compatibility check. Other initialization and self-tests can also be included in the power-on procedure of stimulator 10.

When stimulator 10 is fully powered on and ready for operation, various options can exist. Briefly depressing a designated input, for example a particular button or combination of buttons, via input portion 18 accesses the user interface, and user screens (refer, for example, to FIG. 27) will load on output portion 16. Depressing and holding the same or another set of buttons or keys on input portion 18 or operator interface 26 can access the operator care professional setup screens (refer, for example, to FIG. 25). Periodically, for example once a week or once every thirty days, stimulator 10 can automatically load in a data collection mode (refer to FIG. 29).

Figure 27A:
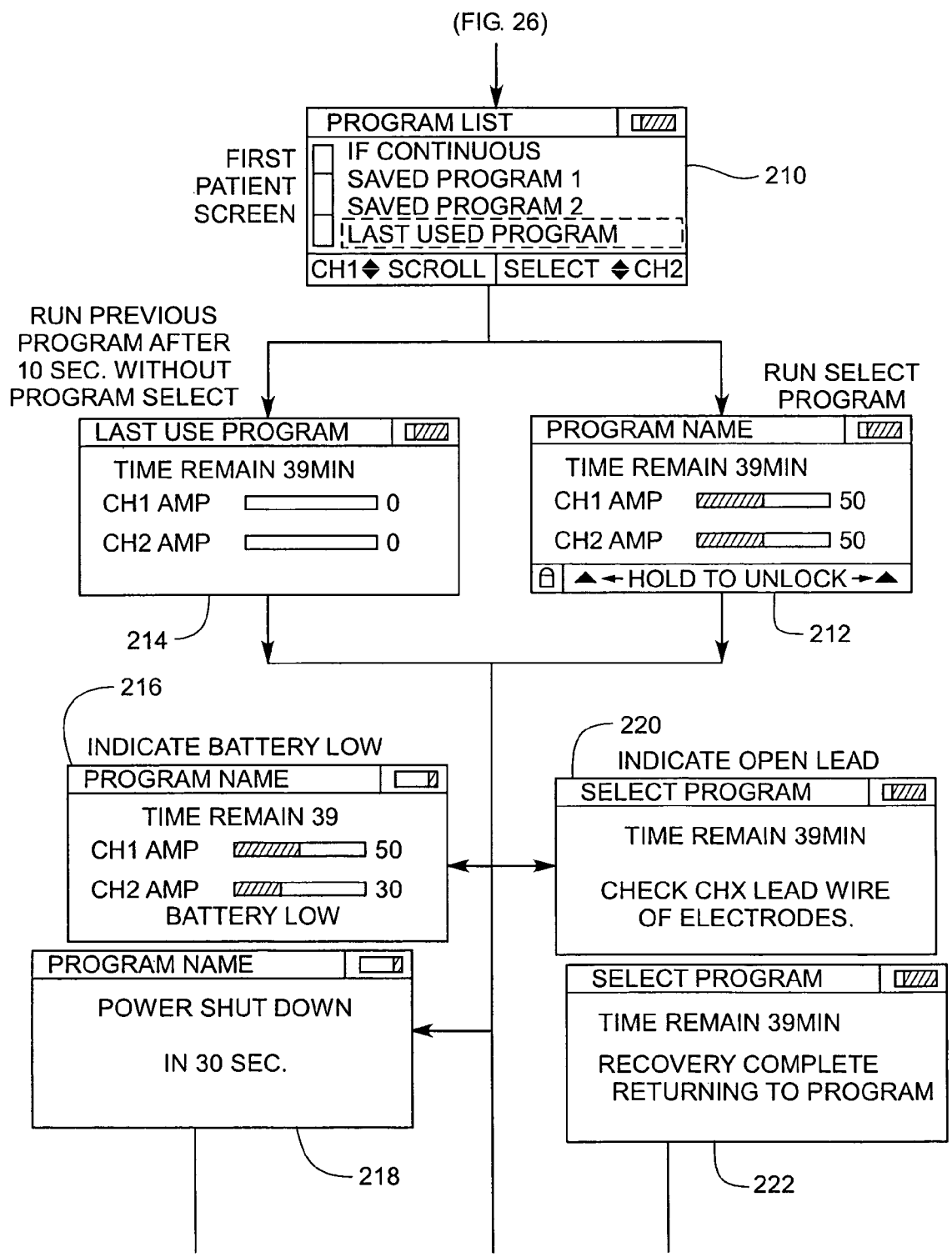
FIG. 27 is a flowchart of patient interface screens according to one embodiment of the invention.
Figure 27B:
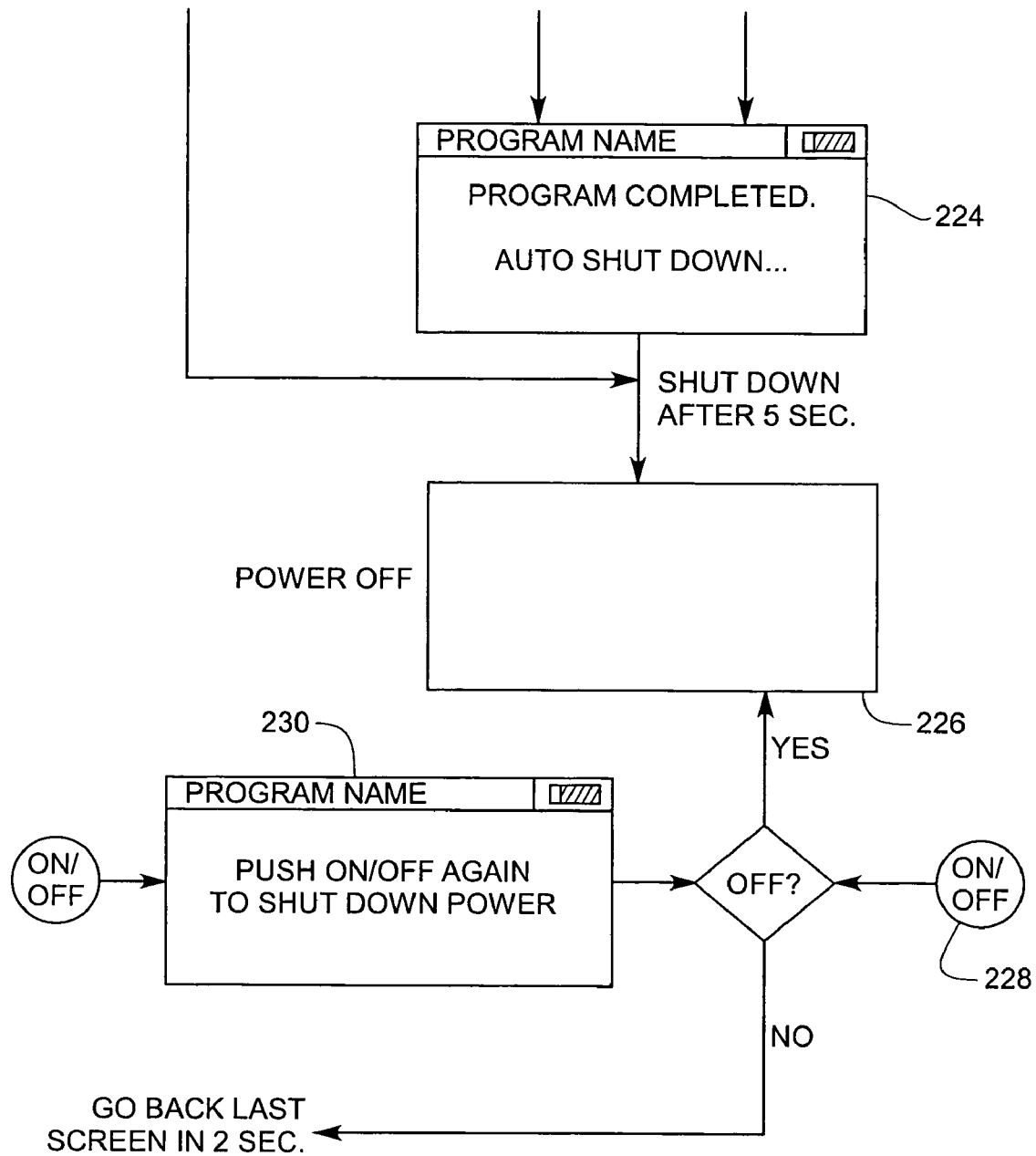
Figure 28C:
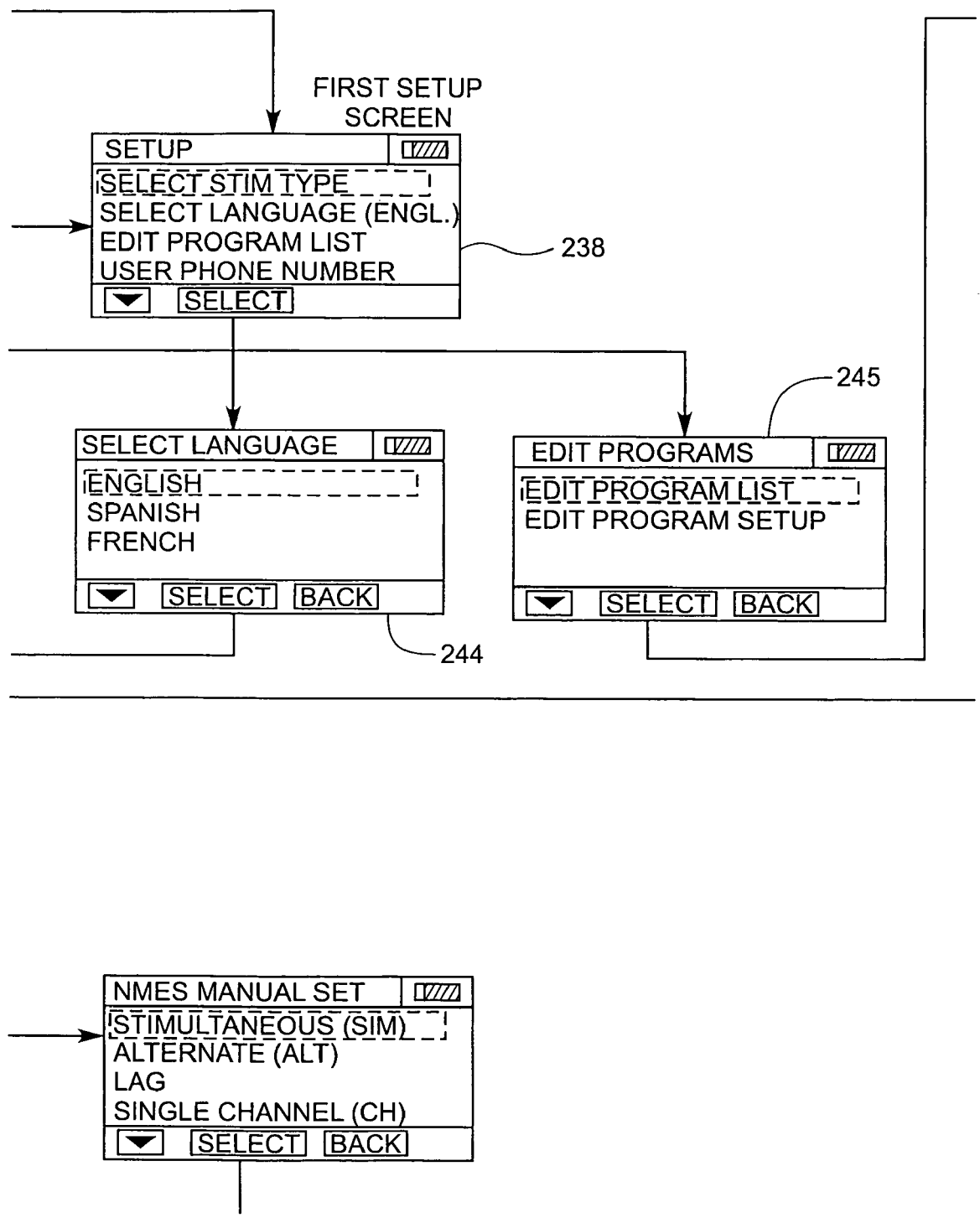
FIG. 28 is a flowchart of operator interface screens according to one embodiment of the invention.
Figure 28D:
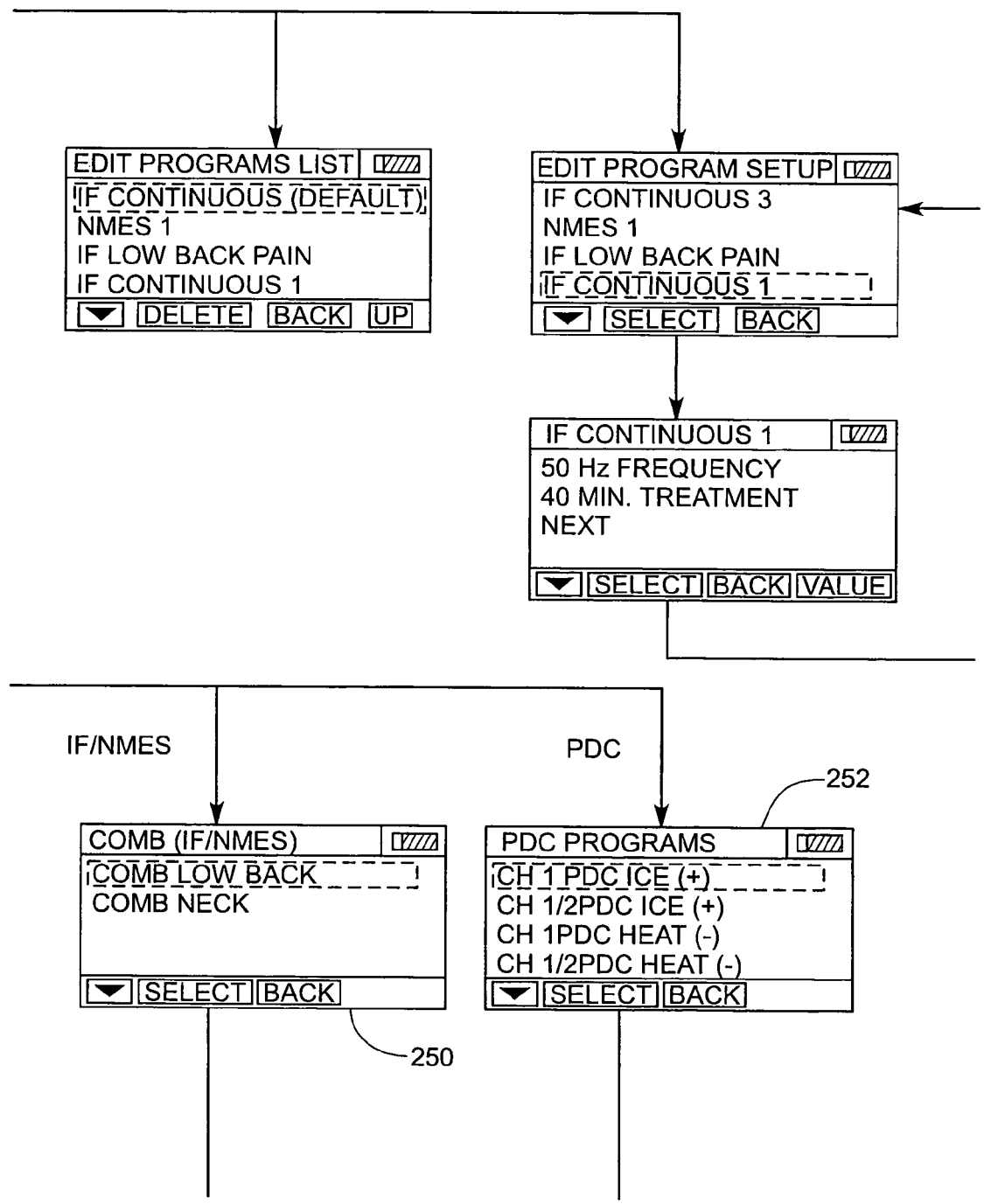
Figure 28E:
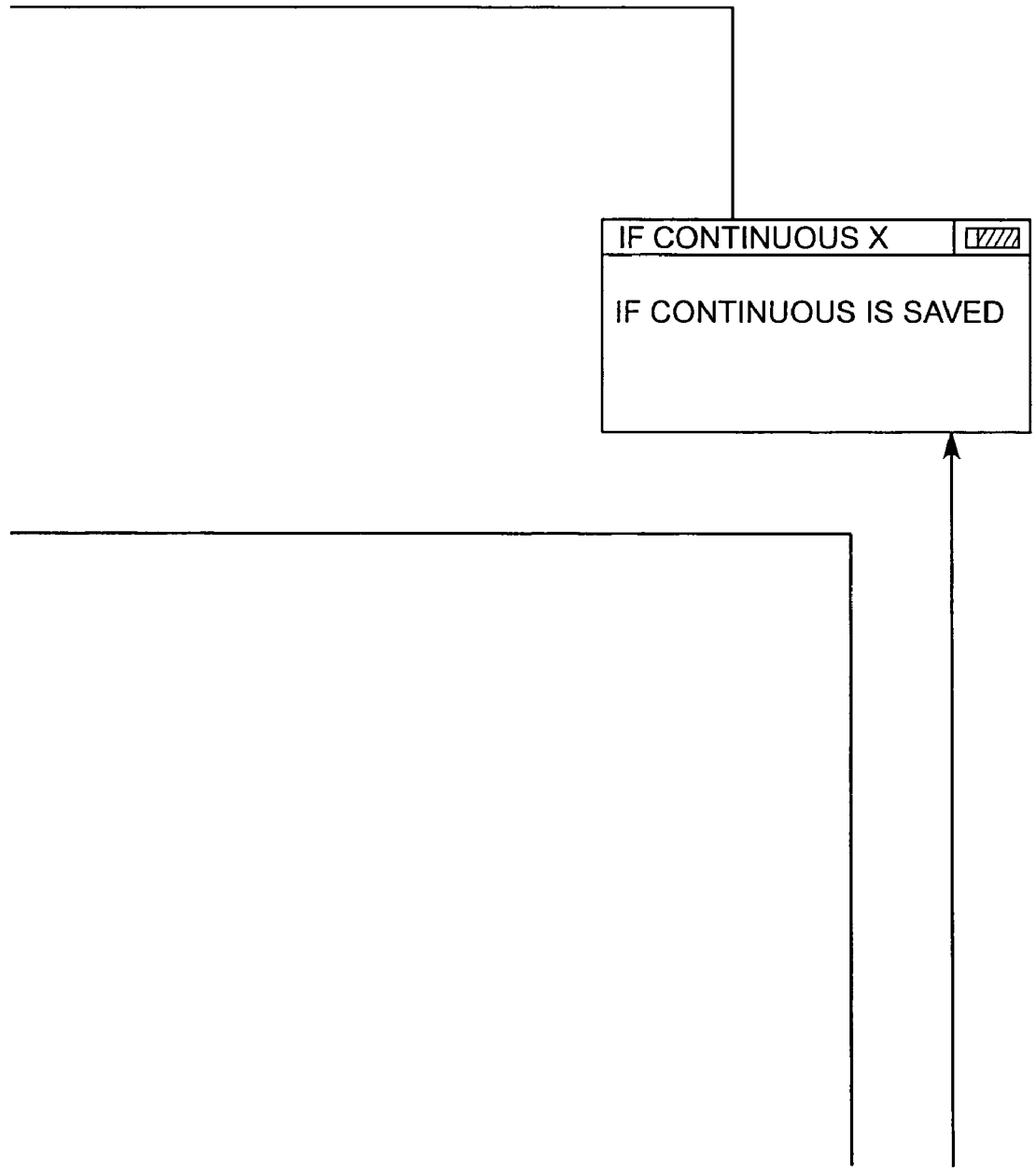
Figure 28F:
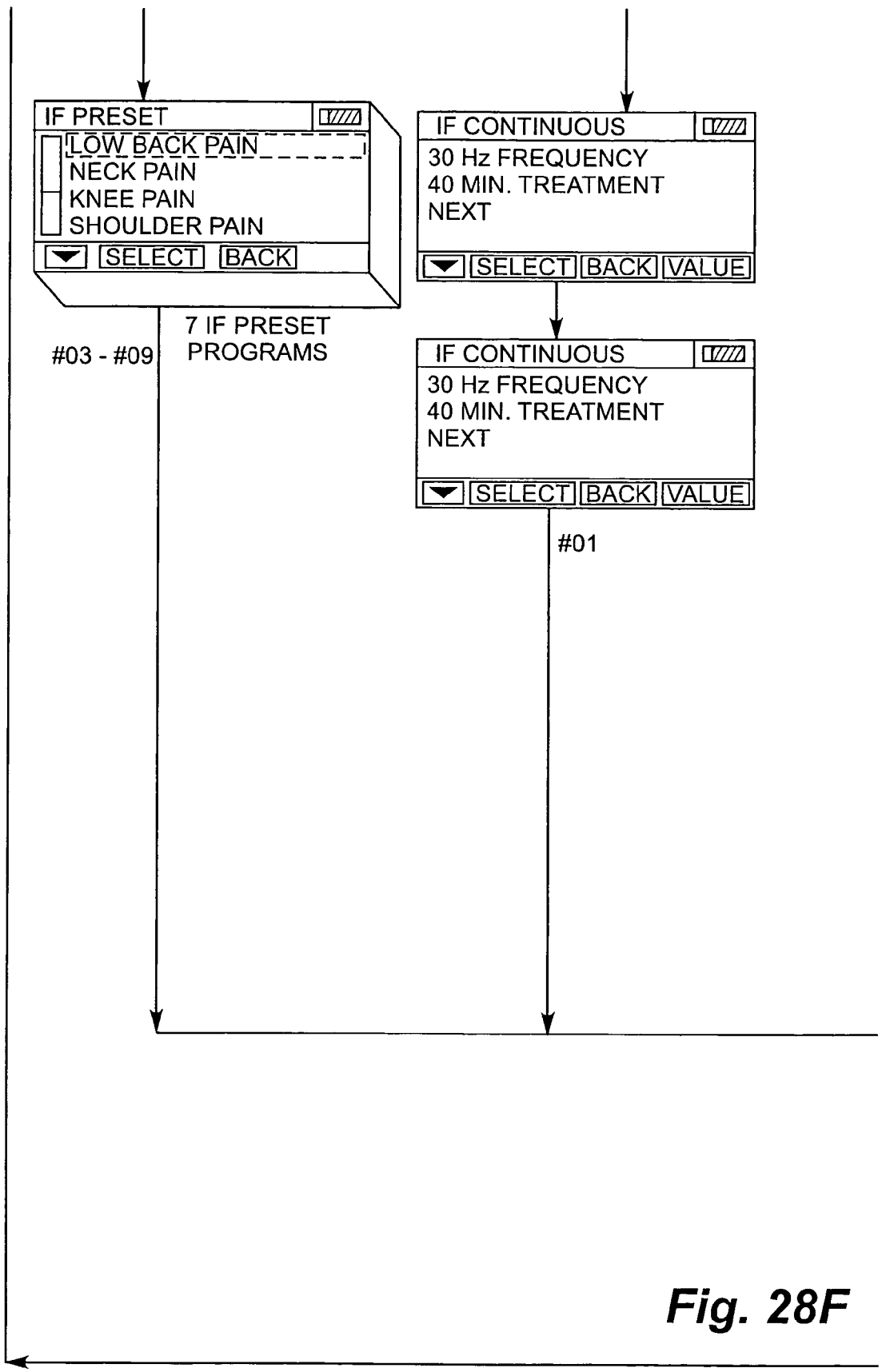
Figure 28G:
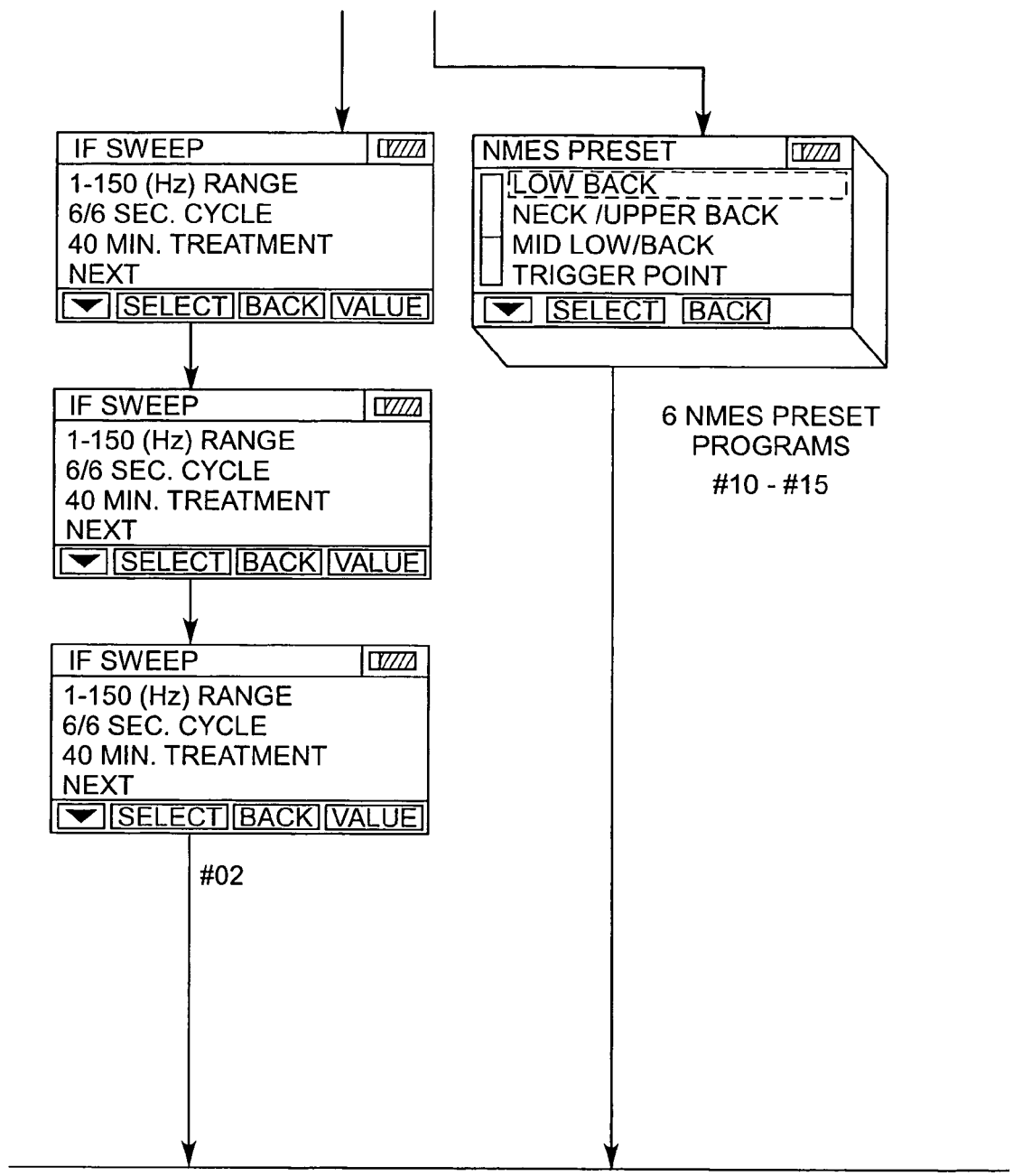
Figure 28H:
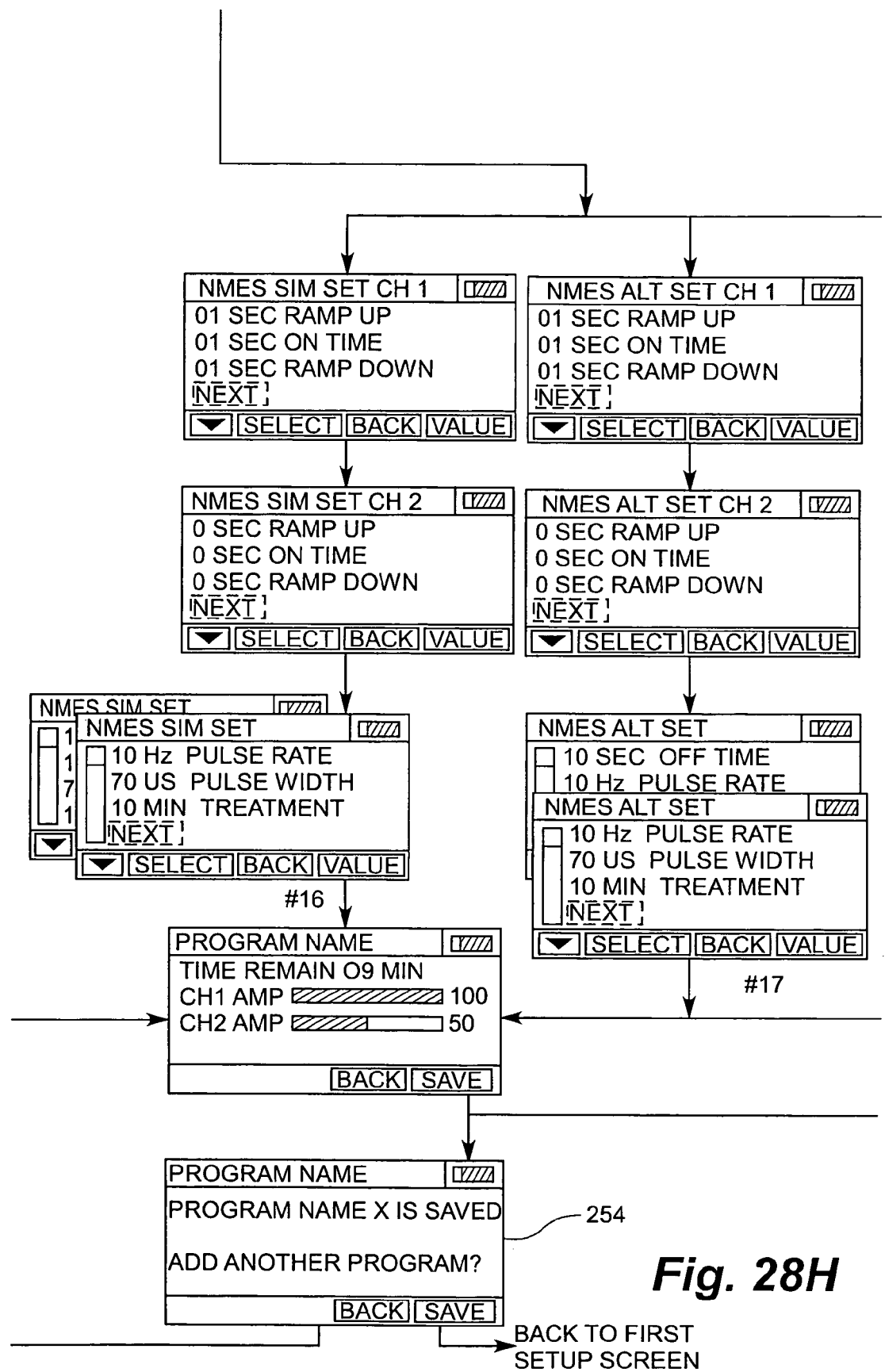
Figure 28J:
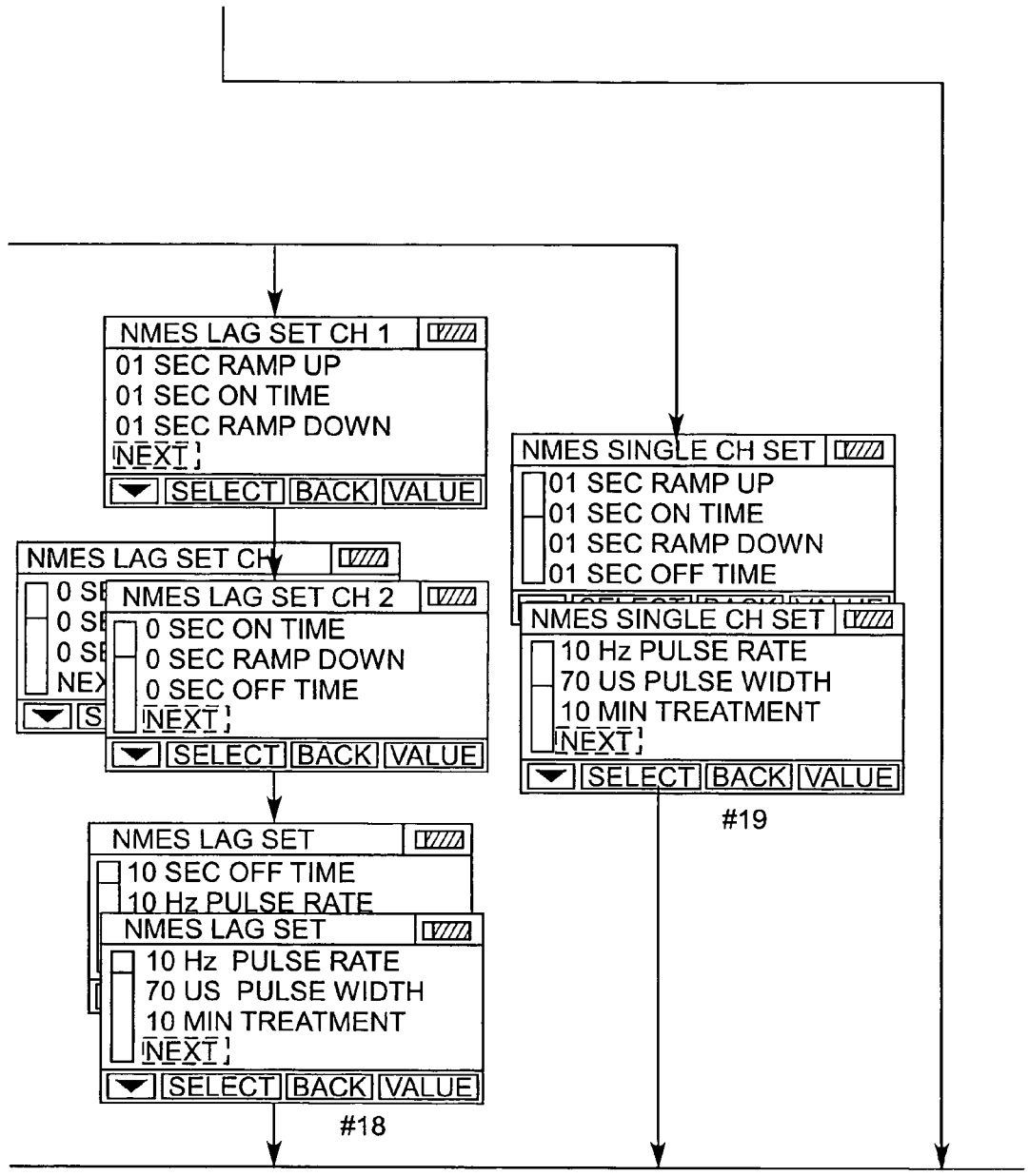
Figure 28K:
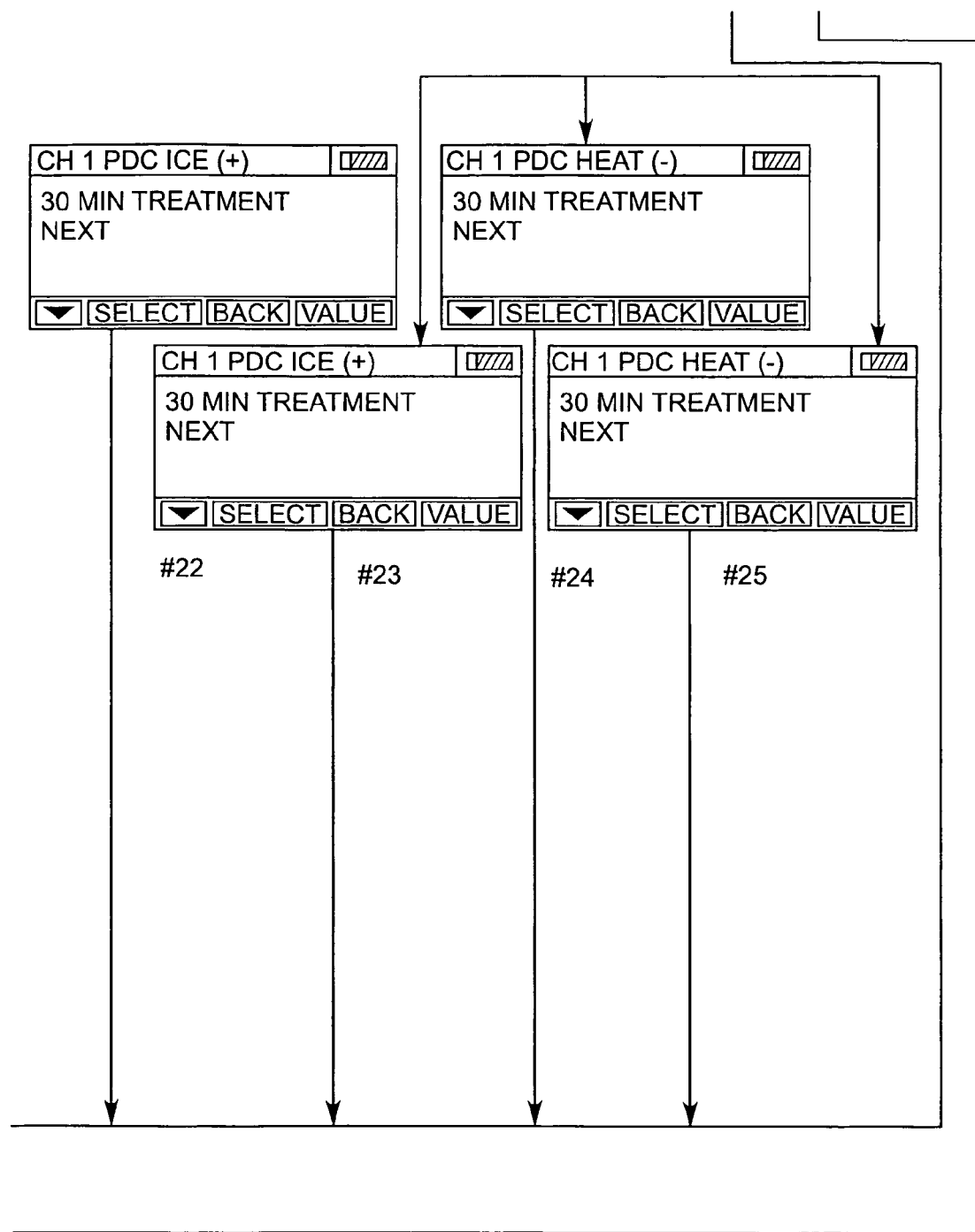

The first mode user interface screens shown in FIG. 27 offer an intuitive, user-friendly instruction, status, and selection interface format by which a user (or an operator) can operate stimulator 10 in accordance with an operator's prescription, treatment program, or recommendations for use. A first patient screen 210 provides a program list. The available programs can be pre-selected and loaded by an operator and can be identified by a modality and treatment program name, for example IF Continuous; a number, for example Saved Program 1 or Saved Program 2; or a use reference, for example Last Used Program. The last program used can be highlighted when the screen 210 first appears in one embodiment.

If a user selects a particular program, stimulator 10 advances to a run selected program screen 212 and displays status information. The status information can include treatment program time elapsed or remaining, battery information, amplitude and other settings for each stimulation channel, and other relevant treatment information. If a program is not user-selected from first patient screen 210 within a selected time, for example approximately ten seconds, stimulator 10 can be programmed to automatically run the last program used (screen 214). The last program can start either with or without certain treatment options selected.

The user interface screens can also include error screens in one embodiment that automatically display if a corresponding error is detected. The error screens can include a "battery low" screen 216, a subsequent power off warning screen 218, an open lead detected screen 220, and a subsequent "returning to program" screen 222. If power button 20 (refer, for example, to FIG. 1) is depressed during a treatment program, stimulator 10 displays an instruction screen 230 advising a user to press power button 20 again if he or she wants to power off stimulator 10.

After a treatment program has been completed, stimulator 10 displays a "program completed" screen 224 and can automatically power off after an elapsed time, for example about five seconds, to conserve battery power (screen 226). Stimulator 10 can also automatically power off in certain situations, for example after an open lead condition occurs and is not corrected by a user or operator within some time period, or at the beginning of a program when no amplitude adjustments have been made above an open lead threshold level within some time period.

Open lead detection serves several purposes. While patient safety in the unlikely situation of a device malfunction is a primary concern, open lead detection also helps to prevent use-related and billing fraud. Some forms of electrical stimulation may cause a patient mild discomfort, and the patient may not want to continue with a prescribed treatment program. Other patients may attempt to misuse a prescription or exaggerate a diagnosis for insurance or work-related fraud. Still others may attempt to share stimulator 10 with friends or family members outside of a necessary physician's prescription. These and other similar misuse, fraud-related, and patient compliance issues are distinct to external, patient-administered medical devices, as preventing such problems and confirming proper usage and compliance are not applicable to implantable, automatically functioning medical devices, such as pacemakers.

In one embodiment, stimulator 10 can be programmed to perform an initial impedance measurement and calibrate that measurement to a particular patient to verify that stimulator 10 is being used by the patient to whom treatment was prescribed. Because an individual's impedance can vary, a tolerance range based upon the initial measurement can be established and a measurement taken prior to the start of each treatment program to confirm that a measured impedance is within the established range. If the measured impedance is out of tolerance, stimulator 10 can be programmed to respond in one of several ways. Stimulator 10 can prompt a user to provide a password or other identifying information to verify that the user is in fact the patient to whom the device was prescribed. Stimulator 10 can also automatically power off. In another embodiment, prior to powering off, stimulator 10 can provide a user with instructions or information. For example, in one embodiment stimulator 10 can be programmed to recommend that a patient contact a device manufacturer or customer care center. This serves as an additional safety feature of stimulator 10 to aid in identifying legitimate device malfunctions.

Stimulator 10 can also be manually powered off via power button 20 (screen 228). In one embodiment of a manual power-off procedure of stimulator 10, output portion 16 displays a message, for example "Push ON/OFF again to shut down power," after power button 20 is initially depressed. If power button 20 is depressed within some amount of time following display of this message, for example two seconds, five seconds, or indefinitely, a power-down sequence is initiated. The power-down sequence can include the steps of setting outputs to zero; saving a user configuration and statistic information; turning off output portion 16; and powering off stimulator 10 by disengaging the DC power supply. Other sequences and steps can also be implemented in a power-down sequence of stimulator 10.

FIG. 28 is a flowchart of one embodiment of the second mode operator interface screens. The operator interface screens and menus include programming and set-up screens that generally should not and will not be available to patient users, although particular screens or portions of screens can be made available to a user or group of users at an operator's discretion. Accordingly, operator interface screens and menus can be password protected to restrict access. Password screen 232 is the first in a series of screens that prompt an operator, or in some circumstances a user, to enter a password in order to access the operator interface screens. The password may be, for example, a three-digit numeric or alphanumeric code. An operator or a user may attempt to enter the correct password three times via an entry screen 233 in one embodiment. After an incorrect entry, a "try again" screen 234 can be displayed and stimulator 10 returns to entry screen 232. After three incorrect entries, stimulator 10 displays the user screens (refer to FIG. 27).

After a correct password is input (screen 236), stimulator 10 advances to a first set-up screen 238. An operator, or possibly a user, then has the option of entering user information 242; selecting operating characteristics, including language 244; editing a program list or setup (screen 245, which accesses a subsequent menu and screen series); and selecting a stimulation type (screen 240) and programming stimulator 10 in accordance with one of the available modalities (initial screens 246, 248, 250, and 252, which access subsequent menus).

The interface screens that follow the modality screens 246, 248, 250, and 252 enable an operator to select various treatment program characteristics and customize or delete the programs. The various program characteristics available for each modality are described in more detail above. After a program is edited or created and subsequently saved, stimulator 10 displays a program screen 254 that enables an operator to return to first set-up screen 238, or to stimulation type selection screen 240.

Figure 29A:
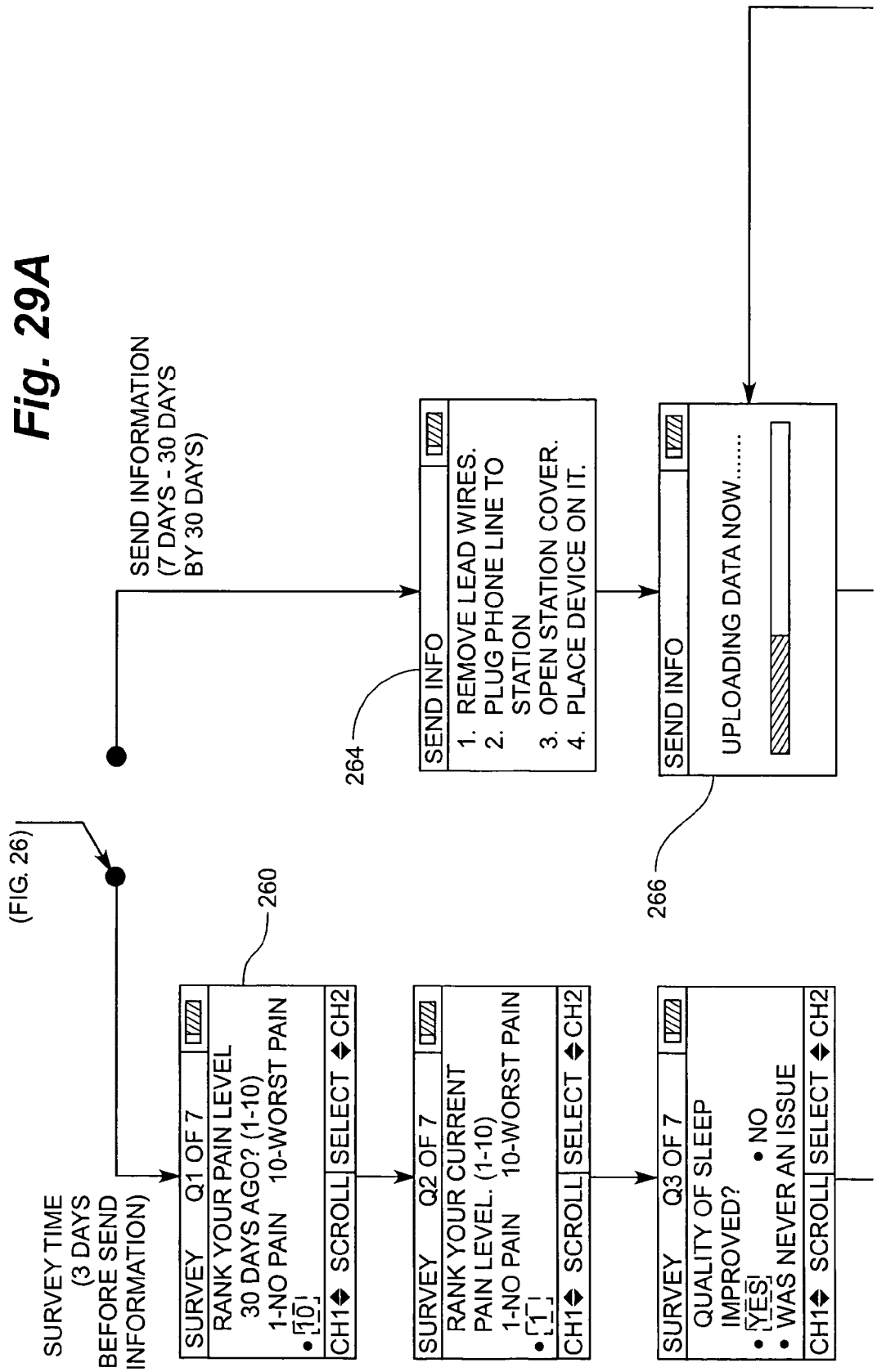
FIG. 29 is a flowchart of data collection interface screens according to one embodiment of the invention.
Figure 29B:
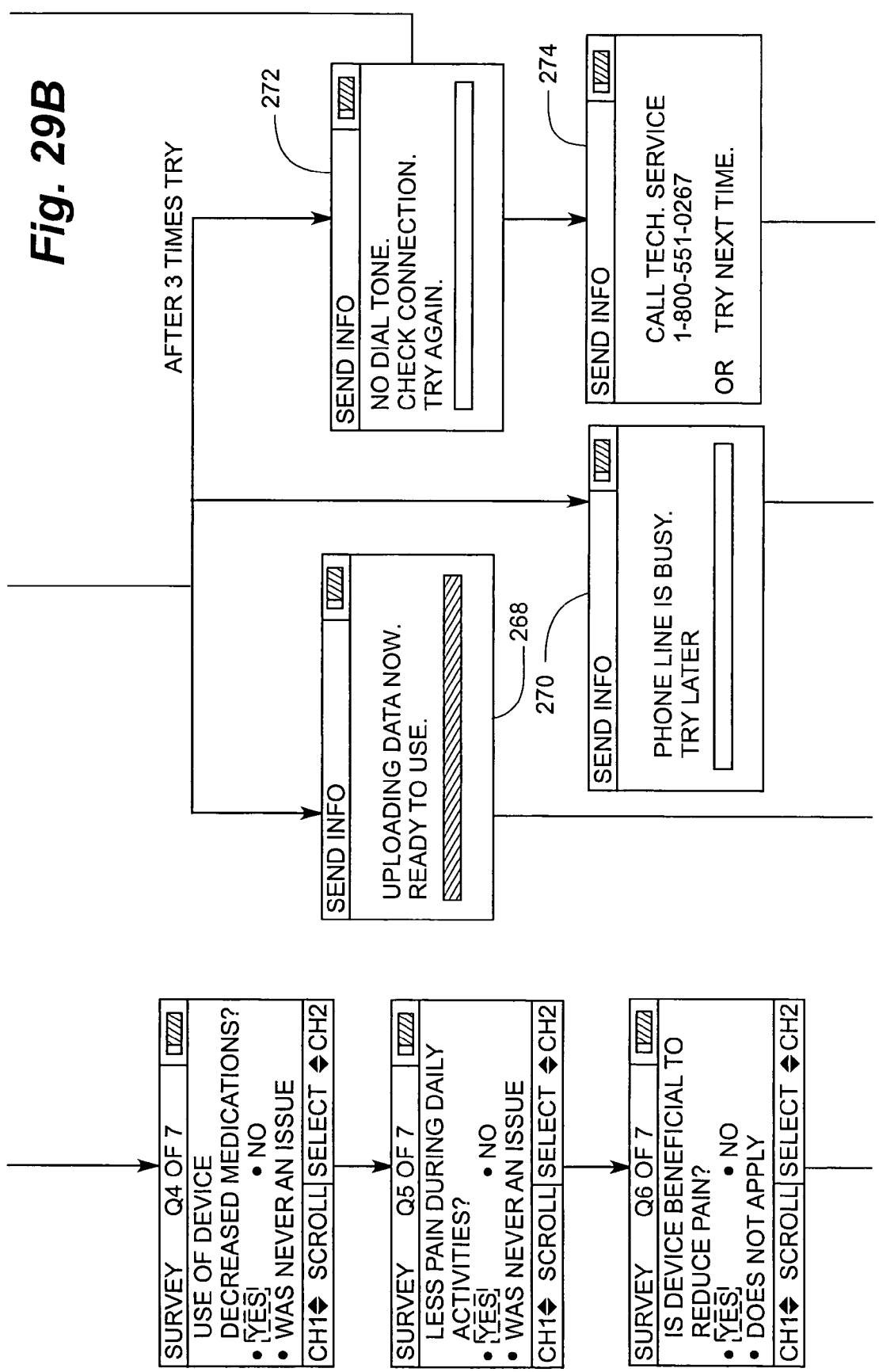
Figure 30:
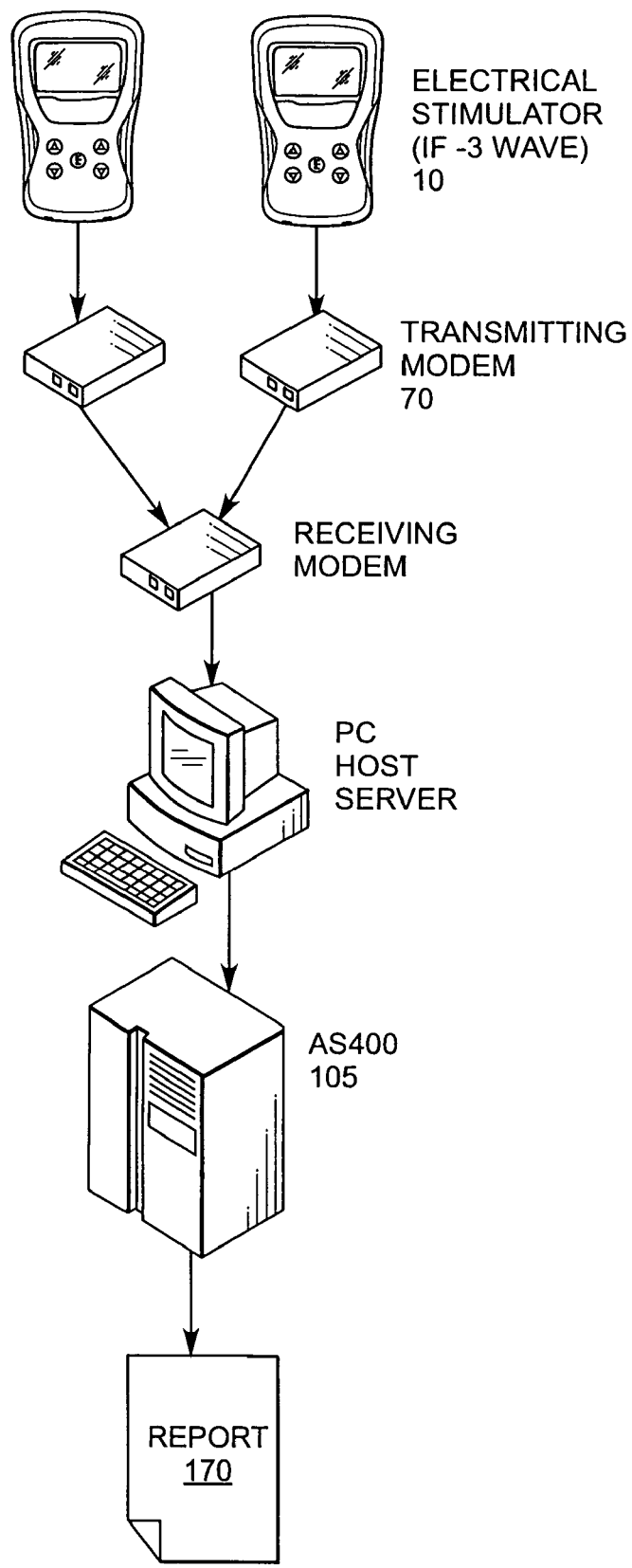
FIG. 30 is a flowchart of a data collection and management system according to one embodiment of the invention.
Figure 33:
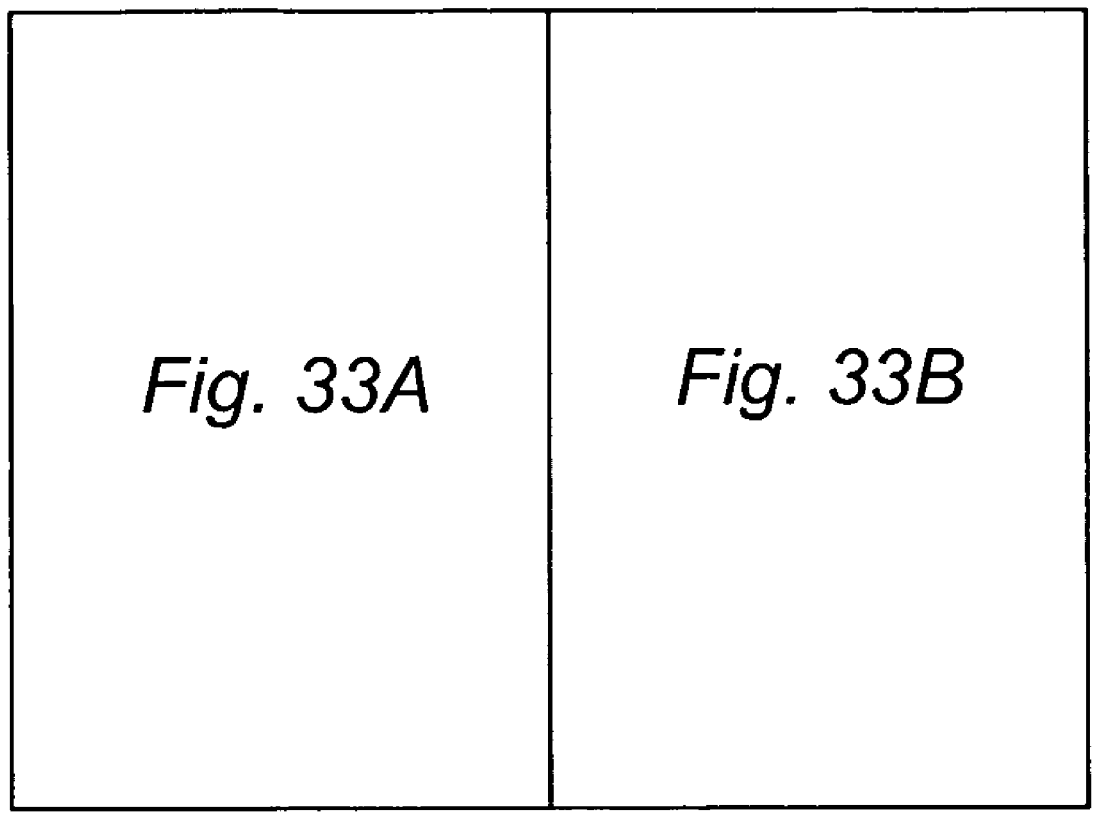
FIG. 33 is a report according to one embodiment of the invention.

FIG. 29 is a flowchart of one embodiment of the data collection screens and FIG. 30 is a flowchart of one embodiment of a data management system according to the invention. Stimulator 10, via battery charger and modem device 70 or other communication methods and devices, can periodically report treatment, compliance, and other data and information for a particular stimulator 10 and user to provide an operator, clinician, insurer, or other monitor with access to quantitative usage data to monitor progress and compliance.

In one embodiment, the data and information is uploaded to database 105, to be subsequently formatted or organized into a report 170 for forwarding to or access by a clinician, user, or other individual involved in the treatment process. Stimulator 10 can therefore provide a detailed reporting of daily patient usage data to verify or document compliance with a prescribed therapy. Uploaded data can then be used to track treatment progress, identify milestones, confirm effectiveness, and monitor status of stimulator 10.

In addition to quantitative usage data, uploaded data and information can also include subjective qualitative data. Several days before reporting data to a central database, which can be part of a customer care center affiliated with a device manufacturer, sales representative, medical facility, insurer, and/or the like, stimulator 10 can survey a user for pain and quality of life information via a series of user interface screens beginning with screen 260 in one embodiment. The survey typically includes yes/no and comparison questions that can be customized or disabled by an operator or other use monitor in one embodiment. For example, the survey may include questions such as, "Less pain during daily activities?" and "Rank your current pain level (1-10)." After a user has completed the survey, stimulator 10 returns to the patient screens (refer to FIG. 27). When stimulator 10 is docked in communication with battery charger and modem device 70, modem device 70 checks to see whether it is time to upload data and, if so, connects to telephone line 100 (refer to FIG. 9) and uploads the data. An initial instruction screen 264 is provided to advise a user of the upload and a status bar screen 266 displays during an upload; user input, however, is not required to initiate the upload in one embodiment. In one embodiment, usage data is uploaded in addition to or instead of the survey results to verify compliance with a prescribed treatment program, for example.

After the upload process is complete, stimulator 10 reports a successful upload (screen 268) and returns to the user interface screen menu (refer to FIG. 27). Error screens are displayed if a telephone line is busy (screen 270) or if a connection could not otherwise be established (screen 272). Stimulator 10 can also display a technical service contact screen 274 with a prompt to contact technical service in an error situation.

The uploading process is preferably completed periodically, such as once a month or more or less frequently as desired by a clinician or as necessitated by a particular treatment plan or reimbursement schedule. Stimulator 10 can automatically prompt a user to complete the aforementioned survey and dock stimulator 10 for uploading. In one embodiment, if an uploading event does not occur as scheduled or expected, for example on a particular day or within a particular time window, a status indicator of a patient's file in database 105 is changed and a customer care center and/or clinician is alerted to contact the patient.

In one embodiment, one or more customized reports 170 can be prepared based upon a patient's uploaded data and information and used to support medical decisions, request or substantiate insurance reimbursement, and verify availability of related supplies based upon usage. The reports can be formatted or otherwise customized for an intended recipient, which could be a clinician, medical professional, patient, insurer, sales representative and the like, and can be made available electronically, i.e., online, or forwarded to appropriate recipients. Clinicians may then analyze the reports, which can include both quantitative and qualitative data, to formulate and support decisions about a patient's treatment and overall care path.

For example, the reports can help to facilitate interactive patient file management among the many individuals who are often involved in a patient's treatment cycle. In one embodiment, central database 105 to which data and information is uploaded facilitates Internet-based patient file management. In an Internet-based system, files, and the reports and other information they contain, can be used by a variety of people in a patient's treatment cycle for a variety of difference purposes: a physician may access and view a patient's file for medical and treatment purposes; a medical device sales representative may view usage and service reports to ascertain necessary equipment service and availability of related supplies and to identify any areas of customer dissatisfaction with device function and performance; an insurer may view usage and other reports for billing and reimbursement purposes; and a patient may be provided access to some or all of their file and reports for information and treatment purposes, for example to leave more detailed comments for a caregiver or to receive updates regarding a treatment program, and also to assist in engaging the patient in the treatment cycle. Other individuals and groups may also be provided access to files or specific reports or information as appropriate.

The reports generated can therefore be tailored and customized for a specific audience or purpose to provide and emphasize necessary data and information of particular interest. Reports can be automatically generated upon uploading of data and information to the central database and can also be automatically delivered, for example by email, computerized fax, generation of hardcopy reports for mailing, and other similar delivery methods. In other embodiments, reports can be created or generated on-demand, and custom reports can be set up manually as needed or desired.

FIG. 31 depicts one example of a patient report 172 generated from uploaded data. Report 172 includes patient identification information 173, physician information 174, and usage information 175. Usage information 175 can include a treatment program modality 176, total usage 177, and other information of interest related to a user's treatment and implementation and of a prescribed program. FIG. 32 includes additional data of total treatment times 178 for each modality 179, organized by each day 180 and FIG. 33 includes a more detailed breakdown of usage data and information.

Referring to FIGS. 34 and 35, reports and other documents can incorporate trend analyses of qualitative and quantitative data for use by a physician, clinician, insurer, or others. Reports can therefore comprise text, graphics, and other information as needed or desired. For example, FIG. 34 includes a spreadsheet summary report 181 that includes a program name 182, percentage of use 183, treatment times for morning 184 and night 185, a percentage of treatment time associated with a particular time 186, and a summary graph 187 for a particular program based on a plurality of previous reports. The chart 188 of FIG. 35 includes summary treatment data 189 and qualitative data 190 based upon user survey responses.

Figure 36:
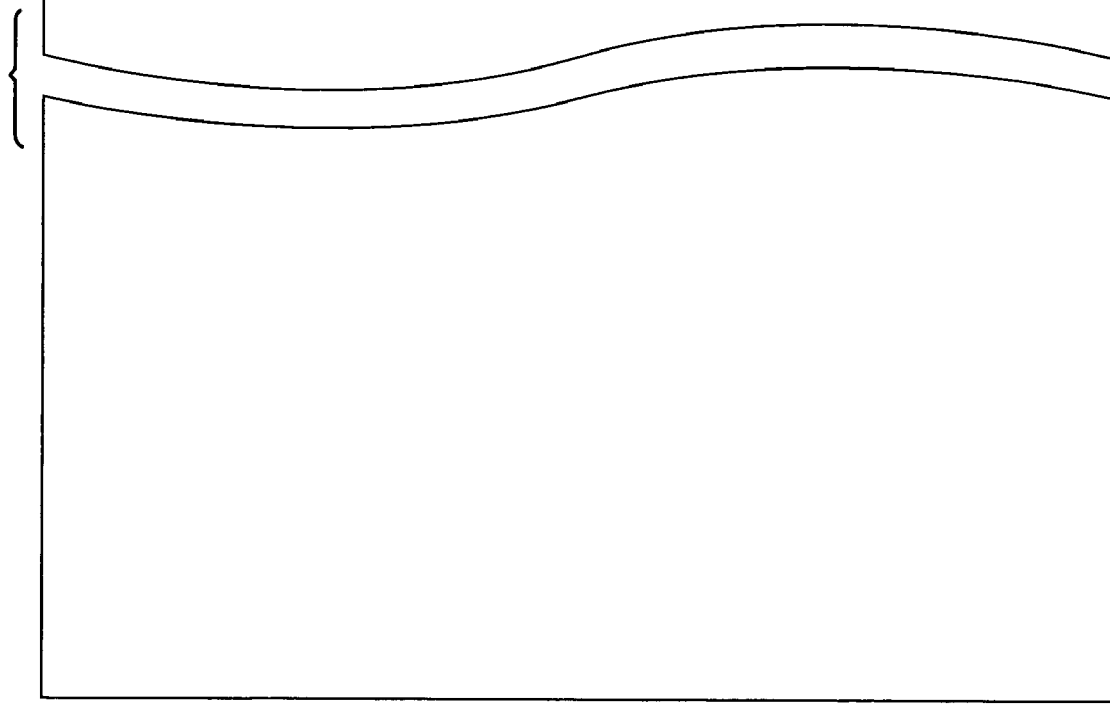
FIG. 36 is a report according to one embodiment of the invention.

As previously discussed, database 105 can identify and match uploaded data according to a device serial number and patient telephone number. FIG. 36 is one embodiment of a report generated automatically by database 105 when uploaded data cannot be matched to an existing patient file. The report identifies the telephone number 191 from which the data was received and the serial number 192 of the device associated with the data and indicates that a matching record could not be located. Such reports can then be manually matched or otherwise associated with a patient file.

Figure 37:
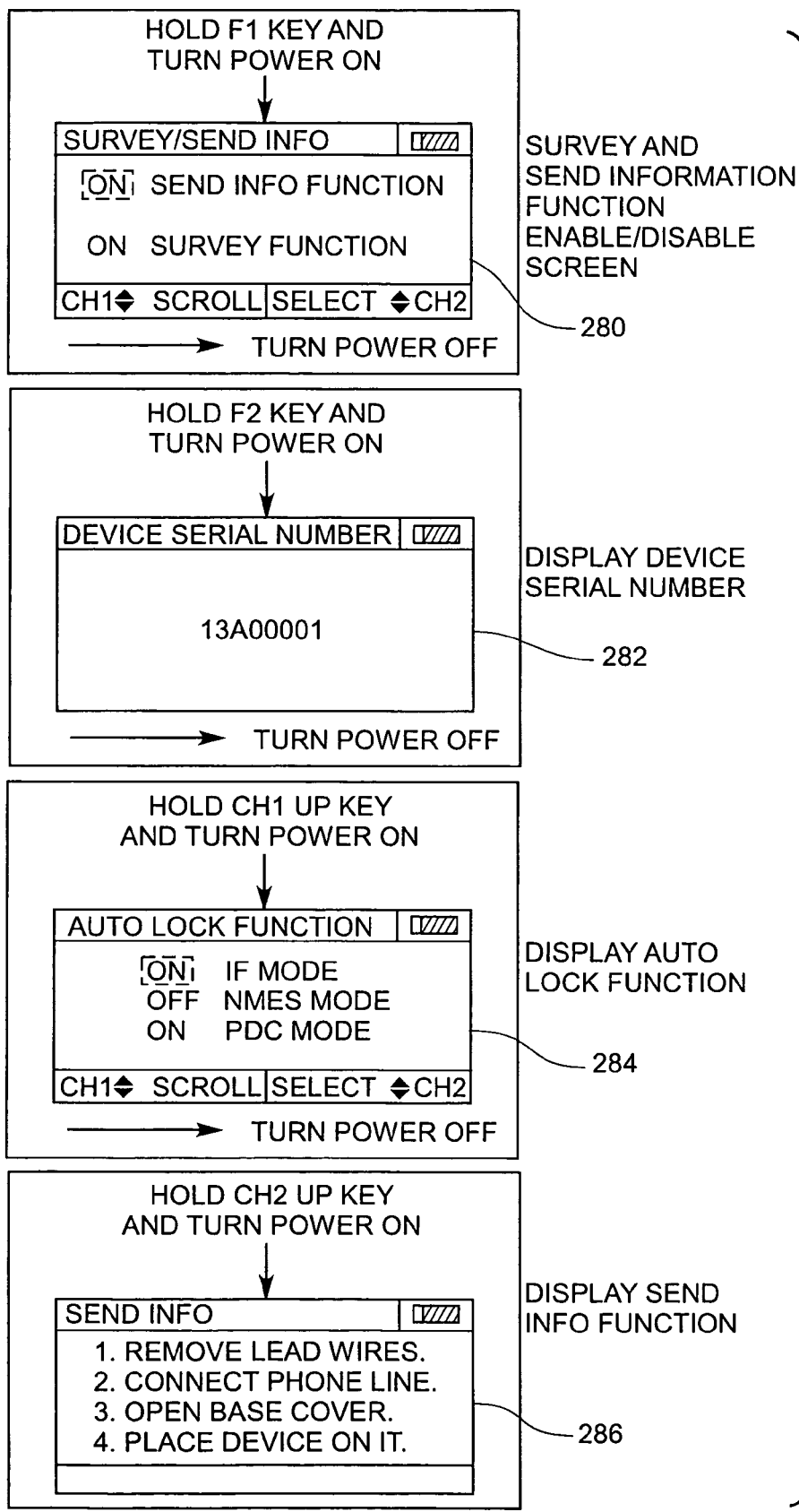
FIG. 37 is a depiction of special function interface screens according to one embodiment of the invention.

Referring to FIG. 37, stimulator 10 can also include special function screens. For example, the survey and send functions described above with reference to FIG. 29 can be disabled or enabled via user interface screen 280. Screen 282 displays a stimulator device serial number. Each stimulator 10 can be assigned to a particular patient and tracked by the serial number. In one embodiment, each stimulator 10 can also be tracked by a patient phone number and cross-checking can be performed when data is uploaded from stimulator 10 to a central database to ensure data is properly matched to a patient file and to help reduce use-related and billing fraud. Screen 284 provides an interface through which an operator can lock or unlock one or more of the available treatment modes for a particular user or group of users. Screen 286 displays a send info function, which in one embodiment includes user instructions for connecting stimulator 10 to a phone line to effect transmission of information. Each of the special function screens 280, 282, 284, and 286 can be accessed via a particular key combination or access code that will generally not be known or easily accessed by a user in one embodiment. Other special function screens can be included for various other options or desired customizations.

In one embodiment, stimulator 10 comprises an auditory prompt and recording/voice recognition system. Audible prompts can be provided with some or all of the operator and user interface screens to indicate that a new screen is displayed, that input is required, or that some other change or status indicator requires attention. Audible prompts can also be used with the data collection screens. A particular sound output by stimulator 10 can indicate that information is requested or a verbal recording of the survey questions could be used. Stimulator 10 can also audibly or visually remind a user that a treatment session is due or overdue according to a prescribed and programmed regimen.

In a related embodiment, stimulator 10 can include a recording/voice recognition system comprising an external microphone device for collecting audible oral responses. For example, in an audible implementation of the survey, stimulator 10 outputs pre-recorded questions and a user orally answers. The recording system, which can include voice recognition software, stores the responses for uploading. Any combination and other applications of auditory prompts, visual prompts, recording, data entry, and voice recognition can be implemented in other embodiments of the invention, customized for a particular user or application.

Stimulator 10 can also be programmed with other beneficial features to improve ease of operation by a user and supervision by an operator. In one embodiment, stimulator 10 can be programmed by an operator with a specific prescription or treatment regimen, whereby stimulator 10 can prevent a user from over-using stimulator 10 by not delivering more than a timed dosage or particular number of treatment sessions in a given period of time. In another embodiment, stimulator 10 can be programmed to provide a treatment summary screen. The screen can be displayed automatically, for example upon start up or after completion of a stimulation treatment session, or on demand. The screen can include usage information, such as the last date and time of use, the length of the treatment program, the total number of minutes the device was used, and other information as needed or desired. This feature can be of particular convenience for health care aides or family members to confirm whether a user is complying with a prescribed treatment program or otherwise properly using stimulator 10.

The invention may be embodied in other specific forms without departing from the spirit of the essential attributes thereof; therefore the illustrated embodiment should be considered in all respects as illustrative and not restrictive, reference being made to the appended claims rather than to the foregoing description to indicate the scope of the invention.

The invention claimed is:

1. A multi-mode electrical therapeutic stimulation system comprising:
  a plurality of electrodes adapted to deliver a stimulation treatment program to the tissue of a user; and
  an electrical stimulation device operably coupled to the plurality of electrodes, the electrical stimulation device including—
    internal circuitry electrically connected to the plurality of electrodes and operable to automatically switch between a first electrode electrical configuration and a second electrode electrical configuration as required to deliver the stimulation treatment program;
    a user interface system having a first access level for a user;
    an operator interface system having a second access level for an operator; and
    wherein the operator interface system includes the user interface system, the user interface system is adapted to accept a first input set from the user, and the user interface system and the operator interface system are adapted to accept a second input set from an operator, the second input set controlling a function of the stimulation treatment program not accessible via the first input set.

2. The multi-mode electrical therapeutic stimulation system of claim 1, wherein the second access level includes a selection portion and a customization portion of the stimulation treatment program, and wherein the second input set comprises a customizable characteristic of the stimulation treatment program.

3. The multi-mode electrical therapeutic stimulation system of claim 2, wherein the first access level includes a stimulation treatment program selected in the second access level.

4. The multi-mode electrical therapeutic stimulation system of claim 3, wherein the stimulation treatment program selected includes a customizable characteristic selected and made available to the first access level in the second access level.

5. The multi-mode electrical therapeutic stimulation system of claim 4, wherein the characteristic includes a program, signal frequency, a first adjustable energy range, a time, a pulse width, and a stimulation intensity.

6. The multi-mode electrical therapeutic stimulation system of claim 2, wherein the second input set includes the first set of data and information.

7. The multi-mode electrical therapeutic stimulation system of claim 2, wherein the stimulation treatment program comprises an interferential (IF) mode, a neuromuscular electrical stimulation (NMES) mode, a combination IF/NMES mode, or a pulsed direct current (PDC) mode.

8. The multi-mode electrical therapeutic stimulation system of claim 2, wherein the selected treatment mode comprises a combination IF/NMES mode.

9. The multi-mode electrical therapeutic stimulation system of claim 8, wherein the first electrode electrical configuration is a cross-position IF configuration, and the second electrode electrical configuration is a parallel NMES configuration.

10. The multi-mode electrical therapeutic stimulation system of claim 1, further comprising a battery charging and communication device.

11. A method of providing therapeutic electrical stimulation by having a multi-mode electrical therapeutic stimulation system perform the steps of:
  providing an operator interface of a multi-mode electrical therapeutic stimulation system;
  accepting a first set of data via the operator interface;
  providing a user interface of the stimulation system while restricting access to the operator interface;
  accepting a second set of data via the user interface;
  defining a stimulation treatment program based at least in part on the first set of data and the second set of data;
  applying a plurality of electrodes to a target treatment area of a user;
  automatically switching an electrical configuration of the plurality of electrodes; and
  delivering the stimulation treatment program to the target treatment area.

12. The method of claim 11, wherein the step of accepting the first set of data comprises accepting at least one available stimulation treatment program, the step of accepting the second set of data comprises accepting a stimulation treatment program selection, the selection made from the at least one available stimulation treatment program.

13. The method of claim 12, wherein the at least one available stimulation treatment program comprises an interferential (IF) mode, a neuromuscular electrical stimulation (NMES) mode, a combination IF/NMES mode, or a pulsed direct current (PDC) mode.

14. The method of claim 13, wherein automatically switching an electrical configuration of the plurality of electrodes comprises automatically switching between an IF mode configuration and an NMES mode configuration when the delivered stimulation treatment program comprises a combination IF/NMES mode.

15. The method of claim 11, further comprising the steps of:
  presenting a treatment effectiveness survey;
  accepting a survey response; and
  storing the survey response.

16. The method of claim 15, further comprising the step of:
  periodically transmitting stimulation system usage data to a central database, wherein the system usage data comprises the survey response and qualitative usage data.

17. The method of claim 16, further comprising the step of:
  generating a report based at least in part upon the uploaded system usage data.

18. The method of claim 17, further comprising the step of:
  incorporating the report into a patient file.

19. The method of claim 18, wherein the steps of generating the report and incorporating the report into a patient file are performed automatically and electronically.

20. The method of claim 11, further comprising the step of:
  providing a password prompt to access the operator interface.

21. A multi-mode electrical therapeutic stimulation system comprising:
  an electrical therapeutic stimulation device comprising a first output channel and a second output channel;
  a first electrode assembly electrically connected to the first output channel; and
  a second electrode assembly electrically connected to the second output channel;
  wherein the electrical stimulation device comprises automatically reconfigurable internal switching circuitry electrically coupled to the first and second electrode assemblies, the switching circuitry having a first configuration for a first stimulation treatment mode and a second configuration for a second stimulation treatment mode, and wherein first and second stimulation treatment modes each comprise one of an interferential (IF) mode, a neuromuscular electrical stimulation (NMES) mode, a combination IF/NMES mode, or a pulsed direct current (PDC) mode.

22. The multi-mode electrical therapeutic stimulation system of claim 21, wherein the operator interface includes the user interface.

23. The multi-mode electrical therapeutic stimulation system of claim 21, wherein the electrical stimulation device comprises a memory portion operable to store at least one preprogrammed electrical therapeutic stimulation treatment program.

24. The multi-mode electrical therapeutic stimulation system of claim 23, wherein the at least one preprogrammed electrical therapeutic stimulation treatment program is customizable via an operator interface.

25. The multi-mode electrical therapeutic stimulation system of claim 23, wherein the at least one preprogrammed electrical therapeutic stimulation treatment program comprises at least one characteristic customizable via the user interface.

26. The multi-mode electrical therapeutic stimulation system of claim 21, wherein the first stimulation treatment mode comprises an IF mode and the second stimulation treatment mode comprises an NMES mode.

27. The multi-mode electrical therapeutic stimulation system of claim 21, wherein the reconfigurable internal switching circuitry comprises relay circuitry.

28. The multi-mode electrical therapeutic stimulation system of claim 21, wherein the reconfigurable internal switching circuitry comprises a high-voltage analog switch.

29. A method of delivering a multi-mode electrical therapeutic stimulation treatment program comprising the steps of:
providing a multi-mode electrical therapeutic stimulation system having first and second output channels and first and second electrode assemblies, the first and second electrode assemblies respectively associated with the first and second output channels;
storing in the stimulation system at least one electrical therapeutic stimulation treatment program comprising a first stimulation treatment mode portion and a second stimulation treatment mode portion;
delivering the first stimulation treatment mode portion of the selected muscle stimulation treatment program to a target treatment area of a user via the first and second electrode assemblies;
automatically switching the first and second output channels internal to the stimulation system; and
delivering the second stimulation treatment mode portion of the selected electrical therapeutic stimulation treatment program to a target treatment area of a user via the first and second electrode assemblies.

30. The method of claim 29, wherein the first stimulation treatment mode portion comprises an interferential (IF) mode and the second stimulation treatment mode portion comprises a neuromuscular electrical stimulation (NMES) mode.

31. The method of claim 29, further comprising the steps of:
providing at least one selectable treatment program via an operator interface; and
accepting at least one program selection via the operator interface.

32. The method of claim 31, further comprising the steps of:
providing the at least one program selection as an option via a user interface; and
accepting a treatment program selection via the user interface.

33. The method of claim 32, further comprising step of:
presenting at least one customizable characteristic of the treatment program selection via the user interface.

34. The method of claim 31, further comprising to step of:
presenting at least one customizable characteristic of the treatment program selection via the operator interface.

35. The method of claim 31, further comprising the step of providing a password prompt to access the operator interface.

36. The method of claim 31, further comprising the steps of:
storing multi-mode electrical therapeutic stimulation system usage data;
establishing a communication connection with a central database;
transmitting the stored multi-mode electrical therapeutic stimulation system usage data to the central database; and
reporting transmission status information.

37. The method of claim 36, further comprising the steps of:
providing an automated survey;
accepting and storing a survey response; and
transmitting the stored survey response with the multi-mode electrical therapeutic stimulation system usage data to the central database.

38. The method of claim 37, further comprising the step of:
matching the transmitted survey response and the usage data with a patient file.

39. The method of claim 38, further comprising the step of:
incorporating the transmitted survey response and the usage data into the patient file.

40. The method of claim 39, further comprising the step of:
generating a report based at least in part upon the transmitted survey response and the usage data.

41. The method of claim 40, wherein the step of generating a report is performed prior to incorporating the transmitted survey response and the usage data into the patient file.

42. The method of claim 40, wherein the steps of matching, generating, and incorporating are performed automatically and electronically.

43. A multi-mode electrical therapeutic stimulation device comprising:
a case housing a stimulator, the case including an output channel interface operable to electrically couple a cable, electrode or other treatment applicator to the stimulator;
an interface including an input portion and an output portion, wherein the output portion comprises a display screen for displaying options of a first and a second electrostimulation treatment mode, or a combination of the first and second electrostimulation treatment modes, to a user or operator, and the input portion is operable to receive input from a user or operator for selecting the first or the second electrostimulation treatment mode displayed via the output portion;
a stimulator adapted to deliver a first and a second electro stimulation signal corresponding, respectively, to the first and second electro stimulation treatment modes, the stimulator comprising a first output channel having first and second electrical nodes, and a second output channel having first and a second electrical nodes, and channel switching circuitry, wherein the channel switching circuitry is adapted to enable delivery of the first electrostimulation signal though the first and second electrical nodes of the first output channel, and the second electrostimulation signal though the first electrical node of the first output channel and the first electrical node of the second output channel.

44. The multi-mode electrical therapeutic stimulation device of claim 43, wherein the first electrostimulation treatment mode is a IF treatment mode and the second electrostimulation treatment mode is an NMES treatment mode.

45. The multi-mode electrical therapeutic stimulation device of claim 43, wherein the switching circuitry comprises internal relays.

46. A stimulation device providing electrical stimulation therapy, comprising:
   a set of electrodes comprising a first pair of electrodes and a second pair of electrodes, the set adapted for placement on a treatment area of a patient to form a placement position;
   a first output circuit for delivering a first electrical stimulation treatment to the set of electrodes and comprising a first output portion and a second output portion;
   a second output circuit for delivering a second electrical stimulation treatment to the set of electrodes and comprising a first output portion and a second output portion;
   a first channel output electrically connected to the first pair of electrodes;
   a second channel output electrically connected to the second pair of electrodes; and
   a switching circuit operably connected to the first and second output circuits and the first and second channel outputs and having a first selectable switching position and a second selectable switching position, wherein:
      the first switching position completes an electrical connection between the first output portion of the first output circuit and the first pair of electrodes and between the second output portion of the first output circuit and the second pair of electrodes, thereby forming a first electrical electrode configuration and delivering a first stimulation treatment to the treatment area, and
      the second switching position completes an electrical connection of the first output portion of the second output circuit and one electrode of the first pair of electrodes and one electrode of the second pair of electrodes and an electrical connection of the second output portion of the second output circuit and one electrode of the first pair of electrodes and one electrode of the second pair of electrodes, thereby forming a second electrical electrode configuration and delivering a second stimulation treatment to the treatment area;
      such that electrical stimulation therapy may be automatically switched between a first stimulation treatment utilizing a first electrical electrode configuration and a second stimulation treatment utilizing a second electrical electrode configuration without changing the placement position of the set of electrodes.

47. The stimulation device of claim 46, wherein the first stimulation treatment is an interferential stimulation treatment and the second stimulation treatment is an NMES treatment.

48. The stimulation device of claim 46, wherein the first electrical configuration comprises a cross-electrode configuration and the second electrical configuration comprises a parallel-electrode configuration.

49. The stimulation device of claim 46, wherein a selection of the first selectable switching position or the second selectable switching position is determined by an external input to the stimulation device.

50. The stimulation device of claim 46, wherein the switching circuit comprises internal relays.

* * * * *